(12) United States Patent
Coleman et al.

(10) Patent No.: US 11,006,838 B2
(45) Date of Patent: May 18, 2021

(54) DEVICES, SYSTEM AND METHODS FOR MONITORING PHYSIOLOGICAL FUNCTIONS FROM SURFACE ELECTROPHYSIOLOGICAL SENSORS

(71) Applicant: The Regents of the University of California, Oakland, CA (US)

(72) Inventors: Todd Coleman, La Jolla, CA (US); Armen Gharibans, San Diego, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 5 days.

(21) Appl. No.: 16/303,610

(22) PCT Filed: May 22, 2017

(86) PCT No.: PCT/US2017/033871
§ 371 (c)(1),
(2) Date: Nov. 20, 2018

(87) PCT Pub. No.: WO2017/201538
PCT Pub. Date: Nov. 23, 2017

(65) Prior Publication Data
US 2019/0350484 A1 Nov. 21, 2019

Related U.S. Application Data

(60) Provisional application No. 62/339,689, filed on May 20, 2016.

(51) Int. Cl.
*A61B 5/00* (2006.01)
*A61B 5/01* (2006.01)
(Continued)

(52) U.S. Cl.
CPC ............ *A61B 5/015* (2013.01); *A61B 5/0008* (2013.01); *A61B 5/392* (2021.01); *A61B 5/6831* (2013.01);
(Continued)

(58) Field of Classification Search
CPC ....... A61B 5/04; A61B 5/0488; A61B 5/0492; A61B 5/6823; A61B 5/7282; A61B 5/725;
(Continued)

(56) References Cited

U.S. PATENT DOCUMENTS 5,713,367 A 2/1998 Arnold et al.
6,115,623 A 9/2000 McFee
(Continued)

FOREIGN PATENT DOCUMENTS

NZ 579235 A 2/2012
WO 2015130829 A1 9/2015

OTHER PUBLICATIONS

Abell, T. et al., "Gastric electromechanical function and gastric emptying in diabetic gastroparesis," European Journal of Gastroenterology and Hepatology, vol. 3, No. 2, pp. 163-167, 1991.
(Continued)

*Primary Examiner* — Mallika D Fairchild
(74) *Attorney, Agent, or Firm* — Perkins Coie LLP

(57) ABSTRACT

Disclosed are devices, systems and methods for monitoring electrophysiological function from anatomical structures, including gastric slow-waves in high resolution electrogastrograms. In some aspects, a device includes an electrophysiological sensor structured to include an array of electrodes spatially arranged on a substrate and operable to acquire electrophysiological signals to obtain time-series data, the electrodes spaced about an anatomical structure on the subject's body with at least one electrode placed with
(Continued)

reference to an anatomical landmark and other electrodes of the electrode array each placed at a spatial distance from another of the surface electrodes; and a data processing unit to process spatially resolved time-series data based on the electrophysiological signals to determine wave propagation parameters including direction and/or speed for each time point of interest of the acquired electrophysiological signals, in which the wave propagation parameters are associated with a physiological function of the anatomical structure of the subject's body.

21 Claims, 23 Drawing Sheets

(51) Int. Cl.
    *A61B 5/392*         (2021.01)
    *G16H 20/30*        (2018.01)
    *G16H 40/67*        (2018.01)

(52) U.S. Cl.
    CPC ...... *A61B 5/6833* (2013.01); *A61B 2562/046* (2013.01); *G16H 20/30* (2018.01); *G16H 40/67* (2018.01)

(58) Field of Classification Search
    CPC ....... A61B 5/7253; A61B 5/721; A61B 5/015; A61B 5/392; A61B 5/0008; A61B 5/6831; A61B 5/3833
    See application file for complete search history.

(56) References Cited

U.S. PATENT DOCUMENTS

| | | |
|---|---|---|
| 2008/0183092 A1 | 7/2008 | Smith et al. |
| 2009/0084674 A1 | 4/2009 | Holzhacker et al. |
| 2013/0046150 A1 | 2/2013 | Devanaboyina |
| 2015/0080695 A1 | 3/2015 | Rogers et al. |

OTHER PUBLICATIONS

Angeli, T.R. et al., "Loss of interstitial cells of cajal and patterns of gastric dysrhythmia in patients with chronic unexplained nausea and vomiting," Gastroenterology 2015, 149, pp. 56-66.
Bradshaw, L.A. et al., "Surface current density mapping for identification of gastric slow wave propa-gation," IEEE Transaction on Biomedical Engineering, vol. 56, No. 8, pp. 2131-2139, 2009.
Bradshaw, L.A. et al., "Diabetic gastroparesis alters the biomagnetic signature of the gastric slow wave," Neurogastroenterology & Motility, 2016, 28, pp. 837-848.
Brzana, R.J., et al., "Gastric myoelectrical activity in patients with gastric outlet obstruction and idiopathic gastroparesis," The American Journal of Gastroenterology, vol. 93, No. 10, pp. 1803-1809, 1998.
Buist, M. et al., "Multiscale modelling of human gastric electric activity: can the electrogastrogram detect functional electrical uncoupling?" Experimental Physiology, vol. 91, No. 2, pp. 383-390, 2006.
Burdan, F. et al., "Anatomical classification of the shape and topography of the stomach," Surgical and Radiologic Anatomy, vol. 34, No. 2, pp. 171-178, 2012.
Chen, J.D.Z. et al., "Detection of gastric slow wave propagation from the cutaneous electrogastrogram," American Journal of Physiology-Gastrointestinal and Liver Physiology, vol. 277, No. 2, pp. G424-G430, 1999.
Cheng, L.K. et al., "Anatomically realistic multiscale models of normal and abnormal gastrointestinal electrical activity," World Journal of Gastroenterology, vol. 13, No. 9, p. 1378, 2007.
Du, P. et al., "High-resolution mapping of in vivo gastrointestinal slow wave activity using flexible printed circuit board electrodes: Methodology and validation," Annals of Biomedical Engineering, vol. 37, No. 4, pp. 839-846, 2009.
Du, P. et al., "A multiscale model of the electrophysiological basis of the human electrogastrogram," Biophysical Journal, vol. 99, No. 9, pp. 2784-2792, 2010.
Fleet, D.J. et al., "Computation of component image velocity from local phase information," International Journal of Computer Vision, vol. 5, No. 1, pp. 77-104, 1990.
Garcia-Casado, J. et al., "Enhancement of non-invasive recording of electroenterogram by means of a flexible array of concentric ring electrodes," Annals of Biomedical Engineering, vol. 42, No. 3, pp. 651-660, 2013.
Geldof, H. et al., "Electrogastrographic study of gastric myoelectrical activity in patients with unexplained nausea and vomiting." Gut, vol. 27, No. 7, pp. 799-808, 1986.
Gharibans, A. et al., "Simultaneous EGG and Wireless Motility Capsule Recording in Gastroparesis: Abnormal Slow-Wave Direction Associated with Increased Gastric Pressure", Gastroenterology, vol. 150, issue 4, S728.
Gharibans, A.A. et al., "High-Resolution Electrogastrogram: A Noninvasive Method for Determining Gastric Slow-Wave Direction and Speed", IEEE Transactions on Biomedical Engineering. In Review.
He, B. et al., "Body surface Laplacian ECG mapping," IEEE Transaction on Biomedical Engineering, vol. 39, No. 11, pp. 1179-1191, 1992.
Hjorth, B. "An on-line transformation of EEG scalp potentials into orthogonal source derivations," Electroencephalography and Clinical Neurophysiology, vol. 39, No. 5, pp. 526-530, 1975.
Hjorth, B. "Source derivation simplifies topographical EEG interpretation," American Journal of EEG Technology, vol. 20, No. 3, pp. 121-132, 1980.
Hu, S. et al., "Motion sickness severity and physiological correlates during repeated exposures to a rotating optokinetic drum." Aviation, Space, and Environmental Medicine, 1991.
Koch, K.L., "Gastric emptying and gastric myoelectrical activity in patients with diabetic gastro-paresis: effect of long-term domperidone treatment." The American Journal of Gastroenterology, vol. 84, No. 9, pp. 1069-1075, 1989.
Kuo, B. et al., "Comparison of gastric emptying of a nondigestible capsule to a radio-labelled meal in healthy and gastroparetic subjects", Alimentary Pharmacology & Therapeutics 27.2, 2008, pp. 186-196.
Kwiatek, M.A. et al., "Quantification of distal antral contractile motility in healthy human stomach with magnetic resonance imaging," Journal of Magnetic Resonance Imaging, vol. 24, No. 5, pp. 1101-1109, 2006.
Liang, J.I.E. et al., "What can be measured from surface electrogastrography (computer simulations)," Digestive Diseases and Sciences, vol. 42, No. 7, pp. 1331-1343, 1997.
Lindberg, G. et al., "24-hour ambulatory electrogastrography in healthy volunteers", Scandinavian Journal of Gastroenterology (1996), 658-664.
Marciani, L., "Assessment of gastrointestinal motor functions by MRI: a comprehensive review," Neurogastroenterology & Motility, vol. 23, No. 5, pp. 399-407, 2011.
Nikias, C.L. et al., "The zero-delay wavenumber spectrum estimation for the analysis of array ECG signals—an alternative to isopotential mapping." IEEE Transactions on Biomedical Engineering, vol. 33, No. 4, pp. 435-452, 1986.
Nunez, P.L. et al., "The spline-Laplacian in clinical neurophysiology: a method to improve EEG spatial resolution." Journal of Clinical Neurophysiology, vol. 8, No. 4, pp. 397-413, 1991.
O'Grady, G. et al., "Origin and propagation of human gastric slow-wave activity defined by high-resolution mapping," American Journal of Physiology-Gastrointestinal and Liver Physiology, vol. 299, No. 3, pp. G585-G592, 2010.
O'Grady, G. et al., "Abnormal initiation and conduction of slow-wave activity in gastroparesis, defined by high-resolution electrical mapping," Gastroenterology, vol. 143, No. 3, pp. 589-598, 2012.
Pal, A. et al., "Gastric flow and mixing studied using computer simulation," Proceedings of the Royal Society of London B: Biological Sciences, vol. 271, No. 1557, pp. 2587-2594, 2004.

(56) References Cited

OTHER PUBLICATIONS

Parkman, H.P. et al., "Electrogastrography: a document prepared by the gastric section of the American motility society clinical GI motility testing task force," Neurogastroenterology & Motility, vol. 15, No. 2, pp. 89-102, 2003.

Pfaffenbach, B. et al., "Gastric dysrhythmias and delayed gastric emptying in patients with functional dyspepsia," Digestive Diseases and Sciences, vol. 42, No. 10, pp. 2094-2099, 1997.

Riezzo, G. et al., "Gastric electrical activity and gastrointestinal hormones in dyspeptic patients," Digestion, vol. 63, No. 1, pp. 20-29, 2001.

Rubino, D. et al., "Propagating waves mediate information transfer in the motor cortex," Nature Neuroscience, vol. 9, No. 12, pp. 1549-1557, 2006.

Schulze, K., "Imaging and modelling of digestion in the stomach and the duodenum," Neurogastroen-terology & Motility, vol. 18, No. 3, pp. 172-183, 2006.

Verhagen, M., et al., "Pitfalls in the analysis of electrogastrographic recordings," Gastroenterology, vol. 117, No. 2, pp. 453-460, 1999.

Wang, Z.S. et al., "Detection of gastric slow wave uncoupling from multi-channel electrogastrogram: validations and applications," Neurogastroenterology & Motility, vol. 15, No. 5, pp. 457-465, 2003.

International Search Report and Written Opinion for PCT Application No. PCT/US2017/033871, dated Aug. 17, 2017, 21 pages.

EPO, Extended European Search Report for European Patent Application No. 17800339.8. dated Dec. 12, 2019. 11 pages.

Irimia, A. et al. "Separation of gastric electrical control activity from simultaneous MGG/EGG recordings using independent component analysis" EMBS Annual International Conference, Aug. 30-Sep. 3, 2006, pp. 3110-3113.

Yassi et al. "The gastrointestinal electrical mapping suite (GEMS): software for analyzing and visualizing high-resolution (multi-electrode) recordings in spatiotemporal detail" BMC Gastroenterology, vol. 12, No. 60, 2012, 14 pages.

DEVICES, SYSTEM AND METHODS FOR MONITORING PHYSIOLOGICAL FUNCTIONS FROM SURFACE ELECTROPHYSIOLOGICAL SENSORS

CROSS-REFERENCE TO RELATED APPLICATIONS

This patent document is a 371 National Phase Application of PCT Application No. PCT/US2017/033871 entitled "DEVICES, SYSTEMS AND METHODS FOR MONITORING PHYSIOLOGICAL FUNCTIONS FROM SURFACE ELECTROPHYSIOLOGICAL SENSORS" filed on May 22, 2017 which claims priorities to and benefits of U.S. Provisional Patent Application No. 62/339,689 entitled "CHARACTERIZING GASTROINTESTINAL FUNCTIONS FROM SURFACE ELECTROPHYSIOLOGY RECORDING" filed on May 20, 2016. The entire content of the aforementioned patent applications are incorporated by reference as part of the disclosure of this patent document.

TECHNICAL FIELD

This patent document relates to systems, devices and methods for electrophysiology surface recordings and characterization of electrophysiological signals.

BACKGROUND

Various existing clinical tools to diagnose most gastrointestinal (GI) diseases are invasive or require radiation. Endoscopy is a common GI diagnostic procedure, where a catheter is inserted through the mouth, down the esophagus and into the stomach. This technique can be used to detect visual abnormalities (e.g., inflammation, obstruction) or take a biopsy for analysis. However, endoscopy cannot assess GI function.

Existing tests that assess GI function include the gastric emptying test or manometry procedure. For example, gastric emptying tests typically measure how quickly the stomach empties a radioactively labeled meal, in which the percentage of the meal remaining in the stomach is imaged and recorded for an extended period (e.g., 4 hours in some instances). Gastric emptying tests can assess limited functional abnormalities of the GI system, such as dumping syndrome (i.e., stomach emptying too quickly) or gastroparesis (i.e., delayed stomach emptying with no obstruction). However, implementations for this test suffer from drawbacks such as poor repeatability, inconclusivity (e.g., if the patient vomits during the test), and required use of radioactive materials. Another example of a GI test to assess GI function is a manometry procedure, which is an invasive technique involving a catheter placed either through the mouth/nose or anus, and pressure sensors placed along the catheter to measure the physical contractions in the GI system. Due to the difficulties associated with administering the manometry procedure and interpreting the test results, this test tends to be less available due to a small number of skilled gastroenterologists.

Electrophysiology is a method of characterizing various body functions using electrodes to measure an electrical signal associated with a physiological function. Examples of electrophysiological measurements include an electrocardiogram (ECG) to characterize cardiac functions and an electroencephalogram (EEG) to characterize brain function. For GI measurements, electrogastrography is a noninvasive technique for recording gastric myoelectric activity (e.g., also referred to as gut electrophysiology) using electrodes placed cutaneously on the abdominal surface overlaying the stomach. Cutaneous electrogastrography provides an indirect representation of the electrical activity of the anatomical structures of the GI system. Due to its relative simplicity and safety, cutaneous electrogastrography is considered an attractive modality.

However, electrogastrogram (EGG) measurements are not widely used, which may be attributed to its poor correlation with gastric emptying tests, antroduodenal manometry, and the actual disease status, along with inconsistent results, poor signal quality, etc. Moreover, a high exclusion rate of patients have resulted from unpredictable results due to motion artifacts or other unknown factors. As such, despite the attractive qualities of EGG like simplicity and noninvasiveness, the use of EGG remains limited in clinical practice for assessing gastric disorders. Advancements in EGG technology are required to produce reliable, noninvasive systems and protocols for measuring gastrointestinal physiology that would allow for widespread adoption.

SUMMARY

Disclosed are devices, systems and methods for monitoring electrophysiological functions based on wave propagation parameters measured from anatomical structures using surface electrophysiological sensors, which can be worn by a user.

In some embodiments in accordance with the present technology, a device for electrophysiological monitoring includes an electrophysiological sensor structured to include an array of electrodes spatially arranged on a substrate and operable to acquire electrophysiological signals from the electrodes of the array when in contact with skin of a subject to obtain time-series data of the electrophysiological signals, in which the electrodes are spaced about an anatomical structure on the subject's body with at least one electrode placed with reference to an anatomical landmark and other electrodes of the electrode array each placed at a spatial distance from another of the surface electrodes, whereby all the surface electrodes have a determined location with respect to the anatomical landmark; an electronics unit including a signal conditioning circuit to amplify the acquired electrophysiological signals; and a data processing unit including a processor to process data based on the amplified acquired electrophysiological signals, the data processing unit configured to spatially filter the time-series data to generate a spatially resolved time-series data set that includes a reduced amount of data than the obtained time-series data of electrophysiological signals, and to process the spatially resolved time-series data set to determine wave propagation parameters including one or both of direction and speed for each time point of interest of the acquired electrophysiological signals, in which the wave propagation parameters are associated with a physiological function of the anatomical structure of the subject's body to which the electrophysiological sensor is in contact.

In some embodiments in accordance with the present technology, a device for electrophysiological monitoring includes an electrophysiological sensor structured to include an array of electrodes spatially arranged on a substrate and operable to acquire electrophysiological signals from the electrodes of the array when in contact with skin of a subject to obtain time-series data of the electrophysiological signals, in which the electrodes are spaced about an anatomical structure on the subject's body with at least one electrode placed with reference to an anatomical landmark and other electrodes of the electrode array each placed at a spatial distance from another of the surface electrodes, whereby all the surface electrodes have a determined location with respect to the anatomical landmark; and a data processing unit including a processor to process spatially resolved time-series data based on the acquired electrophysiological signals, the data processing unit configured to determine wave propagation parameters including one or both of direction and speed for each time point of interest of the acquired electrophysiological signals, in which the wave propagation parameters are associated with a physiological function of the anatomical structure of the subject's body to which the electrophysiological sensor is in contact.

In some embodiments in accordance with the present technology, a method for electrophysiological monitoring includes acquiring electrophysiological signals from surface electrodes of an electrode array coupled to skin of a subject to obtain time-series data of the electrophysiological signals; processing the time-series data to produce processed time-series data, in which the processing includes spectral filtering the time-series data, down-sampling the time-series data, or removing signal artifacts from the time-series data; spatially filtering the processed time-series data to generate a spatially resolved time-series data set, in which the spatially resolved time-series data set includes a reduced amount of data than the processed time-series data of electrophysiological signals; processing the spatially resolved time-series data set to extract wave propagation parameters including one or both of direction and speed for each time point of interest of the acquired electrophysiological signals, in which the wave propagation parameters are associated with a physiological function of an anatomical structure of the subject's body to which the electrode array is coupled, the producing the wave propagation parameters includes analyzing phase information of the spatially resolved time-series data set; and producing an electrophysiological monitoring output that includes the extracted wave propagation parameters to provide information on the physiological function of the anatomical structure of the subject's body.

In some embodiments in accordance with the present technology, a method for electrophysiological monitoring includes acquiring electrophysiological signals from surface electrodes of an electrode array coupled to skin of a subject to obtain time-series data of the electrophysiological signals, in which the surface electrodes of the electrode array are spatially arranged about an anatomical structure on the subject's body with at least one electrode placed with reference to an anatomical landmark and other electrodes of the electrode array each placed at a spatial distance from another of the surface electrodes, whereby all the surface electrodes have a determined location with respect to the anatomical landmark; processing the time-series data to produce processed time-series data, in which the processing includes spectral filtering the time-series data, down-sampling the time-series data, or removing signal artifacts from the time-series data; determining average intensity values of the electrophysiological signals over a course of the time-series data; mapping the average intensity values to locations where the of the surface electrodes are coupled to the subject; and producing an electrophysiological signal heat map output of the mapped average intensity values on one or both of a graph and image of an anatomical structure of the subject's body, in which the mapped average intensity values are associated with a physiological function of the anatomical structure.

In some embodiments in accordance with the present technology, a method for electrophysiological monitoring includes acquiring electrophysiological signals from electrodes of an electrode array coupled to skin of a subject to obtain time-series data of the electrophysiological signals; processing the time-series data to produce processed time-series data, in which the processing includes spectral filtering the time-series data, down-sampling the time-series data, or removing signal artifacts from the time-series data; and processing spatially resolved time-series data based on the electrophysiological signals to determine wave propagation parameters including one or both of direction and speed for each time point of interest of the acquired electrophysiological signals, in which the wave propagation parameters are associated with a physiological function of an anatomical structure of the subject's body to which the electrode array is coupled.

In some embodiments in accordance with the present technology, a system for characterizing gastrointestinal functions includes an array of electrodes spatially arranged and in contact with skin of a subject over the gastrointestinal region to record gut electrophysiology signals; and a processing unit in communication with the array of electrodes to receive gut electrophysiology signals and including a processor that processes the gut electrophysiology signals to determine spatial propagation of a gastric slow-wave signal across time associated with the gut electrophysiology of the subject.

In some aspects, the methods, systems, and devices in accordance with the present technology include noninvasive surface sensor electrodes to acquire electrophysiological signals for characterizing spatial properties of the electrophysiological signals associated with functional phenomenon of anatomical structures, such as of the gastrointestinal system, including producing high-resolution electrogastrogram (HR-EGG).

The devices, systems and methods disclosed in this patent document can be implemented in various ways to include one or more of the following features. For example, in some aspects, a system is disclosed for non-invasively characterizing gastrointestinal functions using multiple electrodes to determine spatial wave propagation that arises from the stomach activity, which can be used to produce a HR-EGG. Over half of the patients with gastric problems (e.g., slow emptying) or unexplained nausea and vomiting, have spatial abnormalities that occur at a regular frequency. The HR-EGG produced by the example system can disambiguate healthy state from disease state non-invasively. The example system includes an array of electrodes spatially arranged and in contact with skin of a subject over the gastrointestinal region to record gut electrophysiology signals and a processing unit in communication with the array of electrodes. The electrode spacing and measurement area of the array of electrodes are spatially arranged to avoid spatial aliasing of the gastric slow-wave signal and to ensure spatial coverage of the organ. The processing unit includes memory and a processor to determine spatial propagation of a gastric slow-wave signal across time associated with the gut electrophysiology of the subject. In some implementations, for example, the processing unit can be configured to provide decision support information for the subject.

In some implementations, the spatial arrangement of the array of electrodes is based on imaging data or previous medical history of the subject. The imaging data can include electrical impedance tomography data, CT, MRI, ultrasound, x-ray, fluoroscopy, etc. The electrodes can include a physical design to directly record the surface Laplacian. The processing unit can be configured to estimate the surface Laplacian. The processing unit also can be configured to estimate at least one of presence, direction, or speed of the gastric slow-wave signal. The system can also include a biopotential amplifier to filter and/or digitize the recorded gut electrophysiological signals as signal data provided to the data processing unit. The electrodes of the array can be spatially arranged about the gastrointestinal region with at least one electrode placed with reference to an anatomical landmark of the gastrointestinal region and other electrodes of the array are placed at a spatial distance from another of the electrodes. The array of electrodes can include a 5×5 grid. The anatomical landmark of the gastrointestinal region can include the xiphoid or umbilicus. The system can also include flexible electronic components attachable to the skin of the subject to record signals associated with the gut electrophysiology.

Also disclosed in this patent document are methods of characterizing gastrointestinal functions using the systems disclosed herein.

DETAILED DESCRIPTION

Figure 1A:
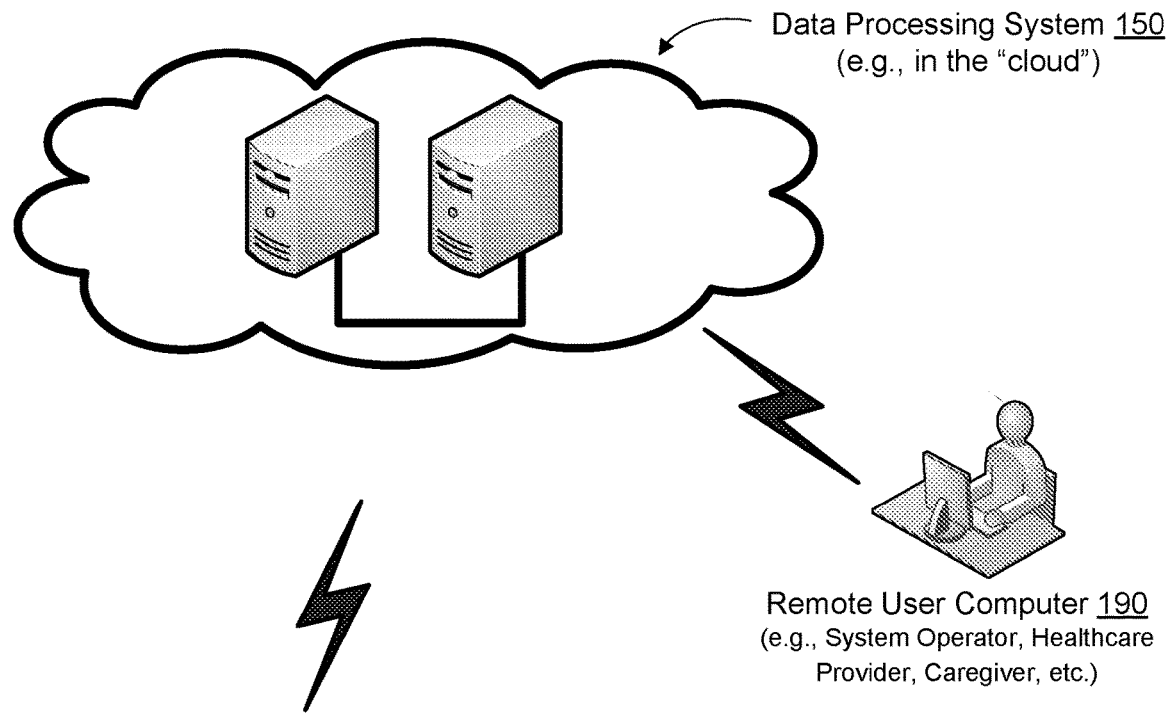
FIG. 1A shows a diagram of an example system for monitoring electrophysiological data obtained by a wearable sensor device in accordance with the present technology.
Figure 1A:
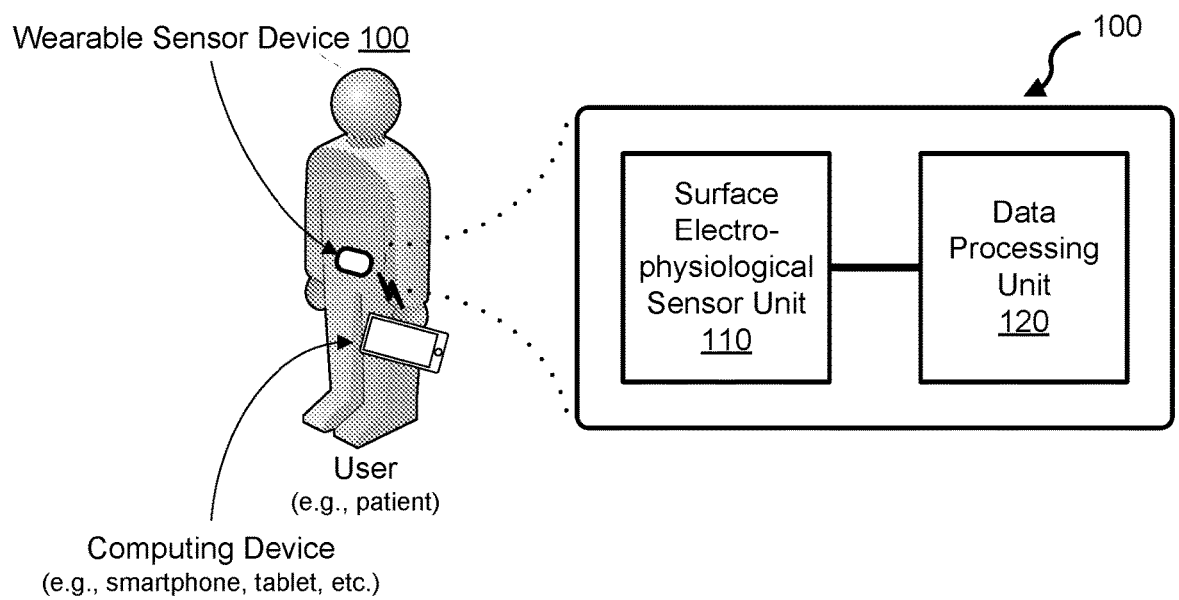

Disclosed are devices, systems and methods for monitoring electrophysiological functions based on wave propagation parameters measured from anatomical structures using surface electrophysiological sensors, which can be worn by a user.

The disclosed devices, systems and methods can provide noninvasive, real-time and automated monitoring of spatial properties of electrophysiological signals including directionality and source that are associated with physiological functionality of the tissues, organs and organ systems to which the electrophysiological sensors are applied. The disclosed technology provides a versatile sensor platform that can be applied to any part of the user's body proximate the target tissue, organ or organ system to spatially map the monitored electrophysiological wave properties to pinpoint locations of the body, e.g., allowing for applications on subjects of any body type. For example, the disclosed sensor platform does not depend on the placement of a reference electrode. Moreover, operations of the sensor platform can be fully-automated, e.g., enabling ambulatory, remote monitoring of a patient and/or applications in a primary care facility by non-specialists. The disclosed technology includes data processing techniques to generate the spatial information about the interrogated anatomical structures, making it capable to discern and identify abnormal and normal physiological phenomenon. The disclosed devices, systems and methods can be used for noninvasive, real-time and ambulatory monitoring of the gastrointestinal system to determine gastric slow-wave spatial functionality, including abnormalities that otherwise can go undetected by traditional sensor devices. For example, the gastric slow-wave propagation direction and speed at each time point are measurable using surface electrodes from example devices in accordance with the present technology.

While the disclosed embodiments are described herein primarily based on physiological monitoring of the gastrointestinal system to facilitate understanding of the underlying concepts, it is understood that the disclosed embodiments can also include monitoring of other tissues, organs and organ systems, particularly for smooth muscle for organs and organ systems, and skeletal muscles.

Rates of diagnosis for gastrointestinal (GI) medical conditions have increased markedly in recent years. However, many such diagnoses are made in broad, idiopathic categories, an example being irritable bowel syndrome (IBS), which covers a myriad of symptoms but lacks a fundamental physiological underpinning. Even though the electrogastrogram (EGG) has existed for decades, its use as a diagnostic and research tool has been limited. Alternative measures to EGG are invasive, expensive and/or require expertise to administer. While the simplicity and safety of EGG make it attractive for diagnosing abnormalities in gastric motility, EGG has been unsuccessful in providing consistent and reliable data on gut electrophysiology largely due to system constraints with electrodes and/or signal processing techniques. For example, conventional EGG systems are incapable of monitoring spatial gastric myoelectric abnormalities, as conventional approaches rely on time-frequency analysis of single channels.

Spectral analysis of a single EGG channel has been attempted to quantify anomalies. For example, normal EGG readings have traditionally been defined as demonstrating a 2-4 cycles/minute frequency (e.g., 0.0333 to 0.0667 Hz) for at least 70% of a recording. Moreover, the amplitude of the signal increases after meal ingestion for normal subjects, reflecting a postprandial increase in the electromechanical activity of the stomach. EGG irregularities, including bradygastria, tachygastria, and concurrent loss of signal amplitude, can increase with meal ingestion, which have been reported in patients with nausea and vomiting, dyspepsia, gastroparesis, and motion sickness.

It is still not yet established if there is a correlation between EGG parameters and abnormalities in gastric emptying, which may be attributed to the problems associated with conventional EGG systems. Some investigations have reported no relation, while others have reported a strong positive correlation. Overall, normal EGG does not assure normal gastric emptying (e.g., sensitivity<50%), but an abnormal EGG may predict delayed gastric emptying (e.g., specificity 78%-92%). In other words, while subjects with an abnormal EGG typically have delayed gastric emptying, there are patients with normal EGG who have delayed gastric emptying. The limitations with conventional techniques that have led to such inconsistencies is an important reason why EGG has not been widely adopted clinically.

The involuntary contractions in the stomach and small intestines mostly occur rhythmically. The frequency of the contractions is determined primarily by slow-waves of membrane potential in the smooth muscle that are controlled by interstitial cells of Cajal (ICCs), in the GI system, which are pacemaker cells that involuntarily depolarize and repolarize (e.g., about every 20 seconds) to set the gastric myoelectric rhythmicity. Slow-waves are not action potentials, but rather changes in the resting membrane potential that propagate axially. The amplitude of the slow-waves typically varies between 5 and 15 mV and the intrinsic frequency is different in various parts of the gastrointestinal tract. For example, in humans, the frequency of the stomach is around 3 cycles per minute (cpm), while the frequency of the duodenum oscillates between 8-12 cpm, and the terminal ileum at 8-9 cpm.

High-resolution electrical mapping during surgery has recently been carried out to understand normal gastric slow-wave activity. This conventional technique is invasive, and involves positioning a spatially dense electrode array directly on the surface of the stomach to allow for the recording and reconstruction of patterns of electrical activation. The finding for normal subjects, in brief, was that the gastric slow-waves originate in the pacemaker region of the corpus, quickly form circumferential bands around the stomach, propagate slowly in the axial direction at about 3 mm/s, and eventually terminate in the pylorus. Due to the slow speed of propagation, multiple wavefronts typically exist on the stomach surface at any given time. Using this invasive technique, gastric slow-waves in subjects with gastroparesis and chronic unexplained nausea and vomiting have been evaluated to attempt to define, quantify, and classify abnormalities with spatiotemporal detail. In such studies, aberrant initiation and conduction of the slow-waves was observed, which occasionally led to premature termination and colliding wavefronts. The crucial finding was that half of the subjects exhibited spatial abnormalities that occurred at the normal 3 cpm frequency. This suggests that single channel EGG recordings are unable to detect such abnormalities, which are validated based on a modeling study to further emphasize this point. By modeling both normal slow-wave propagation and a conduction block resulting in colliding wavefronts, it was revealed that a single channel EGG recording on the abdominal surface would be unable to detect the irregularity.

There have been attempts at extracting EGG spatial information from multiple surface electrodes in the past. The study placed four electrodes along the axis of the stomach, in which the amount of frequency coupling between channels was evaluated, with the notion that coupling between channels reflects normal wave propagation. This method, however, does not measure true wave propagation and therefore does not accurately estimate propagation velocity. Moreover, this approach is dependent on the precise placement of electrodes with respect to the gut, particularly the reference. If the reference electrode is positioned in a region with strong gastric signal, phase shifts will not be observed. Given the vast amount of inter-subject variability in stomach anatomy, standardizing electrode placement is extremely challenging, if not impossible.

In addition to the potentials recorded by surface electrodes in the EGG, the gastric electrical currents also produce a magnetic field that can be measured by a magnetometer, known as the magnetogastrogram (MGG). The relationship between the EGG and MGG is analogous to that of the electroencephalogram (EEG) and magnetoencephalogram (MEG) utilized for studying the activity of the brain. The MGG has been used to detect gastric slow-wave frequency and propagation with promising results, but a key feasibility distinction between the two modalities is that the MGG requires measuring the signal with large, expensive equipment in a controlled environment, while the EGG has the potential for ambulatory monitoring.

In some aspects, devices, systems and methods in accordance with the disclosed technology include an array of electrodes to estimate the direction and speed of the gastric slow-wave to produce a high-resolution electrogastrogram (HR-EGG). Example implementations of surface electrophysiological sensors in accordance with embodiments of the present technology are described, which demonstrate HR-EGGs in a variety of applications. In some implementations, a method and a system for determining gastric slow-wave propagation direction and speed from an array of skin-mounted electrodes are disclosed. For example, an array of cutaneous electrodes is shown to estimate the direction and speed of gastric slow-waves to produce HR-EGGs. The approach was verified on a forward electrophysiology model of the stomach, e.g., demonstrating that an accurate assessment of slow-wave propagation can be made using the example surface electrode device. Furthermore, in an example implementation of the disclosed method, propagation directions (e.g., 181±29 degrees) and speeds (e.g., 3.7±0.5 mm/s) were determined for healthy adult subjects, which are shown to be consistent with serosal recordings of slow-waves. It is envisioned that HR-EGG systems and methods in accordance with the disclosed technology can provide a fully automated tool capable of unveiling new classes of gastric abnormalities, which can lead to better diagnosis of diseases and inspire novel drugs and therapies, ultimately improving clinical outcomes.

Example embodiments of high-resolution electrogastrogram systems and methods are disclosed for determining gastric wave properties (e.g., gastric slow-wave propagation direction and speed) from an array of spatially arranged skin-mounted electrodes. A methodology for noninvasive estimation of gastric slow-wave propagation is outlined. This approach can be used to determine gastric slow-wave spatial abnormalities that can go undetected by traditional single channel recordings. The disclosed techniques do not depend on the placement of the reference electrode and are fully automated. As such, reliable estimates of slow-wave propagation direction and speed at each time point are generated using surface electrodes. The disclosed techniques can provide spatially detailed analysis of propagating gastric myoelectrical events, which can facilitate better understanding of the pathophysiology of gastric dysrhythmias among patients with motility disorders. This in turn may create opportunity for interventions to reduce gastric dysrhythmic activity and improve symptoms.

In some examples, the disclosed electrophysiological functional monitoring technology include techniques for surface Laplacian estimation and/or Spatial Wave estimation. For Spatial Wave estimation, for example, direction, velocity, and presence of the slow-wave can be obtained with surface electrodes, e.g., including electrode size/spacing to avoid spatial aliasing. For surface Laplacian estimation, for example, better spatial resolution can be provided by emphasizing superficial localized sources, while suppressing deep sources or ones that are widespread and coherent. Implementations of the surface Laplacian estimation and/or Spatial Wave estimation techniques can be completely automated, and require no user input. Implementations of the surface Laplacian estimation and/or Spatial Wave estimation techniques are able to estimate at every time point, which for example is unlike frequency based methods that may typically use 4 minute windows of data since the signal is so slow (e.g., 0.05 Hz). Implementations of the surface Laplacian estimation and/or Spatial Wave estimation techniques are robust to motion artifact, in which only sustained waves are extracted, which are unlikely to occur by chance.

EXAMPLE EMBODIMENTS

FIG. 1A shows a diagram of an example system for monitoring electrophysiological data obtained by a wearable sensor device in accordance with the present technology. The system includes an electrophysiological sensor device 100 wearable by a user. The electrophysiological sensor device 100 includes a surface electrophysiological sensor unit 110 in communication with a data processing unit 120. In some implementations, for example, the data processing unit 120 can be resident on a computing device, such as a mobile computing device, e.g., a smartphone, tablet and/or wearable computing device (e.g., smartwatch, smartglasses, etc.), or a computer including a laptop or desktop computer. The system includes a data processing system 150 in communication with the data processing unit 120 of the electrophysiological sensor device 100. In an example, such as that shown in FIG. 1A, the electrophysiological sensor device 100 communicates data obtained by the surface electrophysiological sensor unit 110 to a user's smartphone or tablet, which can process the obtained data for display on the smartphone or tablet and/or for transference to an external computer or computing system, such as the data processing system 150. In the example, the user having the smartphone or tablet can include the patient user wearing the surface electrophysiological sensor unit 110 or another user, such as a doctor, nurse, or other health care provider or caregiver.

In some embodiments, for example, the system includes a remote user computer 190 to remotely monitor data associated with the user obtained by the electrophysiological sensor device 100 and transferred to the data processing system 150, and/or to remotely operate aspects of the system. For example, the remote user computer 190 can include a personal computer such as a desktop or laptop computer, a mobile computing device such as a smartphone, tablet, smartwatch, etc., or other computing device.

In such embodiments, for example, the system includes a software application ("app") that is stored on the computer device of the user (e.g., patient user and/or other user such as a physician) and controls the processing and storage of the data received from the device 100 using the processor and memory of the user computer device. In some embodiments, the data processing system 150 includes one or more computing devices in a computer system or communication network accessible via the Internet (referred to as "the cloud"), e.g., including servers and/or databases in the cloud. In some embodiments, the data processing system 150 can be embodied on the user device (e.g., smartphone). Similarly, in some embodiments of the system, for example, the data processing system 150 includes the one or more computing devices in the cloud and the app resident on the user device to receive and manage data processing of the data obtained by the device 100. In some implementations, for example, the device 100 transfers data to a user computing device, e.g., using a low power wireless communication protocol (e.g., BLE), in which the app can control various data processing of the received data; and the app can transfer the data to the one or more computing devices in the cloud using a different communication protocol, e.g., including a wired or a wireless communication protocol such as LTE, Wi-Fi, or other.

Figure 1B:
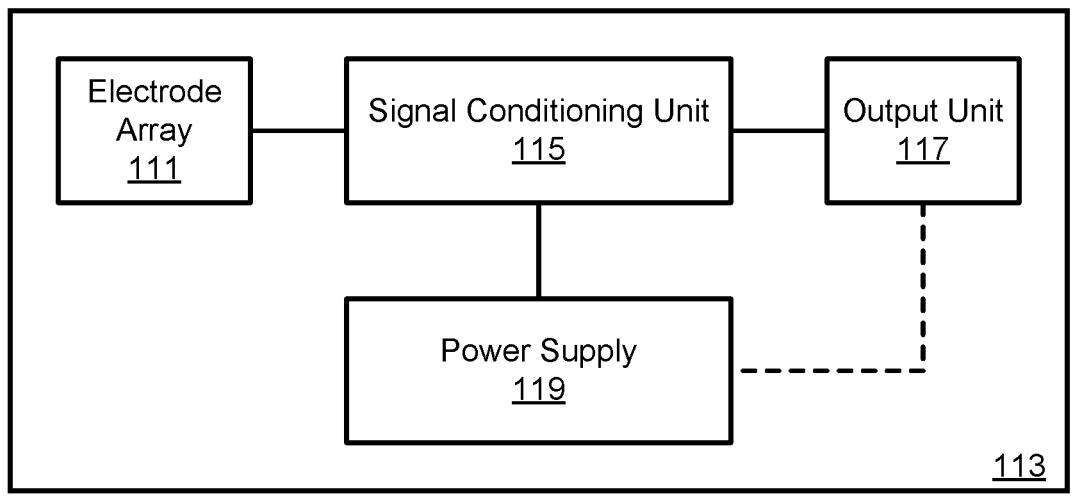
FIG. 1B shows a diagram of an example embodiment of a surface electrophysiological sensor unit.

FIG. 1B shows a diagram of an example embodiment of the surface electrophysiological sensor unit 110. In this example, an array of electrodes 111 are arranged on a substrate 113. In some embodiments, for example, the substrate includes a flexible and/or stretchable adhesive substrate, and the electrodes of the electrode array 111 are structured on or in the flexible and/or stretchable adhesive substrate. For example, the substrate 113 can include a material that is mechanically flexible (e.g., bendable) and/or mechanically stretchable to physically conform to and/or match the bending and/or stretching ability of the material (e.g., skin, fabric, etc.) to which the electrophysiological sensor device 100 is to attach. For example, in some implementations, the electrophysiological sensor device 100 can be configured as an adhesive patch to attach directly to the skin of the user. Whereas in some implementations, for example, the electrophysiological sensor device 100 can be configured in a fabric, plastic, or other material that can be attached to the user by a securement component, e.g., such as a belt, strap, etc. For example, in some implementations, the electrophysiological sensor device 100 includes a shirt or other clothing article worn by the user, in which the surface electrophysiological sensor unit 110 is secured, e.g., attached or embedded. In example embodiments of the substrate 113 that is flexible and/or stretchable, the substrate 113 can include, but is not limited to, a medical-use adhesive such as tegaderm, consumer grade adhesives (e.g., 3M Scotch®), consumer grade adhesives (e.g., 3M Scotch®), and other thin film materials including silicon-based, polyimide-based thin films. The substrate 113 can be configured to have a thickness in a range of a few millimeters to tens of microns, e.g., such as 10 µm thickness. In some implementations, the substrate 113 can allow for secure attachment, detachment and reattachment to the target area of the user's body.

In some implementations, for example, the wearable sensor device 100 can include a an electrochemical sensor and/or a physical sensor on the substrate 113. For example, the sensor unit 110 can include a temperature sensor, a humidity sensor, a pressure sensor, a motion sensor, glucose sensor, or a location sensor. The sensors can capture various detectable signals from the target region of the user to which the sensor unit 110 is attached, including motion signals, temperature signals, humidity signals, electrophysiological signals and electrochemical signals, among others. Similarly, the wearable sensor device 100 can include an actuator device, e.g., such as a medicinal delivery device, alert or alarm device, and/or other type of actuator device.

In the example embodiment of the surface electrophysiological sensor unit 110, as depicted in FIG. 1B, the sensor unit 110 can include a signal conditioning unit 115, an signal output unit 117, and/or a power supply 119. The signal conditioning unit 115 can include instrumentational amplifier(s) and filter(s) to condition the detected signal from the electrode array 111, e.g., improving signal-to-noise ratio. In some implementations, the signal conditioning unit 115 can include drive circuitry for operating the electrodes of the array 111 to perform the desired sensing mode for detecting the signals from the target. In some implementations, the signal conditioning unit includes a microcontroller and multiplexer to manage data acquisition on data channels from the electrodes. In some implementations, the output unit 117 can include electrical contacts that electrically interface with an electrical conduit to provide the data to the data processing unit 120. In some implementations, for example, the output unit can include a wireless transmitter or transceiver device, e.g., such as an RF front-end (RFE), that is capable of communicating with the data processing unit 120 to provide the data from the sensor unit 110. For example, an RFE can manage the communication protocol of the wireless signal to be transmitted and/or received by an antenna of the output unit 117 in such example embodiments. An example transceiver unit can include a BLE chipset to communicate with a BLE-enabled device, such as a smartphone. The power supply 119 can include a battery, fuel cell or other power source to supply power to the components of the sensor unit 110.

Figure 1C:
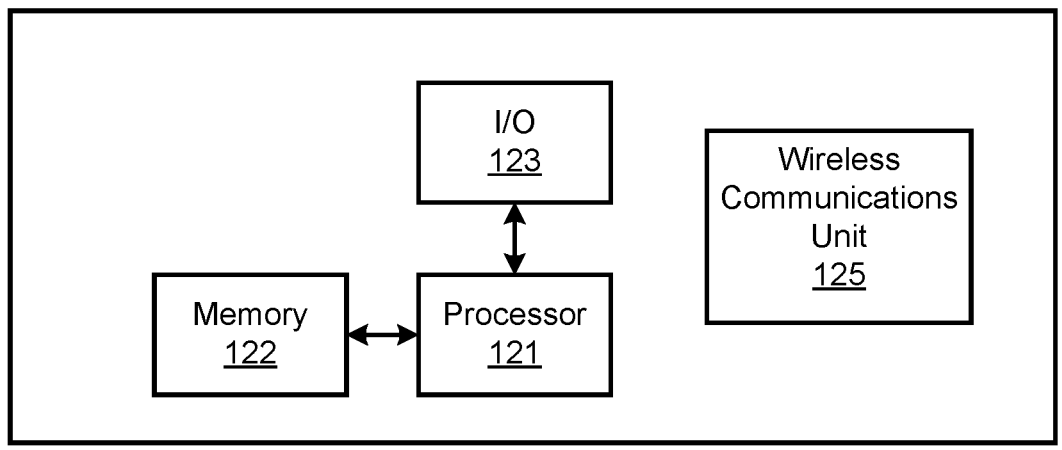
FIG. 1C shows a block diagram of an example embodiment of a data processing unit.

FIG. 1C shows a block diagram of an example embodiment of the data processing unit 120. In some implementations, the data processing unit 120 is embodied on the app resident on the user device and/or the one or more computing devices in the cloud. In some implementations, the data processing unit 120 is embodied on the substrate 113 and electrically coupled to the output unit 117. The data processing unit 120 includes a processor 121 to process data, and memory 122 in communication with the processor 121 to store and/or buffer data. For example, the processor 121 can include a central processing unit (CPU) or a microcontroller unit (MCU). For example, the memory 122 can include and store processor-executable code, which when executed by the processor, configures the data processing unit 120 to perform various operations, e.g., such as receiving information, commands, and/or data, processing information and data, and transmitting or providing information/data to another device. To support various functions of the data processing unit 120, the memory 122 can store information and data, such as instructions, software, values, images, and other data processed or referenced by the processor 121. For example, various types of Random Access Memory (RAM) devices, Read Only Memory (ROM) devices, Flash Memory devices, and other suitable storage media can be used to implement storage functions of the memory 122. In some implementations, the data processing unit 120 includes an input/output (I/O) unit 123 to interface the processor 121 and/or memory 122 to other modules, units or devices, e.g., associated with the data processing system 150 and/or external devices. In some embodiments, the data processing unit 120 includes a wireless communications unit 125, e.g., such as a transmitter (Tx) or a transmitter/receiver (Tx/Rx) unit. For example, in such embodiments, the I/O unit 123 can interface the processor 121 and memory 122 with the wireless communications unit 125, e.g., to utilize various types of wireless interfaces compatible with typical data communication standards, which can be used in communications of the data processing unit 120 with other devices, e.g., such as between the one or more computers in the cloud and the user device. The data communication standards include, but are not limited to, Bluetooth, Bluetooth low energy (BLE), Zigbee, IEEE 802.11, Wireless Local Area Network (WLAN), Wireless Personal Area Network (WPAN), Wireless Wide Area Network (WWAN), WiMAX, IEEE 802.16 (Worldwide Interoperability for Microwave Access (WiMAX)), 3G/4G/LTE cellular communication methods, and parallel interfaces. In some implementations, the data processing unit 120 can interface with other devices using a wired connection via the I/O unit 123. The data processing unit 120 can also interface with other external interfaces, sources of data storage, and/or visual or audio display devices, etc. to retrieve and transfer data and information that can be processed by the processor 121, stored in the memory 122, or exhibited on an output unit of the user device (e.g., smartphone) or an external device.

Figure 1D:
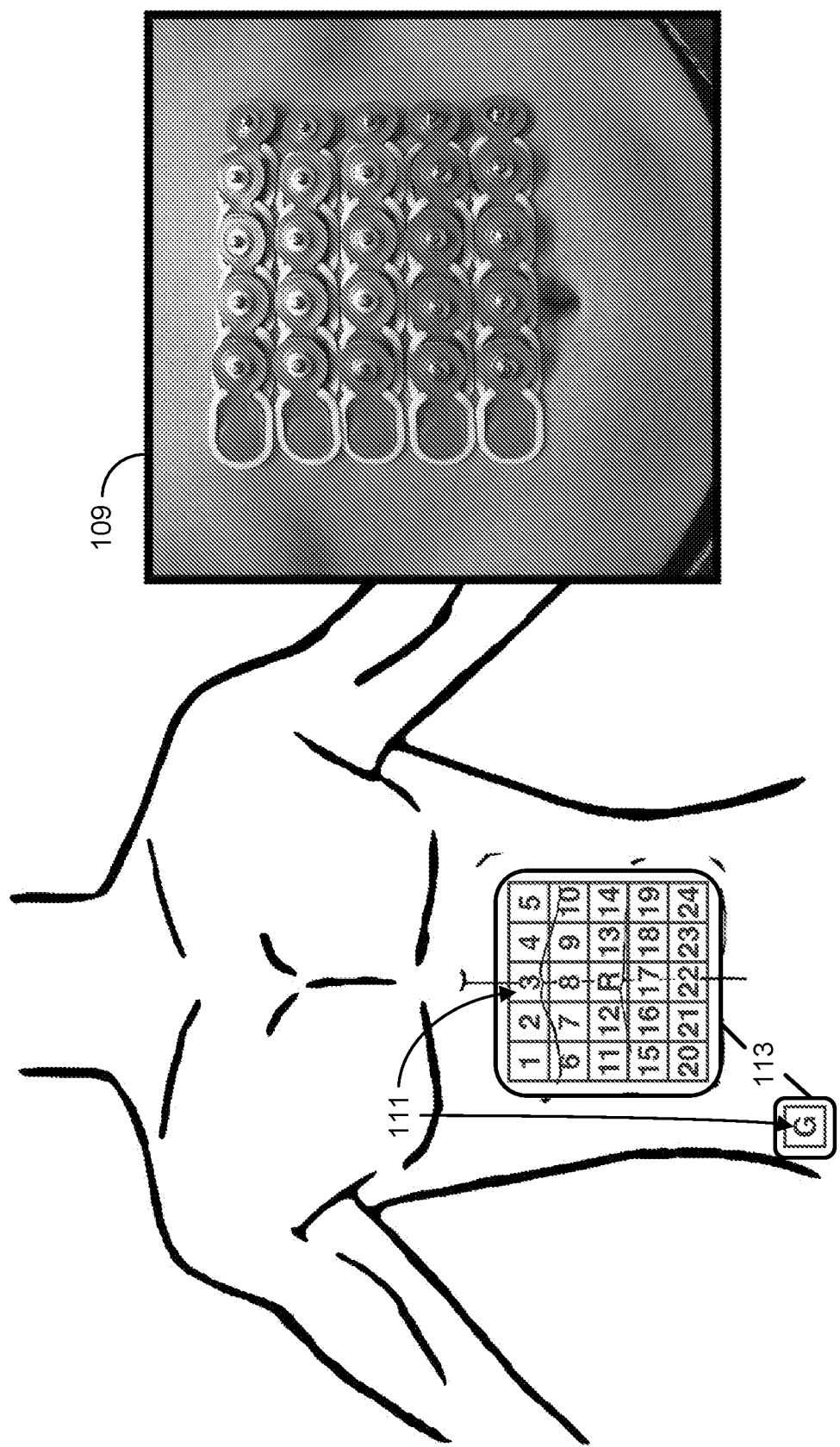
FIG. 1D shows a diagram of an example embodiment of an electrode array.

FIG. 1D shows a diagram of an example embodiment of the electrode array 111 in accordance with the present technology. In this example, the electrode array 111 is configured as a five by five electrode array (e.g., 25 electrodes, labeled in the diagram of FIG. 1D as 1, 2, 3, 4, 5, 6, 7, 8, 9, 10, 11, 12, R, 13, 14, 15, 16, 17, 18, 19, 20, 21, 22, 23, 24) with a ground electrode coupled to the substrate 113 and attached to the user's abdomen. In the example, the ground electrode (labeled G in the diagram) is configured on a separate substrate than the five by five electrode array, and is attached to the user's hip bone. In some implementations, the ground electrode can be designated as one of the 25 electrodes in the array. The example electrode array 111 is versatile, where any electrode of the 25 total electrodes of the example five by five array can operate as the reference electrode, and the other 24 electrodes can operate as a measurement electrode simultaneously and/or multiplexed (or 23 measurement electrodes if one of the 25 total electrodes is designated as ground). In some implementations, for example, the electrode array 111 can include one or more markings (e.g., on the substrate 113) to allow a user to properly align the electrode array 111 with certain anatomical landmarks, e.g., such as the belly button and/or xiphoid and/or rib cage, etc.

As shown in FIG. 1D, an image 109 depicts an example implementation of the electrode array 111 including an arrangement of 25 electrodes in a five by five square grid with a 2 cm center-to-center electrode distance, with each electrode having a 95 mm$^2$ measurement area on the abdominal surface of a human subject. The example array was horizontally centered on the subject's midline and the top row was positioned 5 cm below the xiphoid. In an example monitoring sequence using the example array, the middle electrode of the array was assigned as the reference and the ground electrode was placed on the right hip bone.

There are advantages to using multiple measurement electrodes, particularly for monitoring gastrointestinal function. For example, multiple measurement electrodes can provide more spatial sensing coverage of the stomach. When the electrodes are placed further from the stomach, the EGG amplitude decreases due to the attenuation of the signal as it conducts through a longer distance in the body. Since there is a significant amount of anatomical variability between subjects, by adding more sensors to cover a larger surface area, the measurement electrodes at different locations can more accurately record the electrophysiology. There is, however, a tradeoff with respect to the number of measurement electrodes in some applications. For example, an excess number of measurement electrodes may not be desirable because too many electrodes can be obtrusive, cause a subject to feel uncomfortable, and trigger unwanted subject stress that may impact GI activity. For a given target monitoring area, increasing the number of measurement electrodes beyond a certain number may also limit the practical physical size of each electrode so that the size of each electrode should be reduced to provide sufficient spacing between different electrodes. Also, smaller electrodes can have higher impedances relative to larger electrodes, and this increased impedance due to reduction in electrode size can lead to an increase in the signal noise. Currently, there is no established standard electrode placement for the EGG, perhaps due to some of these challenges. The example embodiments of the surface electrophysiological sensor unit 110 and electrode array 111, in accordance with the present technology, provides versatility that mitigates these challenges and allows for reliable and robust use in applications like GI functional monitoring.

The number and spatial arrangement of electrodes of the electrode array 111 can be configured according to a particular application of the device 100. For example, in some implementations, the electrodes can be arranged in a 5×5 grid as shown in FIG. 1D. This example configuration works well to acquire dynamic EGG data, e.g., for characterizing gastric motility, even when the location of the stomach or small intestine region such as the duodenum is not well known for a particular subject. In the array, the electrodes need to be spaced closely enough to ensure no spatial aliasing occurs, as discussed below. In some implementations, more electrodes can be used. For example, for stomach monitoring, the electrodes of the electrode array 111 are placed with reference to anatomical landmarks (e.g., the xiphoid), and electrically connected to a biopotential amplifier. Bipolar signals are recorded with a common reference and ground electrode. In some implementations where the amplifier does not have an analog filter, the signals can be recorded at 250 Hz or higher. In some implementations that include the amplifier having an analog filter, for example, the electrophysiological signals can be recorded at a sampling frequency of as low as 1 Hz.

Figure 1F:
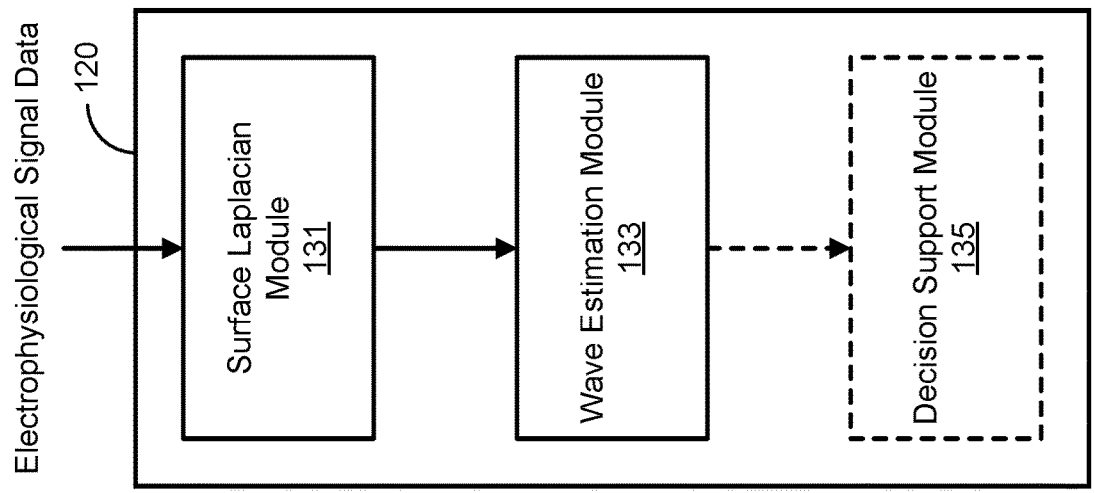
FIG. 1F shows a diagram of example data processing modules in some embodiments of the data processing unit.
Figure 1E:
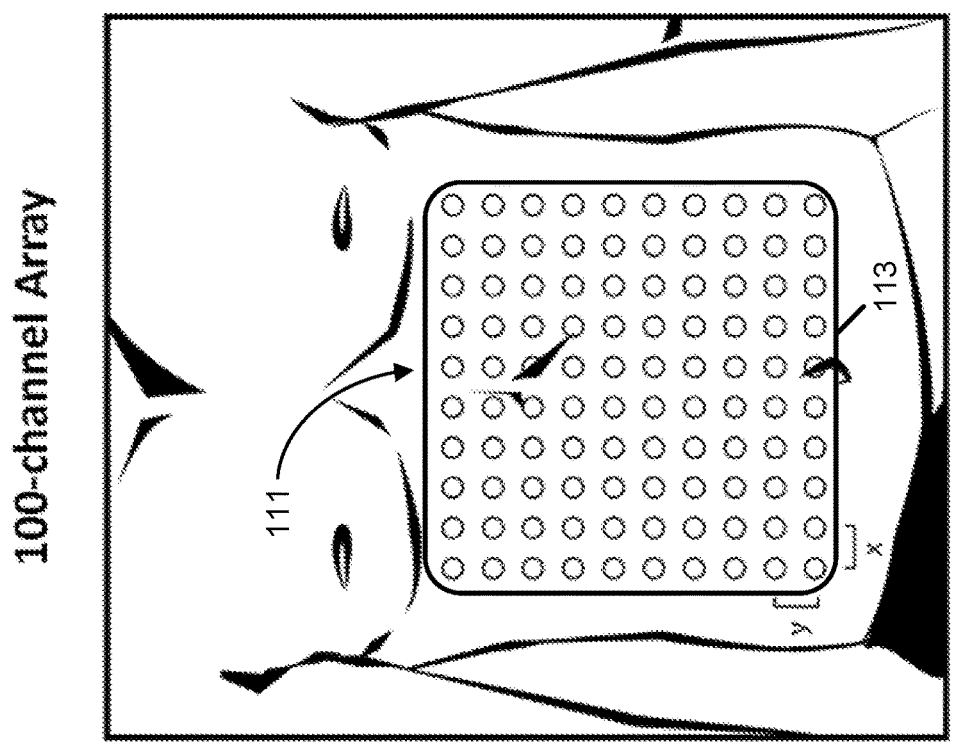
FIG. 1E shows a diagram of another example embodiment of an electrode array.

FIG. 1E shows a diagram of another example embodiment of the electrode array 111 in accordance with the present technology. In this example, the electrode array 111 is configured as a ten by ten electrode array (e.g., 100 electrodes) coupled to the substrate 113 and attached to the user's abdomen. In the example 100-electrode array, the ground electrode can be configured as one of the 100 electrodes or on a separate substrate than the ten by ten electrode array that could be attached to another part of the user's body, e.g., the user's hip bone (not shown). The example 100-electrode array 111 is versatile, where any electrode of the 100 total electrodes of the example ten by ten array can operate as the reference electrode, and the other 99 electrodes can operate as a measurement electrode simultaneously and/or multiplexed (or 98 measurement electrodes if one is designated as ground). In some implementations, both the reference and ground electrodes can be separate from the electrode array. In some implementations, for example, the electrode array 111 can include one or more markings (e.g., on the substrate 113) to allow a user to properly align the electrode array 111 with certain anatomical landmarks, e.g., such as the belly button and/or xiphoid and/or rib cage, etc.

In some implementations, the electrode array unit includes a flexible electronics patch with built in amplifier, wireless transmission, and storage capabilities. For example, the surface electrophysiological sensor device 100 can include flexible electronics in which the electrode array, in various configurations, and/or signal conditioning unit components are fabricated on a single adhesive patch that is mountable on the skin. In various embodiments, the flexible electronics, such as the electrode array 111 or Laplacian electrode array 211, can be manufactured to allow for extremely small feature sizes. Flexible electronics fabrication techniques can be used to make the array of electrodes of any diameter on a single adhesive patch. Since the patch is flexible and stretchable, it adheres better to the contours of the skin compared to conventional rigid electrodes, which can result in improved electrode impedance. As such, for the same target impedance, the electrode array for a given array footprint can have individual electrodes with a smaller diameter. That is, a higher number of electrodes per unit area can be employed by the sensor device. This can result in higher density recordings that can provide greater spatial resolution.

In some implementations, the data processing unit 120 includes data processing modules to process the acquired electrophysiological signals from the electrode array 111 and produce data that quantitatively characterize electrophysiological function of the biological system, tissue or region being interrogated by the device 110, such as the gut. In some implementations, the data processing unit 120 receives pre-processed signal data from the signal conditioning unit 115, in which the pre-processed signal data is filtered and/or digitized (e.g., by a biopotential amplifier of the signal conditioning unit 115). The data processing unit 120 processes the received signal data using data processing algorithms, which can be associated with the data processing modules, to remove artifacts from the signal data and determine properties of the electrophysiological function, such as the spatial propagation of a gastric slow-wave across time.

FIG. 1F shows a diagram of example data processing modules in some embodiments of the data processing unit 120. In some embodiments, the data processing modules include software code including algorithms that are executable by the processor 121 and stored in the memory 122. In the example shown in FIG. 1F, the data processing unit 120 includes a Surface Laplacian module 131. The obtained electrophysiological signal data from the sensor unit 110 (e.g., the pre-processed data from the signal condition unit 115, such as a biopotential amplifier) are inputted to the Surface Laplacian module 131. For example, if a 5×5 array of electrodes are used, this would include 25 time-series. The surface Laplacian module produces a surface Laplacian estimate (data set) as described herein. In some embodiments, the system can employ other software-based methods to estimate the surface Laplacian.

In some implementations, for example, the acquired EGG signals can be down-sampled to 5 Hz and band-pass filtered between 0.015 and 0.15 Hz by the signal conditioning unit 115, e.g., prior to providing to the Surface Laplacian module 131. Artifact removal can also occur prior to the Surface Laplacian module 131. Examples of signal artifacts in the acquired electrophysiological signals include motion, other bio-potentials (e.g., respiration, heart, etc.), electrical noise, etc. Blind source separation techniques such as independent component analysis or second-order blind identification (SOBI) algorithms can be used. In some examples, if the acquired electrophysiological signals have not been down-sampled and filtered by the amplifier prior to providing to the Surface Laplacian module 131, raw data can be provided to the Surface Laplacian module 131 and signal conditioning (e.g., down-sampling and/or filtering) can be done after the Surface Laplacian module 131.

The data processing unit 120 includes a Wave Estimation module 133. In some implementations, the estimated surface Laplacian time-series is inputted to the Wave Estimation module 133. For example, the surface Laplacian estimate from the example 25 time-series input (of the 5×5 array of electrodes of the sensor unit 110) would include 9 time-series provided to the Wave Estimation module 133. The Wave Estimation module 133 assesses the phase difference between electrodes of known locations to estimate the wave propagation direction and speed along with uncertainty information of the underlying wave. For example, if the stomach location is not known and the electrodes are not placed properly, i.e., in known locations with respect to an anatomical reference location, the magnitude of the signal at individual electrodes can be used to assess regions of body where greater signal concentration and/or signal source are produced. This information can be used to provide a signal strength and/or directionality map of the subject's body monitored by the electrode array. Moreover, the device can analyze the obtained data to assess the areas where the signal is concentrated and/or propagates from, including areas of the subject's body that may not have been covered by electrode array by interpolation from the processed data obtained by the applied electrode array. Such information, for example, can be used to provide a suggestion to the user to shift the array a specified distance on the abdominal surface, e.g., thereby providing a type of "error correction". Examples of wave estimation processing by the Weave Estimation module 133 can be done in multiple ways, as described herein.

In some embodiments of the data processing unit 120, for example, the data processing unit includes a Decision Support module 135. In some implementations, the Decision Support module 135 can receive the estimated spatial parameters, which can include but are not limited to, wave propagation speed and direction along with an uncertainty value associated with each parameter. The Decision Support module 135 can process the estimated spatial parameters with the respective uncertainty to provide statistical information pertinent to a decision-maker. For example, if the decision maker is a clinician, this would be a probability that the gastric motility is abnormal along with its severity. Features of the abnormality can also be provided, such as abnormal retrograde propagation or slow or anterograde propagation at abnormal speed or a conduction block.

Figure 1G:
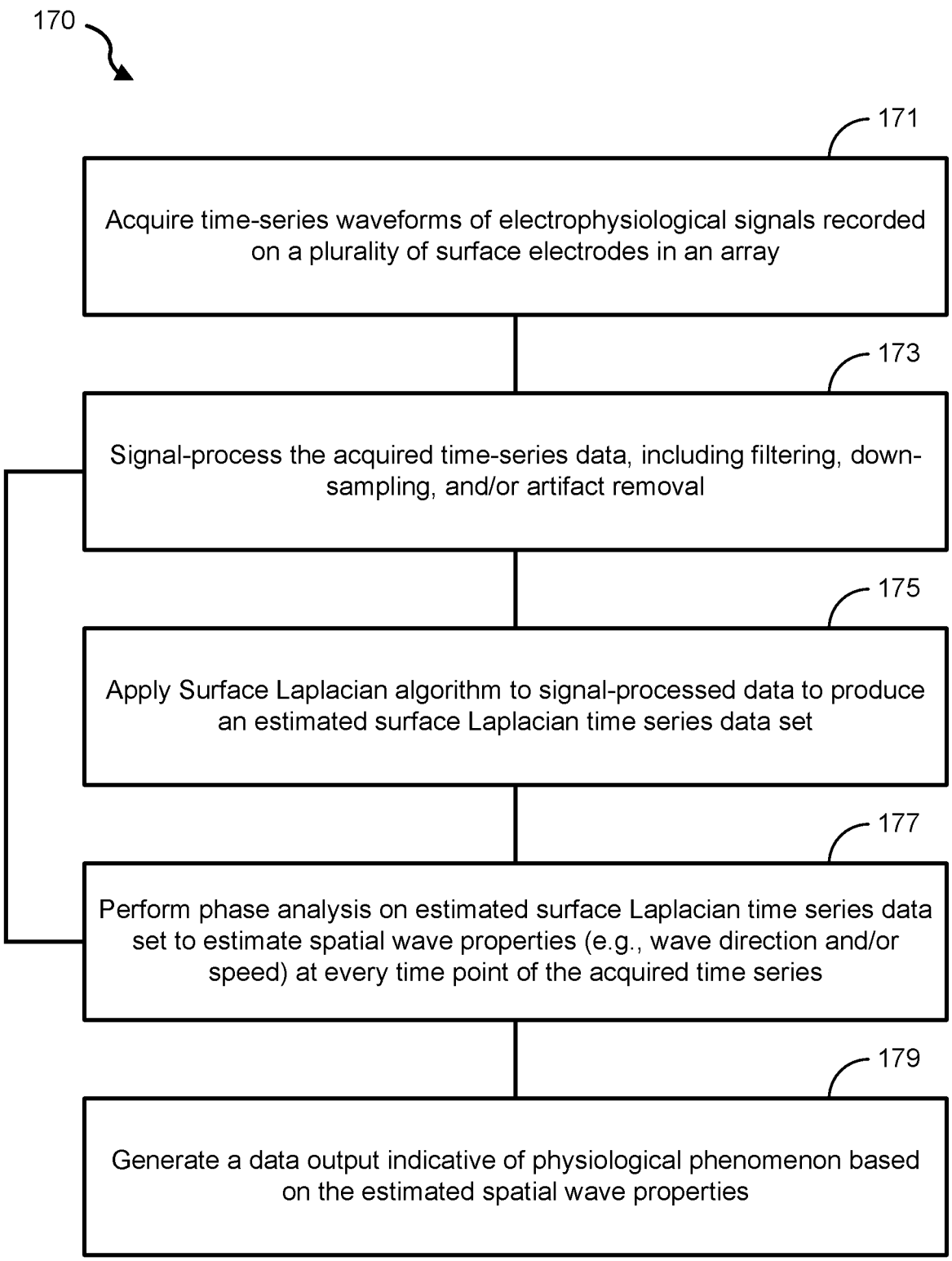
FIG. 1G shows a diagram of an example embodiment of a method for monitoring electrophysiological functions using an electrophysiological sensor device in accordance with the present technology to determine wave propagation parameters associated with the physiological function of anatomical structures.

FIG. 1G shows a diagram of a method 170 for monitoring electrophysiological functions of a subject using the electrophysiological sensor device 100 to determine wave propagation parameters associated with the physiological function of anatomical structures, e.g., including tissues, organs and organ systems. The method 170 can be implemented noninvasively, in real-time and autonomously for monitoring of spatial properties of electrophysiological signals, e.g., including directionality and source of electrophysiological signals that are associated with the physiological function of anatomical structures.

Figure 2B:
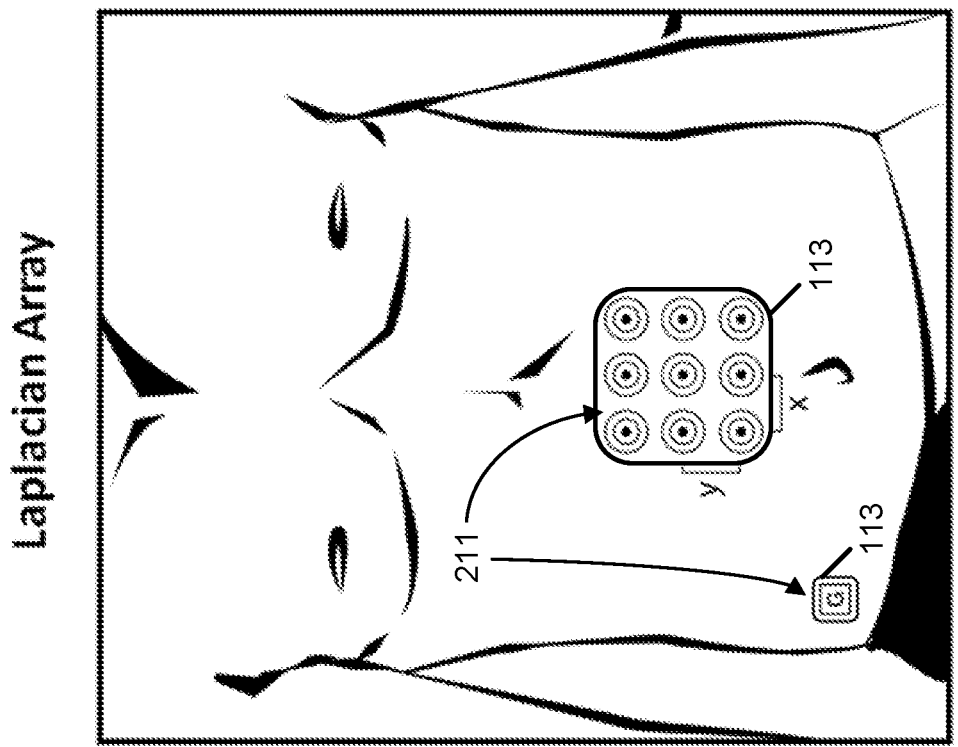
FIG. 2B shows a diagram of an example embodiment of a Laplacian electrode array.

The method 170 includes a process 171 to acquire time-series data of electrophysiological signals recorded on a plurality of surface electrodes in an array, such as the example electrode array depicted in FIGS. 1D, 1E and 2B or other examples described herein. In some implementations, for example, the process 171 can include acquiring the electrophysiological signals simultaneously on at least some or all of the electrode channels of the array. In some implementations, for example, the process 171 can include acquiring the electrophysiological signals by multiplexing the electrode channels from one or more channels concurrently at certain intervals.

The method 170 includes a process 173 to signal-process the acquired time-series data. In some implementations, the process 173 includes filtering the acquired time-series data; down-sample the time-series data, and/or remove signal artifacts from the time-series data. Example implementations of the process 173 can be implemented by the signal conditioning unit 115 and/or the data processing unit 120. For example, signal conditioning unit 115 and/or the data processing unit 120 may be configured to assemble a time-frequency representation of signals from the electrophysiological data, such as EGG data, acquired from a subject. The signal conditioning unit 115 and/or the data processing unit 120 can incorporate a digital filter that filters the acquired signal to a specific frequency band of interest. The signal conditioning unit 115 and/or the data processing unit 120 can also down-sample the data for more efficient storage and transmission. Additionally, the signal conditioning unit 115 and/or the data processing unit 120 can perform any desirable noise rejection to filter any interfering signals associated with the data.

In example implementations of the process 173, the time-series electrophysiological signal data acquired from N discrete electrodes or Laplacian electrodes are provided to a biopotential amplifier and analog-to-digital converter (ADC) used to amplify and digitize the signal from the electrodes. The total number of samples recorded is N (channels) multiplied by recording duration multiplied by sampling rate. To reduce the cost of sampling from many electrodes, a multiplexer (also referred to as a mux) can be used. The signal-processing of the data includes down-sampling (or decimating) and filtering of the data. This can be done digitally with a data processing unit (e.g., data processing unit 120 or 220) or with an analog circuit prior to the analog to digital converter. In some implementations, for example, if the data is digitized without filtering, the recording sampling rate should be sufficiently high to avoid aliasing of high-frequency components (e.g., 250 Hz). If the signal is filtered before digitizing, it can be sampled at a lower frequency directly. A low-pass filter can be used before down-sampling to avoid aliasing of high-frequency components. The data can be down-sampled to a low frequency (e.g., 5 Hz) without loss of information, since the frequency range of interest for the GI system is very low (e.g., 0.015-0.15 Hz). The sampling frequency should be at least twice the highest frequency of interest to avoid aliasing. For example, the down-sampling can be implemented to save on memory and decrease processing time of subsequent processing steps. The data can then be band-pass filtered (e.g., between 0.015-0.15 Hz), to suppress signals from irrelevant sources at other frequencies. In some implementations, if there was a lot of subject motion or movement during the recording, a signal artifact removal technique can be implemented to improve the subsequent data analysis. The example signal-processing techniques, e.g., amplifying, digitizing, down-sampling, filtering, and/or artifact rejection) can be done in any order. For example, implementing down-sampling first can be the most computationally efficient method in some situations. In some implementations, the output of the process 173, e.g., signal-processed data, is N (channels) multiplied by recording duration multiplied by reduced sampling rate.

In some embodiments, method 170 includes a process 175 to apply Surface Laplacian algorithm to the data to produce an estimated surface Laplacian time series data set. The process 175 provides a spatial filter to the time series data that emphasizes sources within the electrode array while suppressing other sources. Examples of the surface Laplacian process are described herein. In some implementations of the process 175, the output of the estimate of the surface Laplacian process includes a lower number of channel data than that of the electrode array used to acquire the data in the process 171.

In some embodiments in accordance with the disclosed technology, a surface electrophysiological sensor unit includes an array of Laplacian electrodes spatially arranged to make contact with the skin of the subject to record gut electrophysiological signals and provide the recorded signals to the data processing unit in communication with the sensor unit to analyze the data and characterize the gut electrophysiology of a subject, such as the spatial propagation of gastric waves (e.g., slow-waves) across time and space associated with the subject's gastrointestinal system. In such embodiments, for example, the process 175 is not implemented during implementations of the method 170. The signal-processed time series data acquired from the Laplacian electrode array contains the information used in subsequent data processing to produce spatial information about the underlying physiological phenomena and their source.

The method 170 includes a process 177 to perform phase analysis on the estimated surface Laplacian time series data set to estimate of spatial wave properties (e.g., wave direction and/or speed) at every time point of the acquired time series. In some implementations, the process 177 produces one estimate of the spatial wave properties from the entire array of electrodes.

The method 170 includes a process 179 to generate a data output indicative of physiological phenomenon based on the estimated spatial wave properties. In some implementations of the process 179, for example, the generated output includes one or more data plots such as a graph and/or images. Examples of the generated output are shown with respect to example implementations described herein.

Figure 1H:
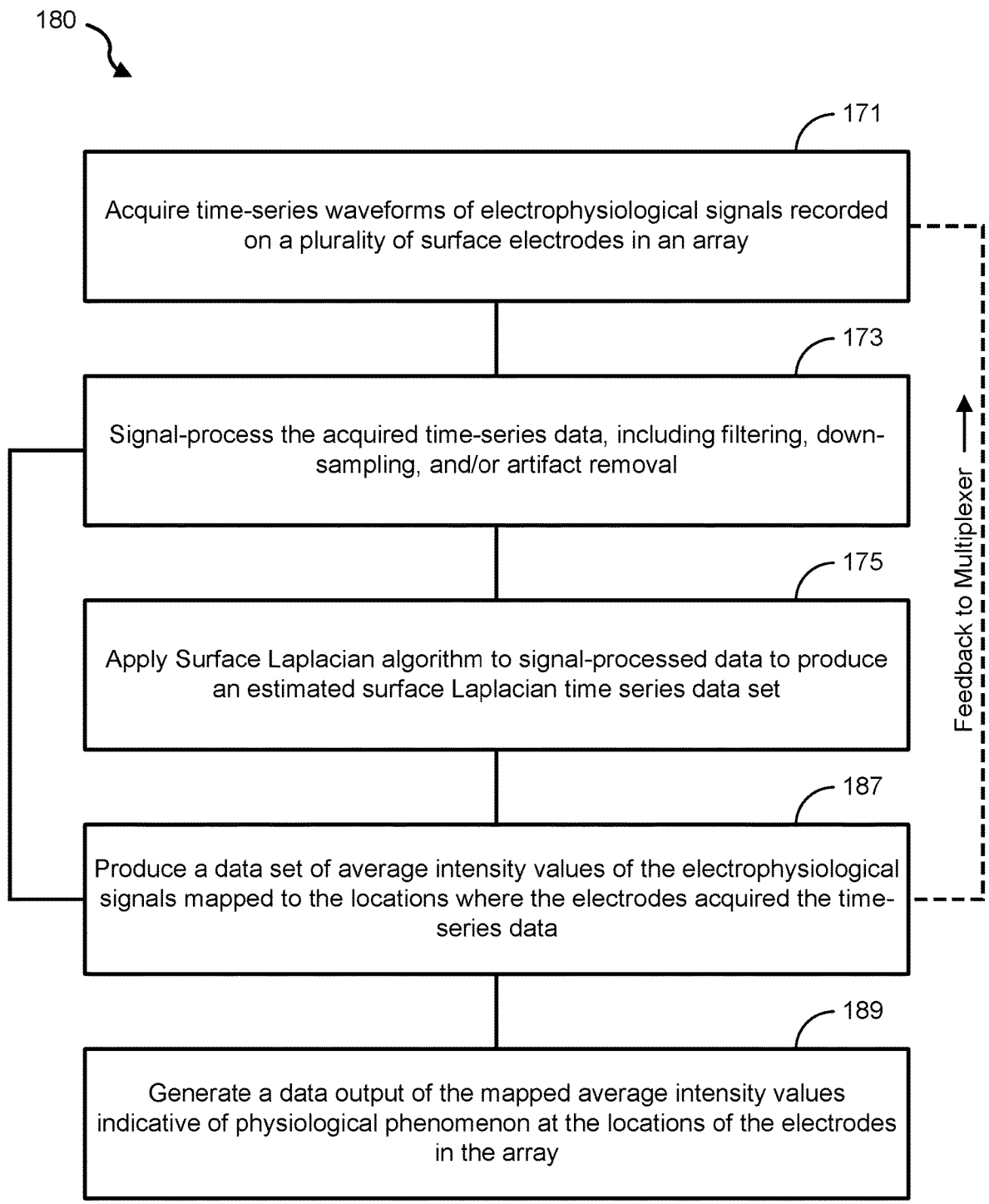
FIG. 1H shows a diagram of an example embodiment of a method for monitoring electrophysiological functions using an electrophysiological sensor device in accordance with the present technology to determine wave propagation parameters mapped to anatomical structures.

FIG. 1H shows a diagram of a method 180 for monitoring electrophysiological functions of a subject using the electrophysiological sensor device 100 to determine wave propagation parameters associated with the physiological function of anatomical structures that include map of the average electrophysiological potential over the anatomical area of recording. The method 180 can be implemented noninvasively, in real-time and autonomously for monitoring of spatial properties of electrophysiological signals, e.g., including directionality and source of electrophysiological signals that are associated with the physiological function of anatomical structures. The method 180 can include processes from the method 170 previously described.

The method 180 includes the process 171 to acquire time-series data of electrophysiological signals recorded on a plurality of surface electrodes in an array, e.g., as previously described with respect to FIG. 1G and elsewhere herein. The method 180 includes the process 173 to signal-process the acquired time-series data, e.g., as previously described with respect to FIG. 1G and elsewhere herein. Similar to the method 170 shown in FIG. 1G, in some embodiments, the method 180 includes the process 175 to apply Surface Laplacian algorithm to the data to produce an estimated surface Laplacian time series data set; whereas in embodiments of the device 100 that include a Laplacian electrode array, the process 175 may not be implemented during implementations of the method 180.

The method 180 includes a process 187 to produce a data set of average intensity values of the electrophysiological signals mapped to the locations where the electrodes acquired the time-series data. The average intensity values map can be generated from non-Laplacian or Laplacian data. In some implementations, the process 187 includes the estimated Laplacian time series data set from the results of implementing the process 175, or Laplacian time-series data from signal-processed time series signals acquired from a Laplacian electrode array. In some implementations, the process 187 includes the signal-processed time-series data from the results of implementing the process 173. For example, the signal-processed data from the array of electrodes can be used to generate a surface potential map that can be used to localize the functional activity of the anatomical structure(s), such as GI activity of the stomach and/or intestines.

In the non-Laplacian case, for example, the data from the array can be subtracted from each electrode to make that electrode the new reference. To generate the average intensity values map, also referred to as the "heat map", the process 187 re-references to each electrode and calculates the average power in the frequency range of interest (e.g., throughout the entire recording or a part of the recording) with respect to all other electrodes of the electrode array.

In the Laplacian case, such as the result from implementing the process 175 or using Laplacian electrodes in the process 171, for example, the average power in the frequency range of interest (e.g., throughout the entire recording or a part of the recording) can be directly calculated for each electrode without re-referencing. Both these approaches produce a single value for each electrode throughout the recording portion of interest (e.g., the entire recording or part of the recording).

In some implementations of the method 180, such as real-time processing during electrophysiological signal recordings of the process 171, the information from the average intensity values map (e.g., also referred to as the surface potential map) from the process 187 can be fed back into a multiplexer associated with the sensor unit to sample from only certain electrodes of interest. For example, such implementations can reduce the memory, bandwidth, and processing costs of the system.

The method 180 includes a process 189 to generate a data output of the mapped average intensity values indicative of physiological phenomenon at the locations of the electrodes in the array. In some implementations of the process 189, for example, the generated data output includes one or more data plots such as a graph and/or images that illustrate the average intensity values overlaid over the regions where the anatomical structures are in the body of the subject. Examples of the generated data output (e.g., heat map) are shown with respect to example implementations described herein.

Figure 2A:
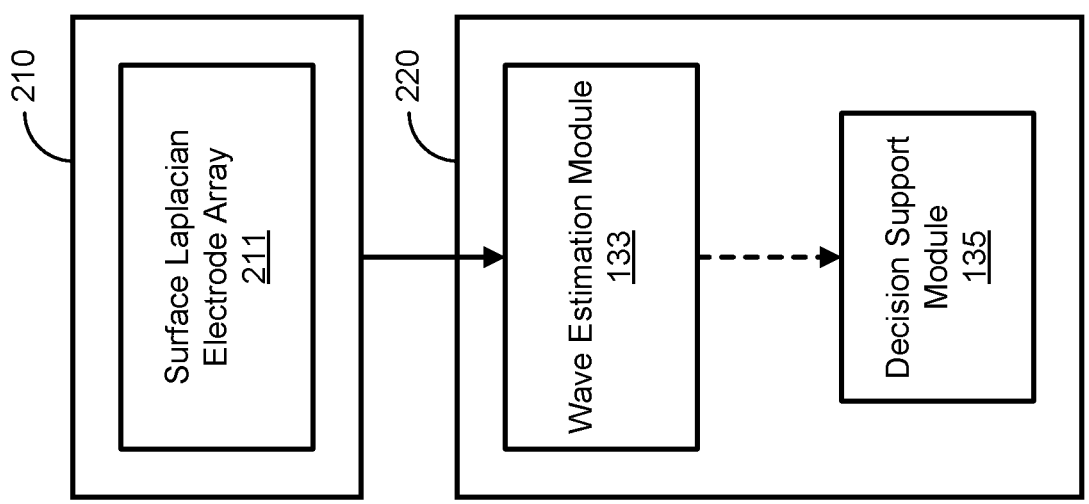
FIG. 2A shows a block diagram of an example system for monitoring electrophysiological data obtained by a wearable sensor device in accordance with the present technology that includes an array of Laplacian electrodes.

FIG. 2A shows a block diagram of an example system for monitoring electrophysiological data obtained by a wearable sensor device, such as the device 100, that includes an array of Laplacian electrodes 211 spatially arranged according to a particular design. For example, in some implementations, the Laplacian electrode array 211 can be configured as a 3×3 Laplacian electrode array, which can produce similar results to those described below associated with the example implementations of the various embodiments of the device 100, including the example 5×5 electrode array shown in FIG. 1D. If the stomach location/direction is known (e.g., through some type of imaging technique), a minimum of three Laplacian electrodes placed along the longitudinal axis of the stomach can be able to estimate the speed and presence of a wave along with information about retrograde versus anterograde propagation.

As shown in FIG. 2A, the array of Laplacian electrodes 211 are included in a surface electrophysiological sensor unit 210, which can also include the signal conditioning unit 115, the output unit 117 and the power supply 119 as previously described. For example, the surface electrophysiological sensor unit 210 can include a biopotential amplifier to process the recorded electrophysiological signals from the Laplacian electrodes to produce signal data, e.g., filtering and/or digitizing the signals. In some implementations, the Laplacian electrodes are spaced closely enough to ensure no spatial aliasing occurs. Electrodes are placed with reference to anatomical landmarks (e.g., the xiphoid) and connected to the biopotential amplifier. Unlike the example electrode array 111, such as that shown in FIG. 1D, each Laplacian electrode of the Laplacian electrode array 211 can directly provide local potentials. In some implementations where the amplifier does not have an analog filter, the signals can be recorded at 250 Hz or higher. In some implementations that include the amplifier having an analog filter, for example, the electrophysiological signals can be recorded at a sampling frequency of as low as 1 Hz.

As shown in FIG. 2A, the data processing modules of a data processing unit 220 that is in communication with the sensor unit 210 includes the Wave Estimation module 133 without the Surface Laplacian module 131. For example, the surface Laplacian does not have to be estimated by the data processing unit 220 in implementations of the system of FIG. 2A. In such implementations, the electrophysiological signals recorded by the Laplacian electrodes, e.g., pre-processed the biopotential amplifier, are inputted to the Wave Estimation module 133. The data processing unit 220 can include the processor 121, the memory 122 and/or I/O unit 123 and/or wireless communications unit 125, like that shown in FIG. 1C. In some embodiments of the system shown in FIG. 2A, the data processing unit 220 includes the Decision Support module 135. In implementations, for example, the Decision Support module processes the estimated spatial parameters to produce statistical information about the measured electrophysiological signals, e.g., such as probability or weights associating gastric motility with degrees of normalcy or abnormality and severity, which can empower a decision-maker to make diagnoses about the health of the subject and/or treatment recommendations that can be targeted to the measured physiological phenomenon, as opposed to only symptomatic effects.

FIG. 2B shows a diagram of an example embodiment of the Laplacian electrode array 211 in accordance with the present technology. In this example, the Laplacian electrode array 211 is configured as a three by three Laplacian electrode array (e.g., 9 electrodes) coupled to the substrate 113 and attached to the user's abdomen. In the example, a ground electrode (labeled G in the diagram) is configured on a separate substrate than the three by three Laplacian electrode array, and is attached to the user's hip bone. In some implementations, the ground electrode is on the same substrate 113 as the Laplacian electrodes. In some implementations, for example, the Laplacian electrode array 211 can include one or more markings (e.g., on the substrate 113) to allow a user to properly align the Laplacian electrode array 211 with certain anatomical landmarks, e.g., such as the belly button and/or xiphoid and/or rib cage, etc.

For example, the surface Laplacian is essentially the second spatial derivative of the potentials on the body surface. This can be estimated from discrete electrodes, or the electrodes themselves can be designed to measure the potentials on the body surface directly, i.e., Laplacian electrodes. Laplacian electrodes can be designed with concentric rings to achieve such measurements. For example, designs of Laplacian electrodes include a bipolar concentric ring electrode which can estimate the surface Laplacian directly through a five-point method, and a tripolar concentric ring electrode that can estimate the surface Laplacian directly through a nine-point method. The example Laplacian electrode array 211 includes nine tripolar concentric ring electrodes arranged in a three by three array, as shown in FIG. 2B. Compared to discrete electrodes, for example, Laplacian electrodes have been shown to have significantly better spatial selectivity and signal-to-noise ratio. The dimensions of the electrodes, for example, such as the diameter and thickness of the rings, can be optimized for a signal of interest.

In some implementations of the electrophysiological sensor device 100, for example, the surface Laplacian provides better spatial resolution by emphasizing superficial localized sources, while suppressing deep sources or ones that are widespread and coherent. The methods disclosed can be completely automated and configured to require no user input (i.e., no human bias). In some implementations, for example, a spatial estimate is produced at every time point. Conventional frequency based methods typically use 4 minute windows of data since the signal is so slow (e.g., 0.05 Hz) and may miss out on abnormal occurrences at slower time-scales. The methods in accordance with the disclosed technology are robust to motion artifact. For example, only sustained waves are extracted, which are unlikely to occur by chance or from motion.

Methodology of Spatial Sampling

For using surface electrodes to accurately map acquired electrophysiological potentials acquired on the abdominal surface, the layout and size of the electrodes need to be considered. The abdominal surface potential is a continuous field that is discretely sampled at each electrode location. The recorded potentials are a smeared version of the current sources generated on the stomach surface. For example, this can be due to the conduction of the signal through the tissue (e.g., fat, muscle, and skin) separating the electrodes and the source. While volume conduction limits the spatial resolution of EGG compared to serosal recordings, for example, it makes it feasible to discretely sample the abdominal potentials. The separating tissue acts as a natural anti-aliasing spatial filter, enabling accurate sampling of the potentials with a reasonable number of electrodes.

The discrete sampling of continuous time-series data has been well-characterized. The key concept is the Nyquist criterion, which states that for lossless digitization, the sampling rate should be at least twice the maximum frequency (e.g., $f_s > 2f_{max}$, where $f_s$ is the sampling rate and $f_{max}$ is the maximum frequency of the signal). Once a time series has been aliased, there is no signal processing technique that can recover the lost information.

The Nyquist criterion for temporal sampling also applies to spatial sampling. The density and measurement area of the electrodes dictate the highest spatial frequency that can be detected without spatial aliasing. The electrode averages the potentials within the region that is in contact with its measurement area. In other words, the electrode is an analog filter that eliminates spatial frequencies with wavelengths shorter than its measurement diameter. For example, consider an array of electrodes that have uniform center-to-center spacing d and electrode diameter D. Applying the Nyquist criterion to the edge-to-edge distance between neighboring electrodes results in the following constraint:

$$d - D < \frac{\lambda_{min}}{2} \quad (1)$$

where $\lambda_{min}$ is the shortest spatial wavelength of the signal.

The electrode spacing and measurement area is determined by a lower bound for the spatial wavelength of the cutaneous wave, which can be estimated by considering its slowest speed and highest frequency (λ=speed/freq). For example, it is assumed that the slowest physiological serosal and cutaneous speeds are equivalent. After applying the appropriate values, e.g., for healthy subjects is approximately 1.5 mm/s, 0.06 Hz, the minimum spatial wavelength ($\lambda_{min}$) of the cutaneous wave can be calculated to be 25 mm. Therefore, to ensure that no spatial aliasing occurs, the edge-to-edge distance between electrodes should be less than 12.5 mm ($\lambda_{min}/2$). In some implementations, an electrode diameter D of 11 mm is selected with a center-to-center spacing d of 20 mm, which results in an edge-to-edge distance of 9 mm to satisfy this condition.

Methodology of Surface Laplacian

Biopotentials can be recorded with a differential amplifier, where the desired signal appears as a voltage between two input terminals. Differential amplifiers are able to reject the common mode signal from various sources of interference, yielding improved signal quality. A consequence of this recording scheme is that the local potentials are not accurately depicted. The surface Laplacian can provide a more realistic representation of local source distributions compared to conventional bipolar recordings by removing the effects of the reference electrode and eliminating volume conducted signals from distant regions. The surface Laplacian has previously been applied for ECG mapping to provide better spatial resolution and resolve depolarizations in different regions of the heart. The surface Laplacian has also been shown to be more robust to ECG and respiratory interference when recording the small intestine electrical activity.

The surface Laplacian is the second spatial derivative of the surface potential estimated on the surface of a geometry that passes through the electrode locations. For a voltage on a planar surface, it is defined by the expression:

$$\nabla_S^2(\Phi_S) = \frac{\partial^2 \Phi}{\partial x^2} + \frac{\partial^2 \Phi}{\partial y^2} \quad (2)$$

A simple nearest-neighbor method of estimating the surface Laplacian of EEG data was first published in 1975 by Hjorth. This original approach used a finite-difference approximation for the second spatial derivative of the scalp potential by averaging potential differences between a central and four surrounding electrode locations. Although there have been many advances since that seminal paper, the finite-difference approximation is not practical or easy to implement for certain applications.

Figure 3:
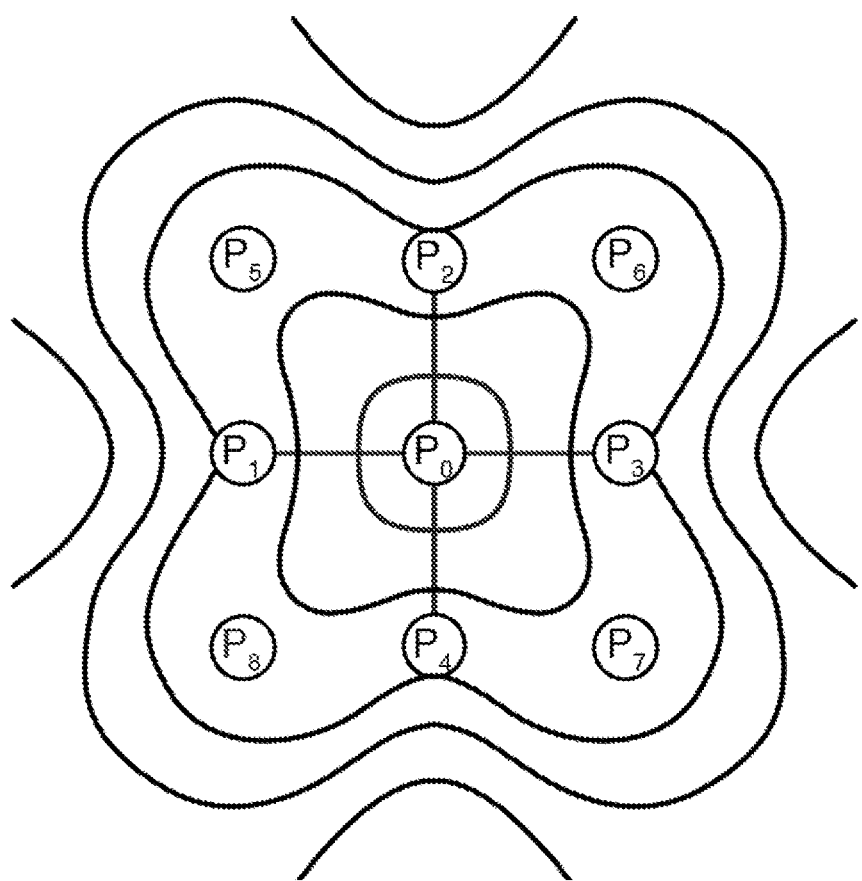
FIG. 3 shows an example diagram used to illustrate eight neighboring electrodes that are used to calculate the finite-difference surface Laplacian.

In one example of the present methodology, eight electrodes are positioned radially with respect to the central electrode position. Involving a larger number of electrodes improves the possibility of obtaining a good approximation. Before averaging, the potential difference is divided by the corresponding electrode distance in order to represent the gradient. This is calculated using the following equation:

$$v_0 = P_0 - 0.15(P_1 + P_2 + P_3 + P_4) - 0.1(P_5 + P_6 + P_7 + P_8) \quad (3)$$

where, $P_0$ is the potential measured at the central electrode, and $P_1$ to $P_8$ are the potentials measured at the radially neighboring electrodes, as shown in FIG. 3.

FIG. 3 shows an example diagram used to illustrate eight neighboring electrodes that are used to calculate the finite-difference surface Laplacian. The source activity is within a measurement area centered at electrode $P_0$. The weighting coefficient for each of the surrounding electrodes is proportional to the reciprocal of its distance to the center electrode. The method described by Equation (3) was used as a pre-processing step before the estimation of wave propagation.

The surface Laplacian resolves the reference issue and yields local potentials that can be used to estimate wave propagation. The signal recorded at an electrode position is a spatial average of the active current sources within the volume. The signal depends on several factors, including the volume geometry and conduction properties, as well as the location of the reference electrode. Each current source contributes to the signal based on its orientation, strength and electrical distance to the electrode. Two nearby electrodes record similar signals since they record the average activity in overlapping volumes of tissue. The surface Laplacian effectively reduces the volume that each electrode averages, culminating in improved spatial resolution. The surface Laplacian emphasizes superficial localized sources, while suppressing deep sources along with shallow sources that are widespread and coherent. This property allows for detection of gastric slow-wave propagation from the abdominal surface, and for determination of spatial and/or temporal propagation properties associated with the detected gastric slow-wave.

In some aspects of the present technology, a surface Laplacian is implemented in software by the Surface Laplacian module 131 of the data processing unit 120 based on the electrophysiological signal data obtained from a multi-electrode array to quantitatively characterize electrophysiology of gastrointestinal function. Additionally, or alternatively, the surface Laplacian can be implemented in hardware, for example as depicted in FIG. 2A, using certain geometric electrodes and pre-amplification at the location of each triple of electrodes. Implementations of embodiments in accordance with the disclosed systems and methods can determine how reliable spatial information about gastric function can be accurately acquired, e.g., when the spacing meets the aforementioned criteria.

Examples of Wave Estimation

In consideration of a realistic, multi-scale model of EGG, coherent spatial propagation of the surface potential was expected in healthy subjects. A technique developed to compute the 2D component velocity from image sequences was implemented to estimate features of stomach wave propagation on the abdominal surface. By using a data-driven approach that evaluates the temporal evolution of spatial contours of constant phase, strong underlying assumptions are not made of the spatial properties of the cutaneous potentials.

There may be concern that propagation of the potential from the source to the electrode may lead to phase delays that distort the estimated wave parameters. A quasi-static assumption can be made to describe the potential field in the human body. Since the capacitive component of the tissue impedance is negligible in the frequency range of internal bioelectric events, electromagnetic propagation effects can be neglected. This allows us to make true gastric slow-wave speed estimates.

Disclosed herein is a framework which forms the basis of an example wave estimation algorithm in accordance with the present technology. The Hilbert transform is applied to the surface Laplacian estimate at each electrode location (x, y), resulting in a characterization of instantaneous amplitude $\alpha(x, y, t)$ and phase $\varphi(x, y, t)$:

$$V(x,y,t)+iHb[V(x,y,t)]=\alpha(x,y,t)e^{i\varphi(x,y,t)} \quad (4)$$

In biological signals, contours of constant phase provide a better approximation to the motion field compared to those of constant amplitude, since the amplitude of the signal is proportional to the distance of the recording electrode to the source. Surfaces of constant phase satisfy the equation:

$$\varphi(x,y,t)=c, c\in \mathbb{R} \quad (5)$$

By assuming that the constant phase surfaces move along the motion field, the phase with respect to time can be differentiated using the total derivative:

$$\frac{d\varphi}{dt} = \nabla\varphi \cdot v + \frac{\partial\varphi}{\partial t} = 0 \quad (6)$$

where $\nabla\varphi$ is the spatial gradient of the instantaneous phase, $$V = \left(\frac{dx}{dt}, \frac{dy}{dt}\right)$$

is the wave velocity, and "•" represents the dot product operator. Since the phase gradient is parallel to the velocity direction, the speed can be calculated as:

$$\text{speed}(t) = \|v(t)\| = \frac{\left|\frac{\partial\varphi}{\partial t}\right|}{\|\nabla\varphi\|} \quad (7)$$

where for any $z \in \mathbb{R}^n$, $\|z\|$ represents the 2-norm and $\bar{z}$ indicates the spatial average (i.e., across all electrodes) at a given time. The wave direction is then computed by:

$$\text{direction }(t)=\text{ang}(\overline{\nabla\varphi}) \quad (8)$$

where ang( ) is the element-wise arc tangent, choosing the quadrant correctly.

A quantity called phase gradient directionality, PGD (t), is defined as a measure of how well the phase gradients align across the array:

$$PGD(t) = \frac{\|\overline{\nabla\varphi}\|}{\|\nabla\varphi\|} \quad (9)$$

PGD can take on values between 0 and 1, where 0 represents phase gradients that are randomly distributed and a value of 1 signifies perfect spatial alignment.

Estimates at time points when PGD is less than 0.5 are typically ignored, since velocity is only well defined when phase gradients are coherent across the array. With a small number of sensors, it is possible that PGD can be greater than 0.5 by chance, even when a spatial wave does not exist. Independent, identically distributed (i.i.d.) white Gaussian noise on a 3 by 3 sensor array across time (e.g., no spatial wave present) was generated and the false positive rate of PGD being greater than 0.5 by coincidence was evaluated. Without an additional minimum duration constraint, up to a 50% of the samples would be considered to be a wave. By further imposing criteria that the PGD must be above 0.5 for a certain duration of time, the likelihood of false positives can be drastically reduced. A sustained wave was defined as one having a PGD greater than 0.5 for at least 2 seconds, since the false positive rate for this criteria is near zero. Values of wave propagation direction and speed in this disclosure are reported for instances that meet these criteria.

Figure 4:
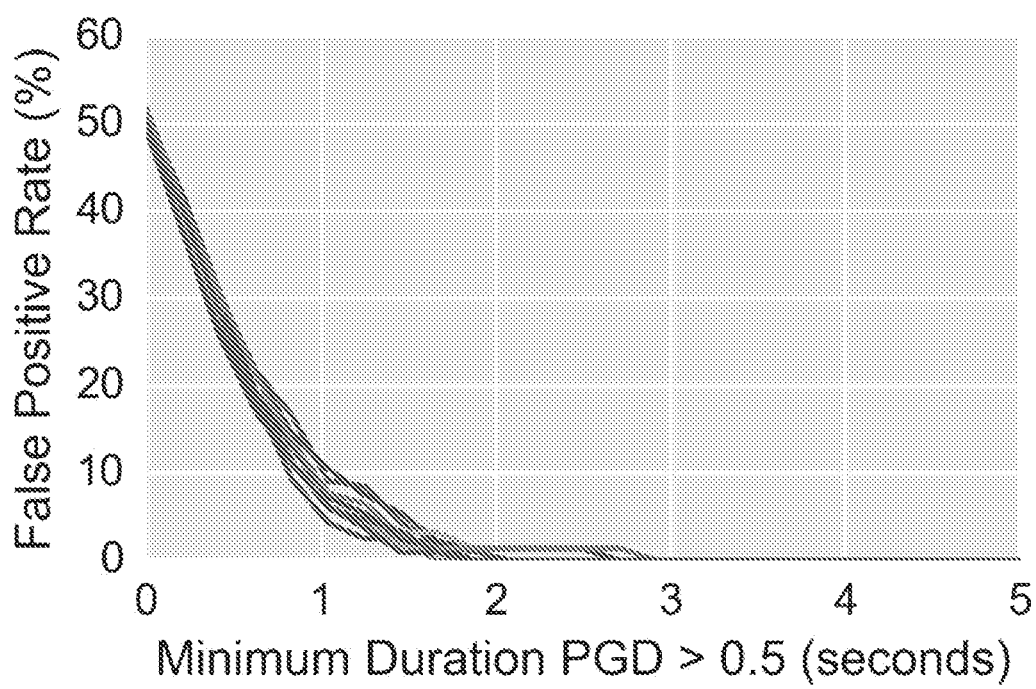
FIG. 4 shows an example data plot depicting the false positive rate of i.i.d. white Gaussian noise being classified with PGD greater than 0.5 as a function of minimum sustained wave duration.

FIG. 4 shows an example data plot depicting the false positive rate of i.i.d. white Gaussian noise being classified with PGD greater than 0.5 as a function of minimum sustained wave duration. The different lines indicate independent simulations.

The example algorithm to detect the wave propagation velocity described here essentially assesses the phase difference between electrodes at a known location. Other algorithms can also be used. For example, a zero-delay wavenumber spectrum (ZDWS) method can be implemented and similar results can be produced.

In some example implementations described herein, an array of 25 electrodes was used. With Laplacian electrodes, fewer electrodes would be required. For example, if the location and direction of the stomach was known, in theory as few as three Laplacian electrodes could be placed along the longitudinal axis of the stomach to estimate the propagation velocity.

The electrode spacing and use of the surface Laplacian can allow for the estimation of wave parameters. The disclosed methods and systems are the first to be able to produce EGG propagation velocities that are consistent with serosal slow-wave activity.

EXAMPLE IMPLEMENTATIONS

Example implementations of embodiments of the devices, systems and methods in accordance with the present technology are described. The example implementations included studies involving human subjects, as described below.

Example models used in the example implementations are described. A forward electrophysiology model of stomach was used to validate the wave estimation methodology. For simplicity, for example, circumferential propagation of the serosal slow-wave was ignored and the following 1D wave equation was solved using a finite difference approach:

$$\frac{\partial^2 u}{\partial t^2} = c(x)^2 \frac{\partial^2 u}{\partial x^2} \qquad (10)$$

where $c(x)$ is the wave speed that depends on the location on the stomach surface. Gaussian pulses with a width of 35 mm were generated every 20 seconds (0.05 Hz) in the pacemaker region of the stomach, illustrated in FIGS. 5A and 5B. The pulse width, in addition to the modulations of its speed and amplitude along the organoaxial direction of the stomach, were chosen to be consistent with a description in the literature for healthy subjects. Both the speed and amplitude were highest in the pacemaker region (6.0 mm/s, 0.57 mV), followed by a reduction in the corpus (3.0 mm/s, 0.25 mV), and finally increased in the antrum (5.9 mm/s, 0.52 mV). Mur's boundary condition was used to ensure the pulses were absorbed into the pylorus instead of being reflected back into the stomach. The Courant-Friedrichs-Lewy condition dictated the time step size to guarantee a converged finite-difference solution. The 1D serosal solution was expanded onto a 2D mesh to match a realistic geometry of the stomach, using anatomical and physiological parameters described previously.

Figure 5A:
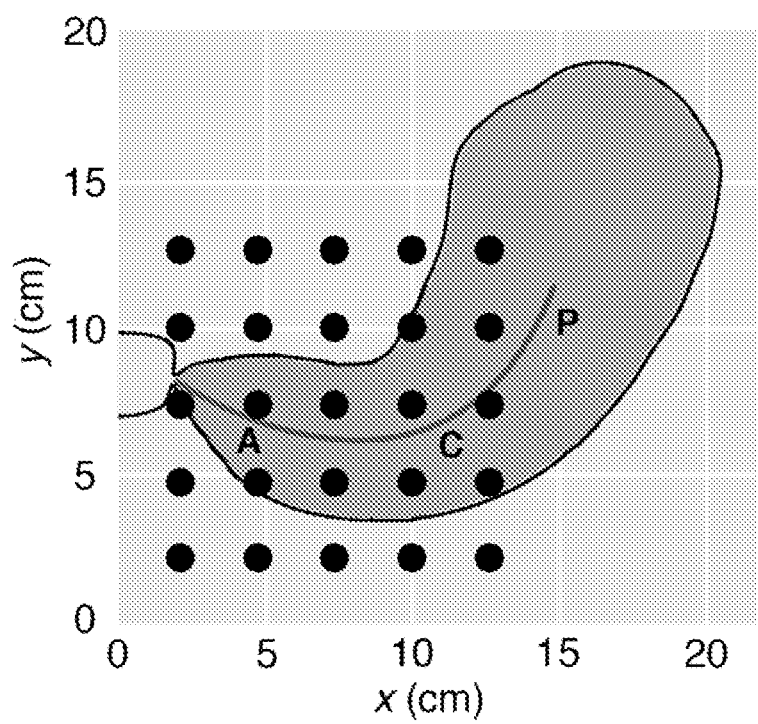
FIGS. 5A and 5B show plots depicting the stomach anatomy and its relation to an example electrode configuration used in an example forward model.
Figure 5B:
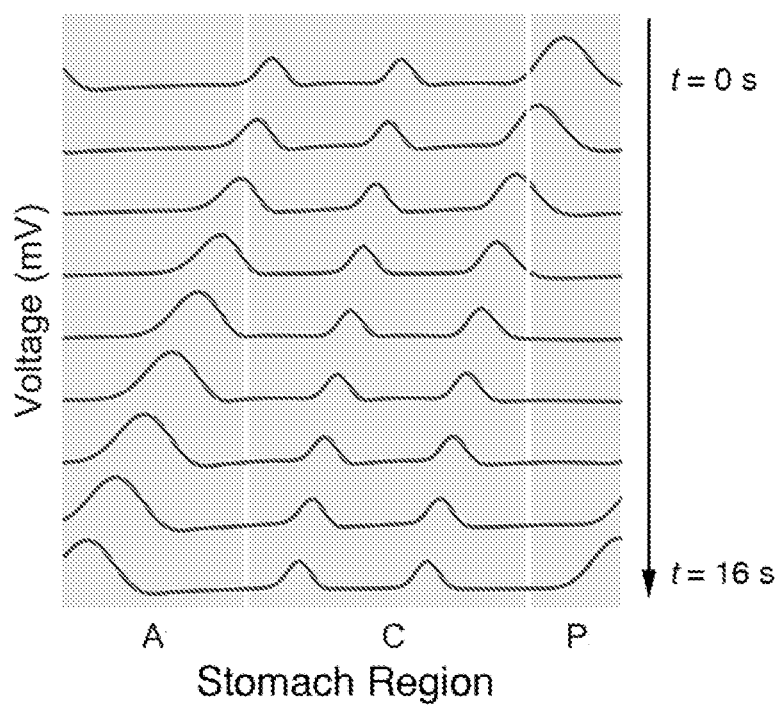

FIGS. 5A and 5B show plots depicting the stomach anatomy and its relation to an example electrode configuration used in an example forward model. FIG. 5A shows a plot of the stomach anatomy and an example electrode configuration used for the forward model. The black circles represent electrodes (e.g., configured in a 5×5 electrode array). The curved (blue) line corresponds to the location of the 1D serosal solution that is expanded to a 2D mesh to match the stomach geometry. The pacemaker (P), corpus (C), and antrum (A) regions of the stomach are labeled on the plot. FIG. 5B shows a plot depicting example time snapshots over a 16 second period for the 1D serosal solution. The pulses are generated in the pacemaker (P) region, have a decreased speed and amplitude in the corpus (C), followed by an increase of both in the antrum (A), and eventually terminate in the pylorus.

The cutaneous potentials are essentially a weighted summation of the serosal slow-wave at every time point. Due to the electrical properties of physiological systems, a quasi-static assumption can be made even though the sources are time-varying. By further assuming a volume that is linear, homogenous, and isotropic, the potential (p at a field point (x', y', z') due to a volume current source density IV (x, y, z) is given by:

$$\varphi(x', y', z') = \frac{1}{4\pi\tilde{\sigma}} \int_v \frac{I_v(x, y, z)}{r} dv \qquad (11)$$

where, $\tilde{\sigma}$ is the conductivity and $r$ is the Euclidean distance between the source point and the field point. The primed variables refer to the points on the abdominal skin while the unprimed variables are points on the stomach surface. A conductivity of 0.125 S/m was chosen, which is halfway between the mean conductivities of fat and the human trunk, the two primary constituents separating the stomach and skin. The distance $r$ depends on the stomach size and abdominal thickness, which was chosen to be 4 cm. The simulated cutaneous potentials were computed at locations that matched the experimental electrode layout (5×5 grid, 2 cm center-to-center electrode distance, 95 mm² electrode measurement area).

Example protocols and method used in the example implementations are described. Eight healthy subjects (e.g., five male, three female, age=26±4 years, BMI=22±3) without gastrointestinal symptoms or discomfort participated in the example study. Subjects were asked to fast overnight prior to the recording. Any excess abdominal hair was removed and the skin was prepped with NuPrep® to reduce electrode contact impedance. Pre-gelled Ag—AgCl electrodes with a 95 mm² measurement area were placed on the abdominal surface using anatomical landmarks for consistency between subjects. The array was horizontally centered on the subject's midline and the top row was positioned 10 cm below the xiphoid. The electrodes were arranged in a 5 by 5 square grid with a 2 cm center-to-center electrode distance, as shown in the image 109 in FIG. 1D. The middle electrode of the array was assigned as the reference and the ground electrode was placed on the right hip bone. A BrainProducts BrainAmp 32ch EEG amplifier was used to acquire the signals at a sampling rate of 250 Hz. The test meal was a 250 kcal nutrient bar (e.g., CLIF Barr: 5 g fat, 45 g carbohydrate, 10 g protein, 7 g fiber) along with 8 ounces of room temperature water. The duration of the recording was 30 minutes pre-prandial and 60 minutes post-prandial. The subjects sat in a comfortable recliner angled at 45 degrees and were asked to limit talking and bodily movement throughout the recording.

Prior to wave estimation, the signals recorded from each electrode were down-sampled to 5 Hz and then bidirectionally filtered to avoid phase distortion using a finite impulse response band-pass filter with frequency between 0.015 and 0.15 Hz. The surface Laplacian was then calculated at each interior electrode location using Equation (3).

Example results from the study in the example implementations are described.

Example simulated data results include the following. To determine if the surface Laplacian method alters the estimates of direction and speed, signals were generated using the example forward model with known parameters, as described above. The signals were subtracted from the center electrode to replicate the use of a reference electrode in the experimental recording. The surface Laplacian was then calculated and the output was used to verify that the wave-estimation algorithm can estimate the correct direction and speed.

Figures 6A, 6B, 6C, 6D:
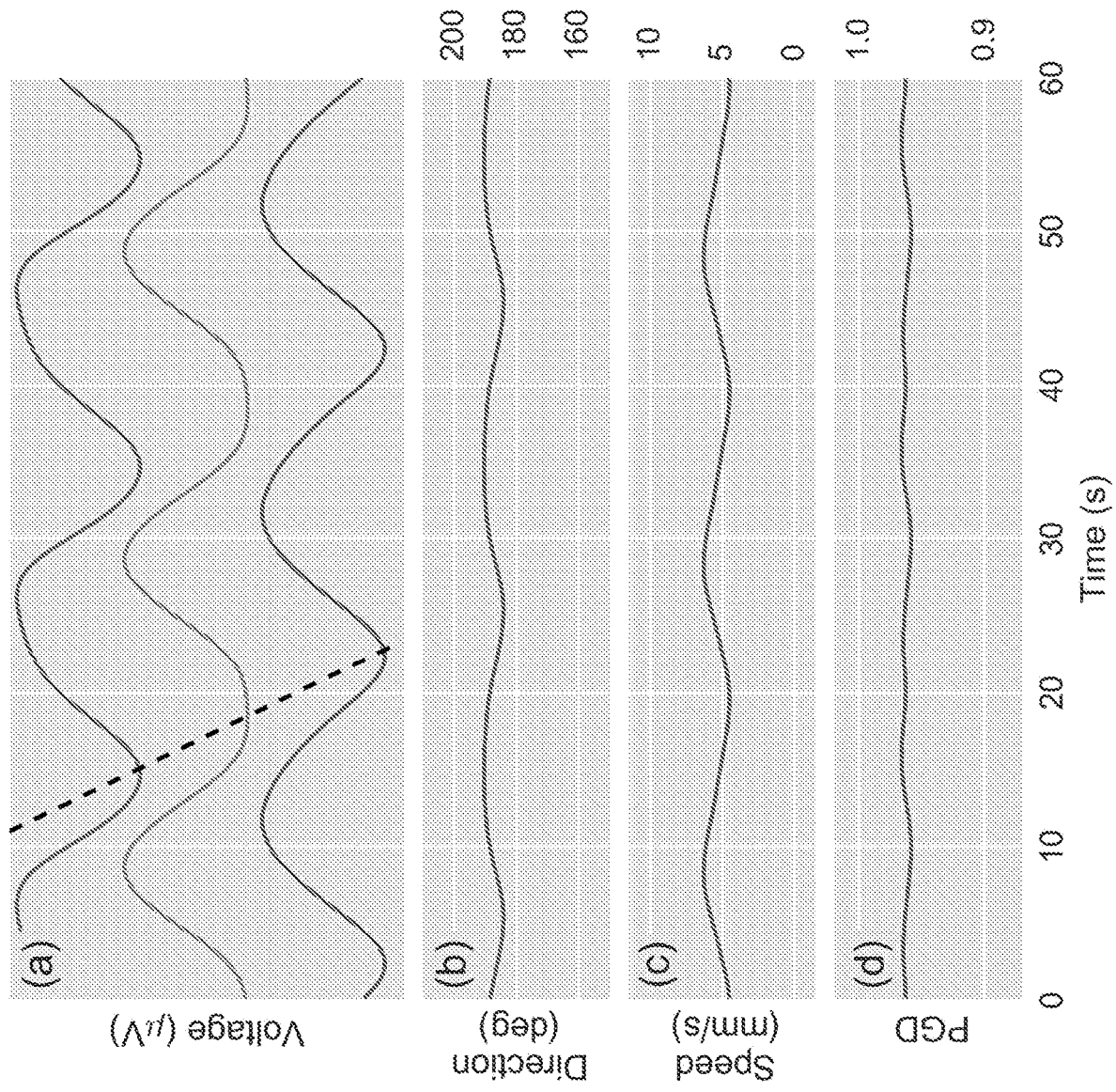
FIGS. 6A-6D show example results from a 60 second simulation of cutaneous potentials from the forward model on an example 5×5 electrode array.

FIGS. 6A-6D show example results from a 60 second simulation of cutaneous potentials from the forward model on an example 5×5 electrode array. The voltages from three select simulated electrode sites from the horizontal axis illustrate the wave propagation across the array. The wave estimation algorithm outputs direction, speed, and PGD for every time point in the simulation, which is also displayed in the figures. The average estimated direction (e.g., 187 degrees) and speed (e.g., 5.3 mm/s) match the model parameters. PGD is greater than 0.9 for all the time points, indicating near perfect spatial alignment. FIG. 6A shows a plot showing the voltage from three channels, with a dotted line illustrating wave propagation. FIG. 6B shows a plot depicting an estimate of wave direction (e.g., mean: 187 degrees), and FIG. 6C shows a plot depicting an estimate of wave speed (e.g., mean: 5.3 mm/s). FIG. 6D shows a plot depicting the PGD, which is above 0.9 throughout the simulation. For example, the time scale along the horizontal axis applies to the data plots of FIGS. 6A-6D.

Example experimental data results from the example study include the following. By generating a series of time snapshots, for example, a sample wave can be visualized. In the time series windows shown in FIG. 7, the wave originated on the right side of the array and propagated slowly to the left at a speed of approximately 4 mm/s. The snapshots display local potentials as calculated by the surface Laplacian, which are spatially interpolated for better visualization. The amplitude of the signal was about 100 μV, as indicated by the color bar.

Figure 7:
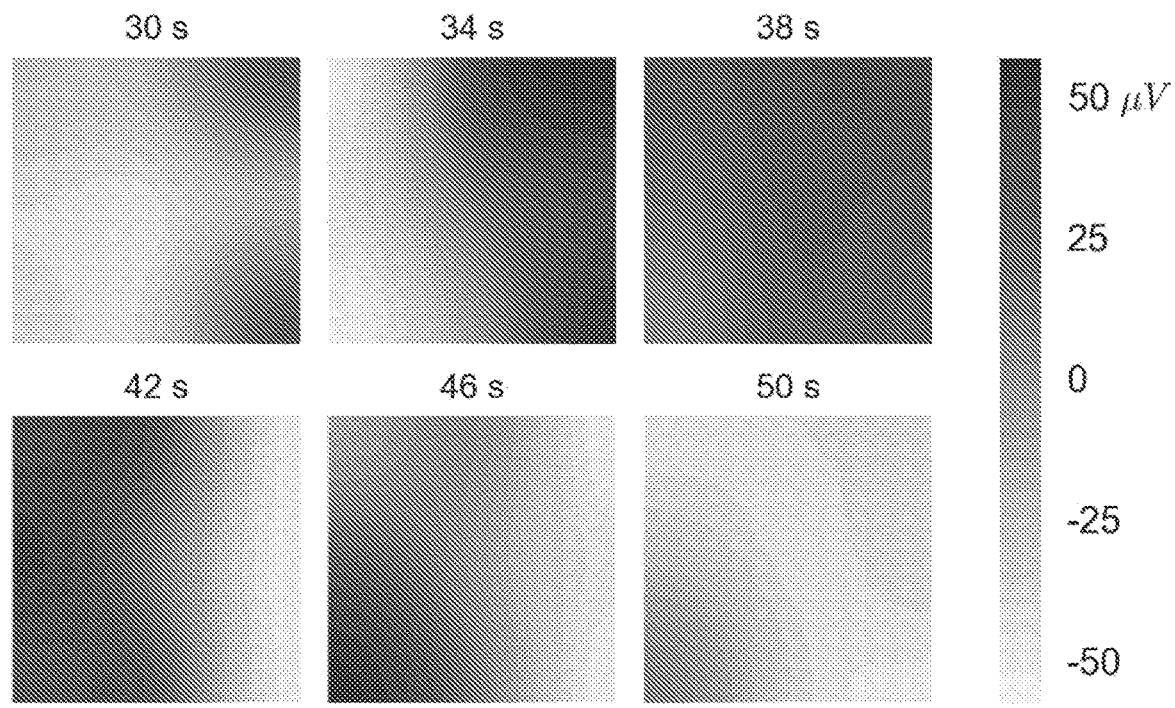
FIG. 7 shows example individual time snapshots of the voltages for a 20 second segment from a subject.

FIG. 7 shows example individual time snapshots of the voltages for a 20 second segment from subject 1. Voltage is presented in white-blue color (e.g., blue representing positive voltage) and time (in seconds) is labeled above each plot. The snapshots are interpolated for visualization purposes. This particular wave took approximately 20 seconds to propagate across the array at about 180 degrees relative to the positive x-axis.

A two-minute segment of the surface Laplacian time series from three electrodes parallel to the wave propagation direction is displayed in FIGS. 8A-8D. A phase delay between the electrodes that is characteristic of wave propagation is indicated by a black dotted line. The output of the wave estimation algorithm is also displayed with a shared time axis. The instantaneous wave direction and speed estimates for sustained waves are displayed in blue, while time points not meeting the sustained wave criteria are red. Sustained waves are defined as having a PGD greater than 0.5 for at least 2 consecutive seconds. The waves in this two-minute window have a bearing of 180 degrees relative to the positive x-axis and a speed of about 4 mm/s. Timepoints between subsequent slow-waves typically had lower PGD values and did not meet the sustained wave criteria, indicated by the red dots approximately every 20 seconds in the plots of FIGS. 8B-8D. Notably, for example, the data used to visualize the wave propagation in FIG. 7 corresponds to the data from the 30-50 second interval data shown in FIG. 8. For example, the start and end of a representative slow-wave is observed at about 30 and 50 seconds, respectively.

Figures 8A, 8B, 8C, 8D:
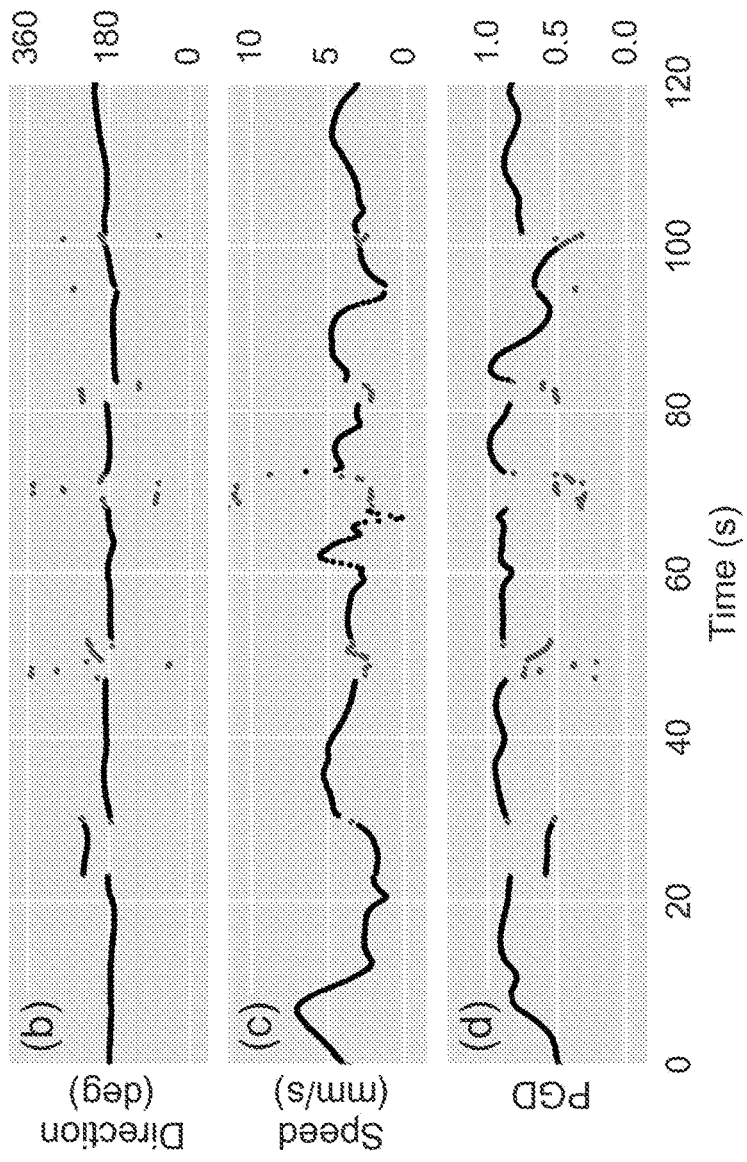
FIGS. 8A-8D show data plots of example two-minute segments of the surface Laplacian time series from example three electrodes parallel to the wave propagation direction.

FIGS. 8A-8D show data plots of example two-minute segments of the surface Laplacian time series from example three electrodes parallel to the wave propagation direction. FIG. 8A shows a plot of example voltage results of three channels from a 120 second segment of data from an example subject (subject 1). Wave propagation observed by the phase delay between the channels is depicted by the black diagonal dotted line. FIG. 8B shows a plot depicting the direction as computed by the wave estimation algorithm at every time point. FIG. 8C shows a plot depicting the speed as computed by the wave estimation algorithm at every time point. FIG. 8D shows a plot depicting the PGD as computed by the wave estimation algorithm at every time point. A PGD threshold is used to detect sustained waves (e.g., above 0.5 for at least 2 seconds). In the plots of FIGS. 8B-8D, the solid black line features of the plot indicate a sustained wave, while the grey dot features of the plot are used for points that do not meet the criteria. For example, the time scale along the horizontal axis applies to the data plots of FIGS. 8A-8D.

Figure 9:
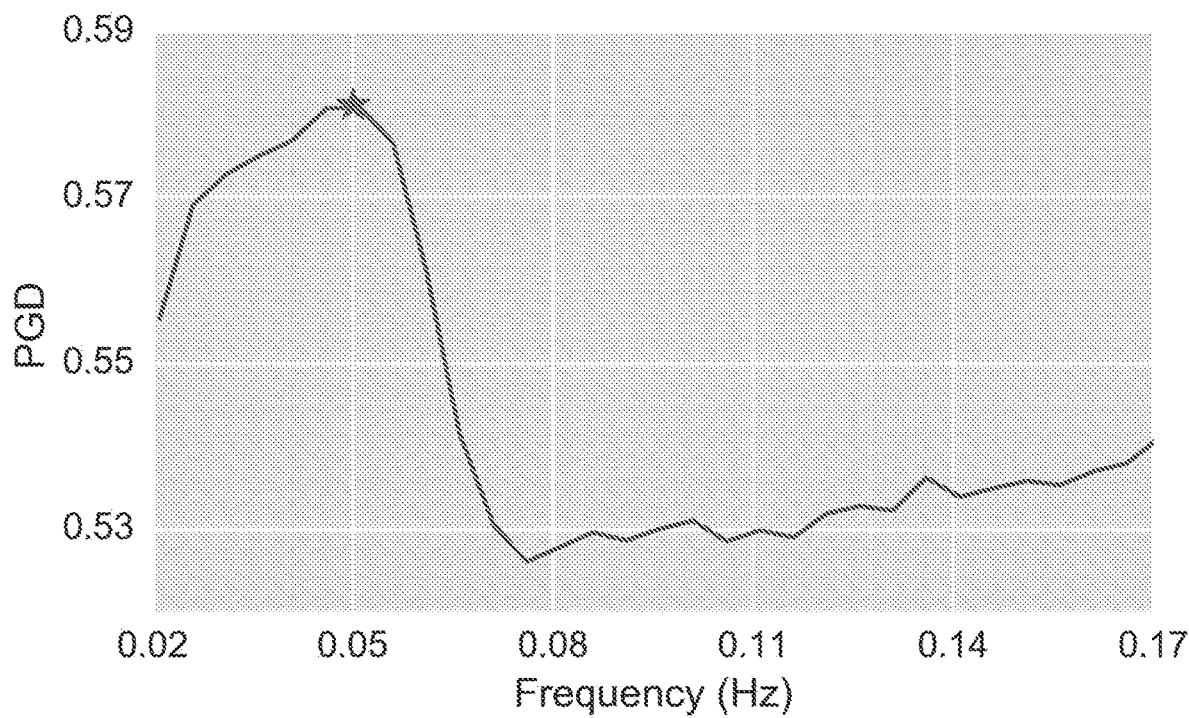
FIG. 9 shows plot depicting the PGD as a function of frequency for the band-pass filtered data from a subject.

To quantitatively confirm that the gastric electrophysiology was the source for the coordinated spatial activity, the mean PGD was computed as a function of frequency, as shown in FIG. 9.

FIG. 9 shows plot depicting the PGD as a function of frequency for the band-pass filtered data from an example subject (e.g., subject 1). The star indicates the maximum PGD, which is at 0.05 Hz. The plot was constructed by calculating the average PGD for the dataset after applying various band-pass filters (e.g., bandwidth=0.04 Hz) that sweep through a frequency range from 0.02 to 0.17 Hz. The peak PGD value occurred at 0.05 Hz, which corresponds to the normal stomach slow-wave frequency. The average PGD was used as an example metric to identify when waves were present, since a higher PGD indicates more spatial alignment. The peak of the PGD spectrum was present near 0.05 Hz for all subjects, confirming that the stomach was the source of the detected wave propagation.

Figure 10A:
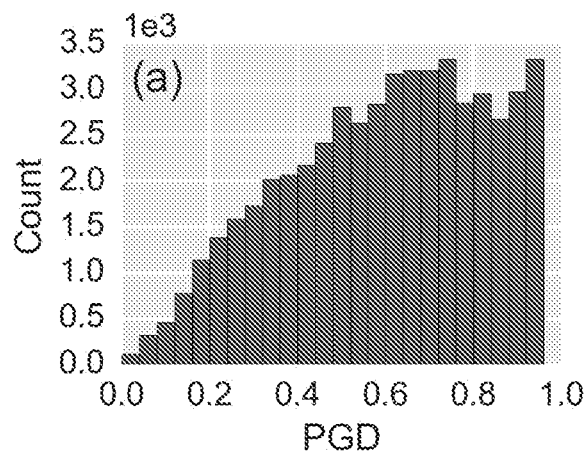
FIGS. 10A-10D show histograms depicting example results of wave direction, speed, and PGD revealing overall distributions of the wave propagation parameters for the entire recording.
Figure 10B:
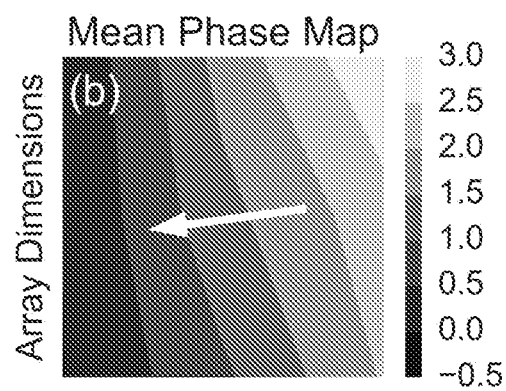
Figure 10C:
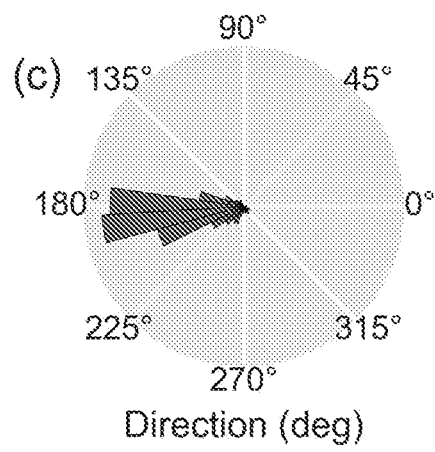
Figure 10D:
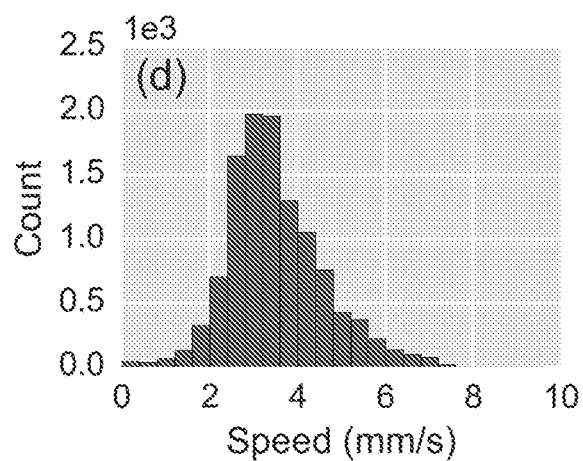

FIGS. 10A-10D show histograms depicting example results of wave direction, speed, and PGD. FIG. 10A shows a histogram of example PGD values from every time point throughout the recording for an example subject (e.g., subject 1). FIG. 10B shows the mean phase map, for example, computed using the instantaneous phase for time points meeting the sustained wave criteria. The white arrow indicates the propagation direction of the waves based on the direction of the negative phase gradient. FIG. 10C shows a polar histogram showing the estimated direction of propagation for sustained waves. FIG. 10D shows a histogram of the estimated speed for sustained waves.

As shown by FIGS. 10A-10D, the histograms of wave direction, speed, and PGD reveal overall distributions of the wave propagation parameters for the entire recording. For example, only time points of direction and speed during sustained waves were used to generate the histograms. For this particular subject, the waves propagated at 186±27 degrees at a speed of 3.2±0.9 mm/s throughout the recording. An average phase map was also computed for sustained waves by spatially unwrapping the phase at each time point and then subtracting the phase value of a reference electrode at that time prior to averaging (FIG. 10B). The white arrow shows the direction of propagation, which is along the negative phase gradient. FIGS. 10C and 10D capture the variability in the wave parameters throughout the recording.

The wave phenomena were observed in all eight of the subjects. Summary statistics for the various wave parameters are shown in Table 1.

TABLE 1

Wave propagation and EGG parameters across subjects

| SUBJECT | GENDER | WAVE DIRECTION (DEG) | WAVE SPEED (MM/S) | SUSTAINED WAVE (%) | % 2-4 CPM |
|---|---|---|---|---|---|
| 1 | M | 186 ± 27 | 3.2 ± 0.9 | 53* | 99.4 |
| 2 | F | 156 ± 29 | 4.8 ± 1.6 | 57* | 100 |
| 3 | F | 185 ± 40 | 3.4 ± 1.3 | 43* | 98.9 |
| 4 | M | 173 ± 35 | 3.6 ± 1.4 | 32* | 98.9 |
| 5 | M | 182 ± 48 | 3.8 ± 1.6 | 34* | 96.6 |
| 6 | F | 131 ± 48 | 3.2 ± 1.3 | 33* | 96.6 |
| 7 | M | 224 ± 44 | 4.0 ± 1.3 | 36* | 98.9 |
| 8 | M | 211 ± 35 | 3.9 ± 1.4 | 36* | 100 |
| MEAN | | 181 ± 29 | 3.7 ± 0.5 | 41 ± 10 | 98.7 ± 1.4 |

*p-value < $10^{-4}$

In the example study, the mean wave direction and speed for all subjects were 181±29 degrees and 3.7±0.5 mm/s, respectively. On average, 41% of the time points met the sustained wave criteria. There were no statistically significant differences in slow-wave propagation between male and female subjects. To quantify that the observed wave estimation could not be generated from noise, the test statistic was designed as the fraction of time that the PGD is greater than 0.5 for 2 seconds or longer. With generation of i.i.d. white Gaussian noise, a non-parametric bootstrapping method was used to develop the distribution of the test statistic under the null hypothesis. Examples of the false positive rate of i.i.d. white Gaussian noise are shown in FIG. 4. With this, a p-value was calculated using the histogram from the bootstrap, and found that it was less than $10^{-4}$ for all subjects, for example. Gastric contractions are initiated and coordinated by slow-wave activity, and the example results from this example study generally agree with existing descriptions of human gastric motility. MRI studies of contraction wave propagation in healthy stomachs have demonstrated a contractile displacement rate between 1.8-2.7 mm/s. For example, it has been shown, using invasive serosal electrical measurements: a mean slow-wave propagation speed of 8.0 mm/s in the pacemaker region, a drop to 3.0 mm/s in the corpus, followed by an increase to 5.7 mm/s in the antrum for normal subjects. The average speed recorded in this example study was 3.7±0.5 mm/s. The variability for each subject can be seen Table 1, with a distribution for a representative recording shown in FIG. 10D. These example results suggest that the HR-EGG reflects slow-wave activity in both the corpus and antrum, which is where most spatial abnormalities have been detected during invasive recordings.

The slow-wave direction estimates in this example study were consistent with the expected stomach orientation. Specifically, for example, the stomach typically lies in the left superior quadrant, terminates across the median line and can descend below the plane of the umbilicus. The average gastric slow-wave direction for the subjects was 181±29 degrees, consistent with the afore-mentioned anatomical description.

The slow-wave propagation was detected in both the fasting and post-prandial states for all the subjects in this example study. There were no significant differences in the speed and direction of the waves in the two states. A 250 kcal nutrient bar was chosen along with eight ounces of water since this is similar to the standardized meal given with tests of gastric motor function.

A commonly reported EGG metric, the percent of 2-4 cpm activity, is also shown in Table 1. This value was calculated by generating a spectrogram (e.g., 4 minute windows, 75% overlap) using the short-time Fourier transform of a single bipolar channel with the strongest gastric signal for each subject, and evaluating the percentage of time the dominant frequency was within the 2-4 cpm range. A value over 70% is indicative of a normal EGG, and all the subjects were above 95%.

Traditional EGG spectral analysis relies on using large windows of the recording (e.g., typically 4 minutes), due to the slow nature of the signal. This can be limiting, since gastric electrophysiological abnormalities may occur at a shorter time scale. Estimating the wave properties at every time sample, as shown in FIGS. 8A-8D, allows for the detection of instantaneous episodes of abnormalities. Moreover, the methodology in accordance with the present technology described herein is fully automated and not susceptible to human bias. The summary statistics for wave direction, wave speed and PGD in Table 1 demonstrate that the HR-EGG, produced by systems, devices and methods in accordance with the disclosed technology, can be used to estimate the gastric slow-waves properties for subjects.

In another example implementation, an example system in accordance with the present technology was used in a study to evaluate simultaneous EGG measurements using the system and wireless motility capsule recordings for gastroparesis, e.g., abnormal slow-wave direction associated with increased gastric pressure.

Abnormalities in EGG frequency and power have been observed in patients with gastroparesis. High-resolution electrical mapping can be used to provide details of stomach slow-wave activity. It is understood that abnormal slow-wave patterns can occur at the normal 3 cpm frequency in gastroparesis patients. Since a single-channel EGG measurement lacks spatial resolution, and it fundamentally cannot detect these types of abnormalities.

High-resolution EGG was carried out using an example system in accordance with the present technology on five normal subjects as well as a subject with idiopathic gastroparesis using an example data processing method for detecting slow-wave propagation with an array of cutaneous electrodes. The recording was time-synchronized to a wireless motility capsule, which measured internal pressure and pH. Although the gastroparetic subject exhibited normal 3 cpm EGG activity throughout the 5 hour recording, the example system was able to detect episodes of abnormal slow wave propagation. Interestingly, these episodes of abnormal propagation coincided with periods of higher pressure (e.g., >10 mmHg) as measured by the motility capsule, shown in FIGS. 11B and 11C. EGG slow-wave frequency was 3 cpm and spatial direction was quite uniform among the normal subjects, as shown in FIG. 11A.

Figure 11A:
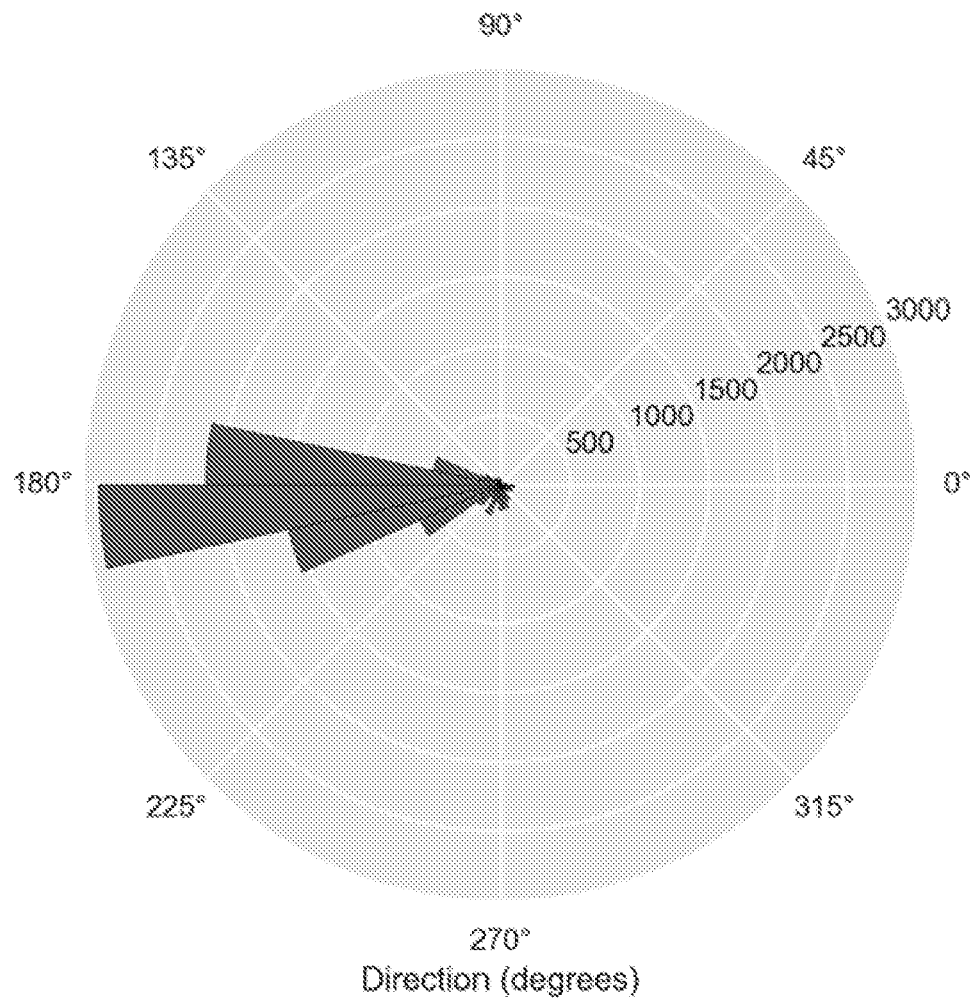
FIG. 11A shows a polar histogram of the slow-wave direction throughout recording for a normal subject.
Figures 11B, 11C:
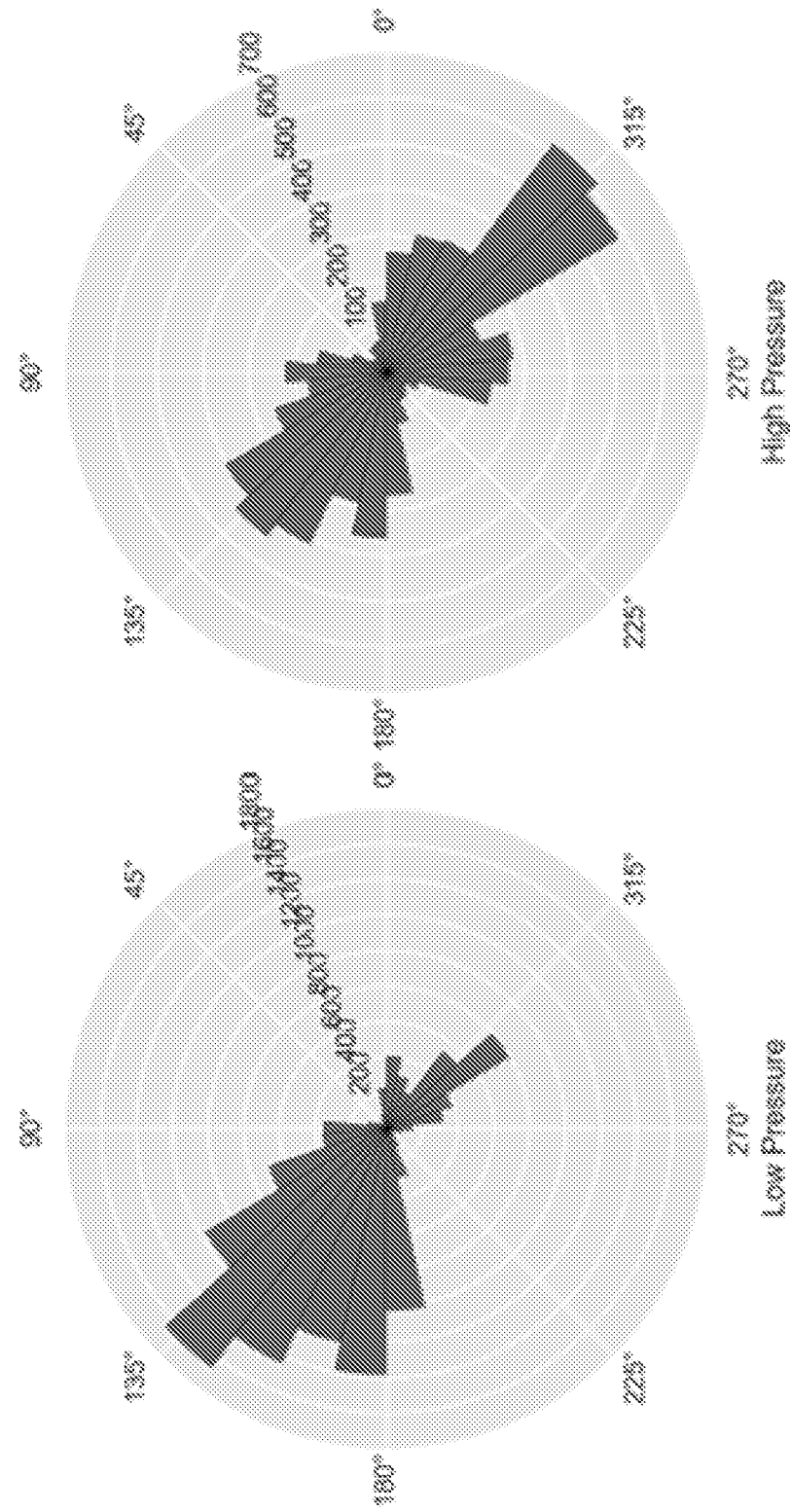
FIGS. 11B and 11C show polar histogram of the slow-wave direction throughout example recordings for a subject with idiopathic gastroparesis.

FIG. 11A shows example results depicting a polar histogram of the slow-wave direction throughout recording for a normal subject. FIGS. 11B and 11C show example results depicting polar histograms of the slow-wave direction throughout example recordings for a subject with idiopathic gastroparesis. Abnormal wave direction associated with pressure greater than 3 mmHg. The example results demonstrate that slow-wave spatial abnormalities can be detected non-invasively using an electrode array in accordance with the present technology.

Example implementations of example embodiments of the surface electrophysiological sensor device 100 was used to evaluate subjects with abnormal GI conditions or pathologies. Gastroparesis is an upper GI disorder characterized by delayed stomach emptying in addition to the symptoms presented in functional dyspepsia, and is estimated to effect 4% of the United States population. Approximately 30% of its etiology is related to diabetes, which is a costly and under-treated health epidemic with a doubling of its prevalence between 1990 and 2008 in the United States. Also, the overall prevalence of gastroparesis in Parkinson's disease is estimated to exceed 70% and is not routinely diagnosed. In the past decade, hospital admissions for gastroparesis have increased by 150%, posing a substantial healthcare cost.

The interstitial cells of Cajal (ICCs) generate the gastric myoelectric slow wave which provides the signal for antral peristalsis. Invasive electrical mapping has revealed that spatial abnormalities of the slow wave are present in subjects with gastroparesis. Moreover, depletion of the ICC has been identified as the key cellular defect in gastroparesis. A cutaneous high-resolution electrogastrogram could be used to estimate the direction and speed of the gastric slow wave in healthy subjects. In an example study, an example embodiment of the electrophysiological sensor device was used to assess whether the cutaneous HR-EGG can detect spatial gastric dysrhythmias in subjects with well-phenotyped gastroparesis versus controls.

An example HR-EGG method in accordance with the present technology was performed on seven subjects with gastroparesis, who had 30±10% gastric retention at 4-hours on scintigraphy (e.g., range 18-49%). Two of the gastroparesis subjects had diabetes, three were idiopathic, one had connective tissue disease, and one was post-viral (age: 59±14 years; BMI: 27±4; 5M/2F). HR-EGG was also performed on ten asymptomatic controls (age: 43±24 years; BMI: 24±6; 7M/3F). All subjects completed the PAGI-SYM questionnaire to evaluate fore-gut symptoms. The HR-EGG was recorded with an array of 25 skin mounted electrodes arranged in a 5 by 5 array with 2 cm spacing. Each subject was asked to fast prior to the start of the recording, and the duration of the recording was 30 minutes preprandial and 60 minutes postprandial. A volume reconstruction of the torso and stomach from CT images was performed in the gastroparesis subjects to ensure accurate placement of the electrode array.

Figure 12A:
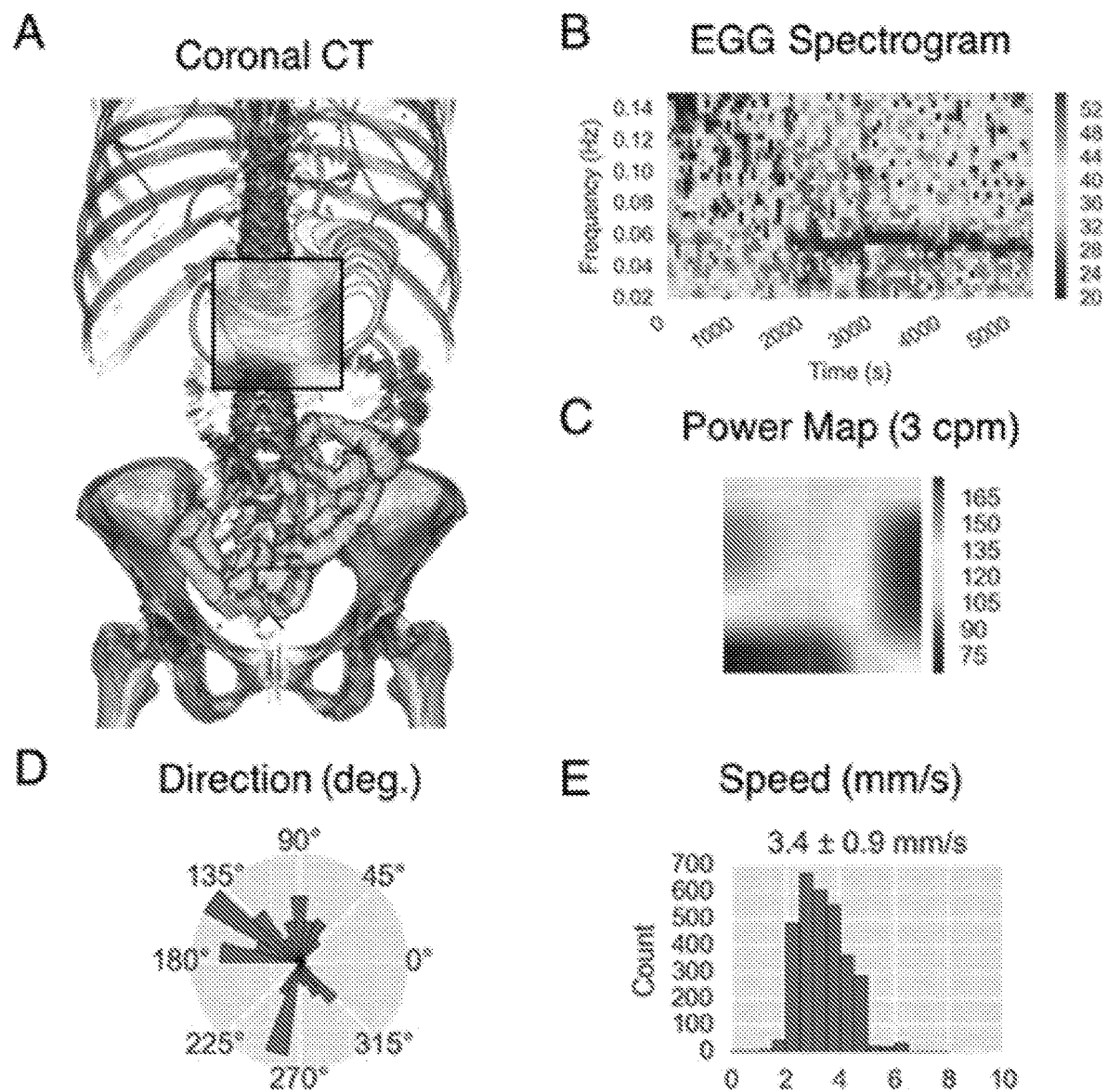
FIGS. 12A and 12B show images and data plots depicting example results from an example HR-EGG assessment of a patient subject with gastroparesis and a healthy subject, respectively.

FIG. 12A shows images and data plots depicting example results from an example HR-EGG assessment of a patient subject with gastroparesis. Panel A of FIG. 12A shows an example CT image of a subject with gastroparesis. Panel B of FIG. 12A shows an example spectrogram of the processed EGG data obtained from the subject with gastroparesis using the example multi-electrode array electrophysiological sensor. Panel C of FIG. 12A shows an example heat map of the processed EGG data obtained from the subject with gastroparesis using the example multi-electrode array electrophysiological sensor. Panel D of FIG. 12A shows a polar histogram showing the estimated direction of propagation for sustained waves for the subject with gastroparesis. Panel E of FIG. 12A shows a histogram of the estimated speed for sustained waves.

Figure 12B:
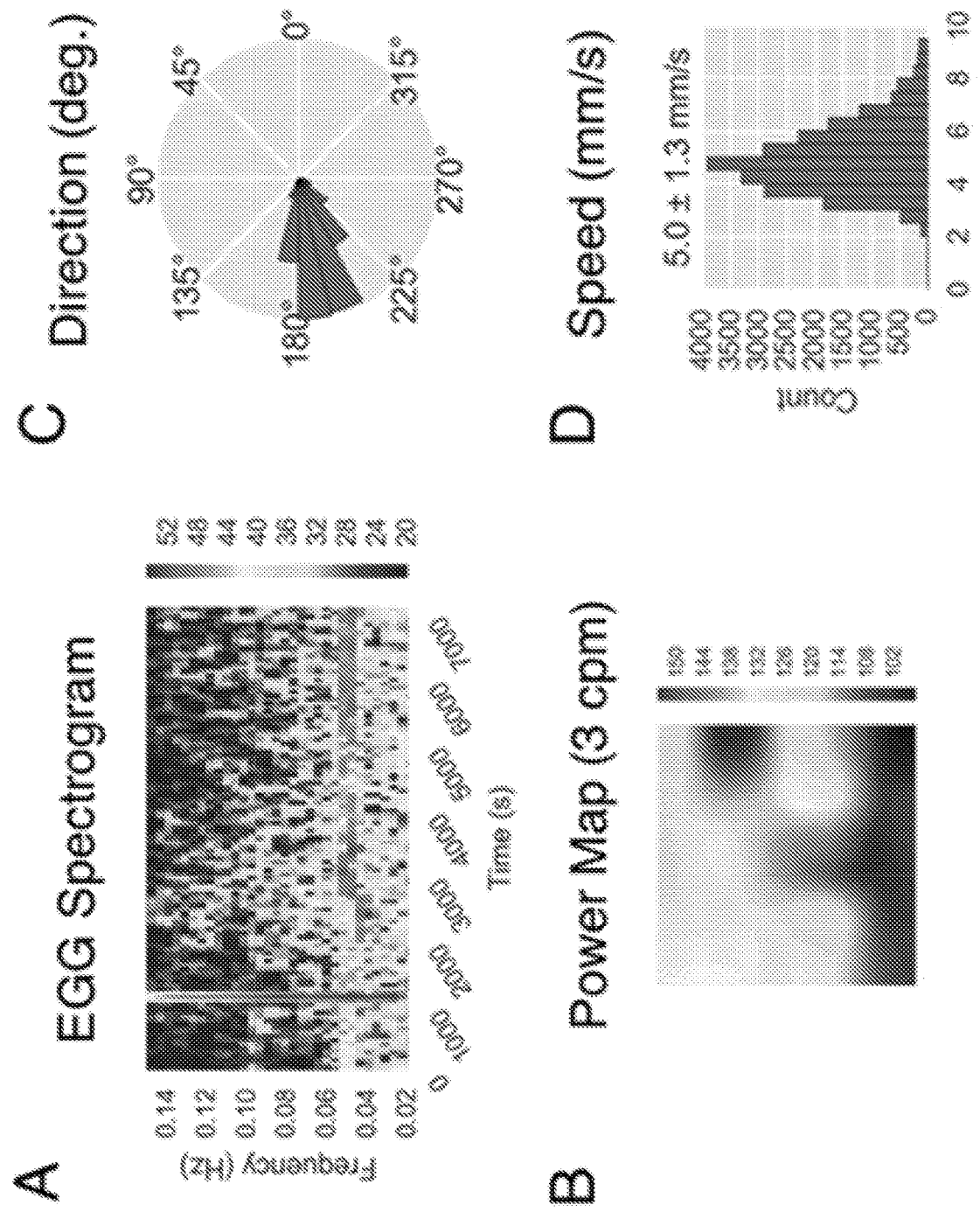

The subjects with gastroparesis had a mean Gastroparesis Cardinal Symptom Index (GCSI) score of 1.9±0.8, while the controls had a mean score of 0.1±0.2. The GCSI score is calculated from the PAGI-SYM questionnaire. All gastroparesis and control subjects had a normal single-channel EGG pattern, with 97±5% 2-4 cpm activity and a postprandial increase in amplitude. On the other hand, the HR-EGG analysis revealed spatial abnormalities in terms of direction and speed that discriminated gastroparesis from the controls. The controls had an average speed of 4.4±1.0 mm/s versus 3.3±0.5 mm/s in gastroparesis (p=0.009). Also, three out of the seven gastroparesis subjects had slow-waves with irregular direction (e.g., not traveling in a consistent direction along the stomach axis) for greater than or equal to 20% of the recording, unlike the controls which were all less than or equal to 15% (5±5%). An example of a subject with abnormal wave propagation is shown in FIG. 12A, while a representative healthy control is shown in FIG. 12B. The example results for the gastroparesis and healthy subjects are presented in Table 2 and Table 3, respectively.

FIG. 12B shows images and data plots depicting example results from an example HR-EGG assessment of a healthy patient subject. Panel A of FIG. 12B shows an example spectrogram of the processed EGG data obtained from the healthy patient subject using the example multi-electrode array electrophysiological sensor. Panel B of FIG. 12B shows an example heat map of the processed EGG data obtained from the healthy patient subject using the example multi-electrode array electrophysiological sensor. Panel C of FIG. 12B shows a polar histogram showing the estimated direction of propagation for sustained waves for the healthy patient subject. Panel D of FIG. 12B shows a histogram of the estimated speed for sustained waves.

TABLE 2

HR-EGG results in subjects with gastroparesis

| SUBJECT | GENDER | BMI | AGE | % 2-4 CPM | % ABNORMAL WAVE DIR | SPEED (MM/S) | GCSI SCORE | GES % 4 HR |
|---|---|---|---|---|---|---|---|---|
| 1 | M | 22.9 | 36 | 100 | 9 | 3.5 | 0.8 | 25.0 |
| 2 | F | 23.5 | 62 | 97.7 | 11 | 3.8 | 2.2 | 23.5 |
| 3 | M | 25.4 | 79 | 85.3 | 51 | 3.2 | 1.2 | 30.7 |
| 4 | M | 25.7 | 61 | 97.7 | 20 | 2.3 | 1.8 | 48.7 |
| 5 | F | 30.7 | 56 | 100 | 48 | 3.4 | 2.0 | 26.0 |
| 6 | M | 33.4 | 71 | 100 | 10 | 3.4 | 2.3 | 30.0 |
| 7 | M | 24.1 | 50 | 100 | 12 | 3.8 | 3.2 | 18.0 |
| MEAN | | 27 ± 4 | 59 ± 14 | 97 ± 5 | 23 ± 18 | 3.3 ± 0.5 | 1.9 ± 0.8 | 29 ± 10 |

TABLE 3

HR-EGG results in healthy controls

| SUBJECT | GENDER | BMI | AGE | % 2-4 CPM | % ABNORMAL WAVE DIR | SPEED (MM/S) | GCSI SCORE | GES % 4 HR |
|---|---|---|---|---|---|---|---|---|
| 1 | M | 22.3 | 28 | 94.0 | 1 | 3.6 | 0 | n/a |
| 2 | F | 21.8 | 21 | 100 | 2 | 4.9 | 0 | n/a |
| 3 | M | 24.4 | 30 | 100 | 1 | 5.0 | 0.2 | n/a |
| 4 | F | 23.5 | 75 | 100 | 10 | 4.4 | 0 | n/a |
| 5 | M | 32.0 | 77 | 96.6 | 10 | 3.2 | 0.2 | n/a |
| 6 | F | 17.8 | 29 | 100 | 5 | 5.2 | 0.1 | n/a |
| 7 | M | 19.5 | 32 | 100 | 6 | 5.3 | 0.3 | n/a |
| 8 | M | 21.1 | 79 | 98.9 | 0 | 3.9 | 0.6 | n/a |
| 9 | M | 26.0 | 23 | 100 | 4 | 5.8 | 0 | n/a |
| 10 | M | 36.3 | 36 | 85.1 | 15 | 3.0 | 0 | n/a |
| MEAN | | 24 ± 6 | 43 ± 24 | 97 ± 5 | 5 ± 5 | 4.4 ± 1.0 | 0.1 ± 0.2 | n/a |

The example results demonstrate that the cutaneous HR-EGG technique can identify slow-wave spatial abnormalities in gastroparesis.

Example EGG Surface Potential Mapping Techniques

Example embodiments of systems, devices and methods to provide electrophysiological surface potential mapping data in accordance with the present technology are described. Example comparisons of the disclosed surface electrophysiological monitoring technology with conventional systems are also described for EGG applications.

GI activity is not simply a pump. It is a complex, dynamic system that is controlled by several mechanisms. For example, if you eat a meal in a relaxed state, the stretching of the stomach wall can stimulate GI activity. In another instance, if you eat a meal and find yourself in a "fight or flight" situation, the GI activity will be immediately stopped by the sympathetic nervous system. Since the GI activity is slow and constantly changing, it is difficult to build an accurate heat map serially, i.e., without recording all electrodes simultaneously or in some interleaved/multiplexed fashion.

Factors that increase activity include stretching of the smooth muscle, stimulation by acetylocholine, stimulation by parasympathetic nerves that secrete acetylacholine at their endings, and stimulation by several gastrointestinal hormones. Factors that decreases activity include the effect of norepinephrine or epinephrine on the fiber membrane, and stimulation of the sympathetic nerves that secrete mainly norepinephrine at their endings.

Figure 13A:
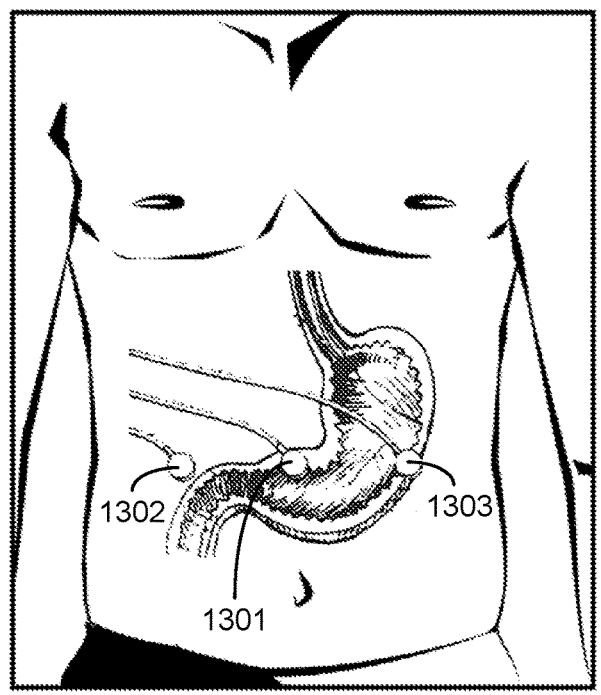
FIGS. 13A-13C show a diagram of and example data obtained from a conventional single channel EGG electrode device in a traditional electrode placement.
Figure 13B:
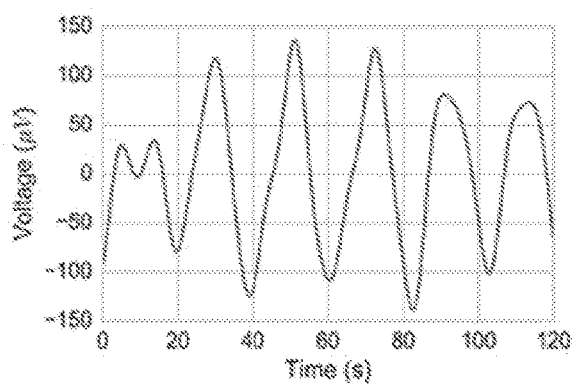
Figure 13C:
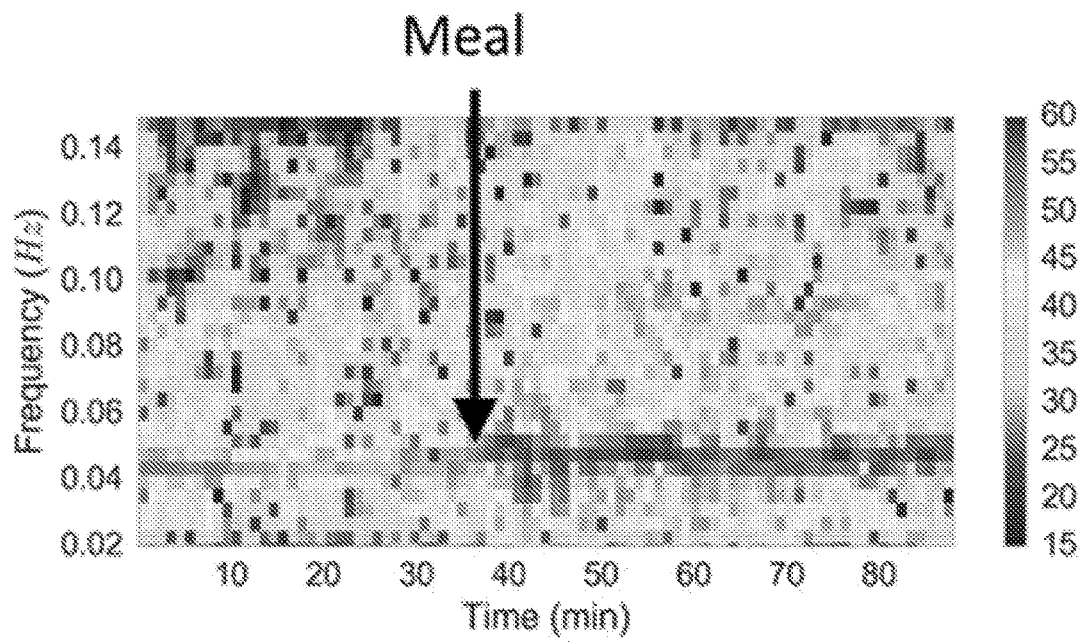

Traditional EGG measurements are recorded with three electrodes that include a measurement electrode, a reference electrode, and a ground electrode placed positioned halfway between the xiphoid and umbilicus. FIG. 13A shows a diagram of a conventional single channel EGG electrode device in a traditional electrode placement. As shown in the diagram, the conventional EGG electrode device consists of a reference electrode 1301, a ground electrode 1302 and a measurement electrode 1303. These three electrodes produce a single time-series of voltage data, which is then interpreted using spectral analysis. FIG. 13B shows an example of a two minute time-series of voltage data obtained from a human subject using a conventional EGG electrode device, like that shown in FIG. 13A. FIG. 13C shows an example spectral analysis plot based on 90 minutes of the time-series of voltage data obtained from the subject using the conventional EGG electrode device, like that shown in FIG. 13A. For example, the spectral analysis is typically performed using the Fourier transform on a 4-minute window of data. The spectrogram in FIG. 13C is constructed by sliding 4-minute windows through the entire recording with 75% overlap of data each time, so you have a new estimate every minute. Each column of the spectrogram in FIG. 13C represents one of the windows of data. The red horizontal band at approximately 0.05 Hz is the EGG activity. The darker shade of red means higher activity, as indicated by the color bar.

In the example recordings from FIGS. 13B and 13C, the subject ate a meal at around 35 minutes. The conventional spectrogram in FIG. 13C shows that there is an increase in the power of the measured signal after that point, i.e., after the subject ate the meal. Notably, this is one of the criteria that has been used to assess if someone's EGG is 'normal'. Another feature typically extracted from a conventional spectrogram, like that in FIG. 13C, is the percentage of the recording that is in a dominant frequency range between 0.04 Hz and 0.06 Hz. If the dominant EGG frequency is between 0.04 Hz and 0.06 Hz for greater than 70% of the recording, the subject is considered normal. Notably, this threshold value was chosen heuristically based on the results from previous studies that included EGG recordings of 189 asymptomatic subjects across multiple studies. While this finding suggests that normal subjects can have dysrhythmias up to 30% of the time, the 30% time percentage outside of the threshold range is more likely due to signal noise and low amplitude associated with the conventional EGG measurement and analysis techniques. For example, some evidence for this is based on recent findings where fewer frequency deviations were detected on serosal recordings (directly on the stomach) as compared to the EGG, implying that some of the EGG acquired dysrhythmias are artefactual.

As such, one issue to address is where should one place the electrodes to record the highest signal-to-noise ratio signal. In the case of the EGG, the wall of the stomach is the source of the signal that is being recording. The amplitude of the signal is attenuated as it conducts through the tissue (e.g., skin, fat, muscle, etc.), and the attenuation is a function of distance. In other words, the further from the source, the weaker the signal is. Therefore, it is optimal for the electrodes to be as close to the stomach as possible. This issue is problematic with conventional EGG electrode systems because it requires expertise by an operating to properly place the single-channel electrode device in the correct location for the patient. For example, even slight misplacements can result in lost information that may be important in evaluating the physiological function of interest.

Figure 14:
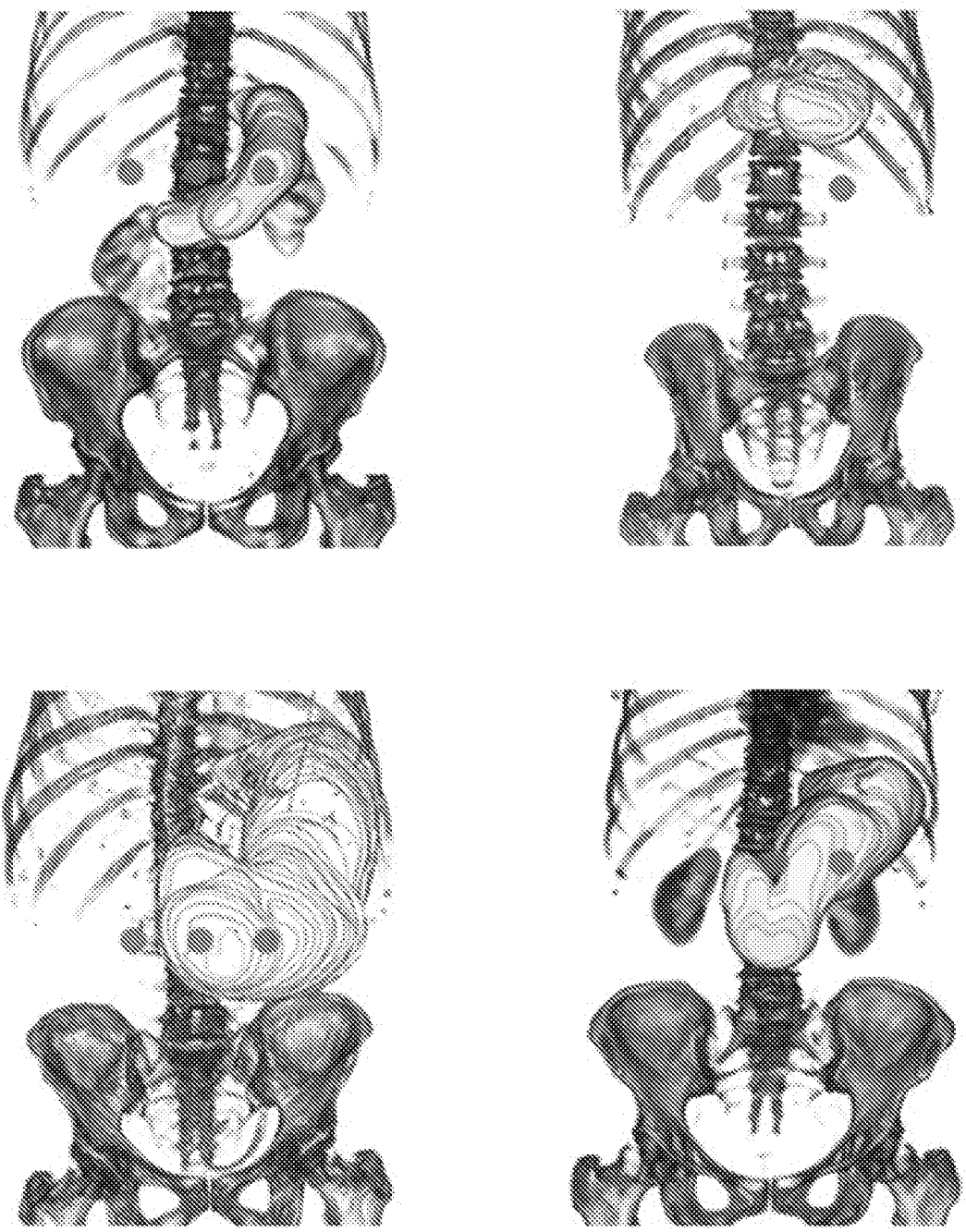
FIG. 14 shows a diagram of CT reconstruction images depicting the torso and stomach for four subjects that demonstrate a large amount of variability in shape, size, and location of gastrointestinal anatomy across subjects.

Another issue pertains to how much variability there is in stomach anatomy between subjects. Volumetric CT scans from subjects (e.g., 29 subjects), reconstructed to show the skeleton and stomach, show that there is a large amount of variability in shape, size, and location. FIG. 14 shows a diagram of CT reconstruction images depicting the torso and stomach for four subjects to demonstrate this large variability. As shown in the diagram, the circular dots indicate traditional EGG electrode placement. For example, for the position of the stomach relative to the xiphoid, the y-dimension had the most variability between subjects with a range of 17.4 cm. Also, for example, the volume of the stomach was highly variable between subjects, with an average of 510±522 mm$^3$ and a range of 136 to 2694 mm$^3$. This issue further compounds the problems with conventional EGG electrode systems. For example, as depicted in the examples of FIG. 14, subjects' stomach locations and physiologically active regions of interest significantly vary between the subjects. Conventional EGG systems are not equipped to mitigate this variability.

Moreover, another issue is how much does the signal attenuate though the tissue, and how close to the stomach do the electrodes need to be to acquire a good signal. Embodiments of the multi-channel electrode array in accordance with the present technology are capable of addressing this issue. In an example implementation, a 100-channel electrode array (e.g., 10×10 array with 2 cm spacing) was used to simultaneously record from 100 channels, in which the difference between any two electrodes is used to generate a voltage time-series. Similarly, as a comparative example, the 100-channel electrode array was used to record from the locations that would be interrogated by a conventional EGG system. FIGS. 15A-15B and FIGS. 16A-16B illustrate the comparisons.

Figure 15A:
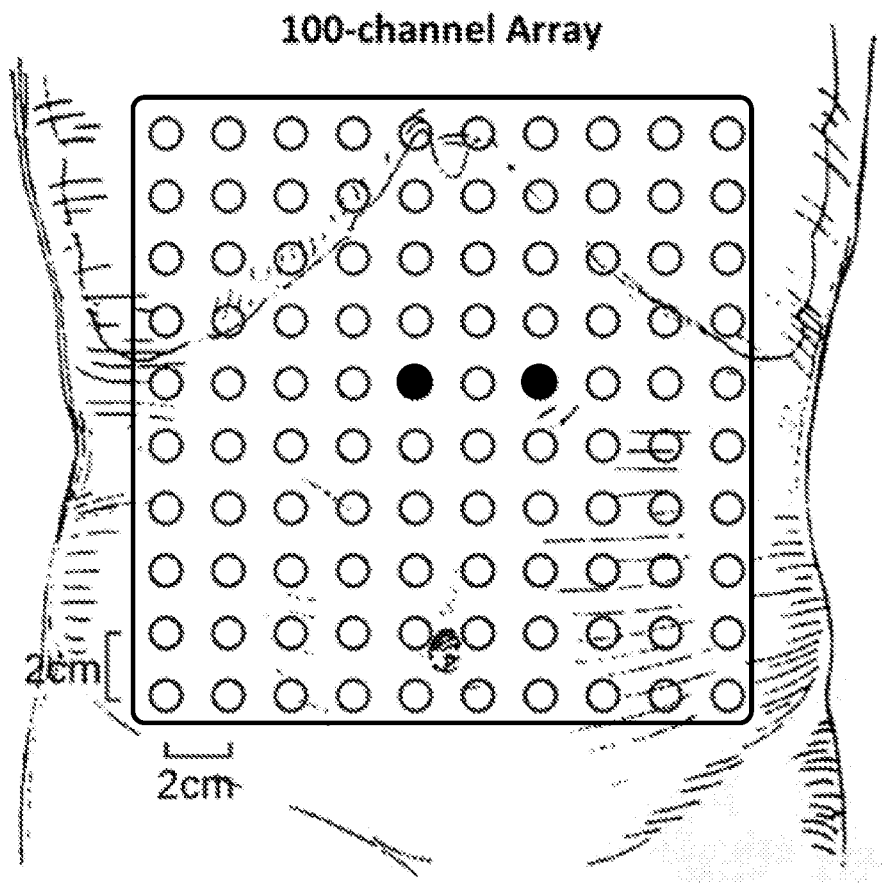
FIGS. 15A and 15B show a diagram and spectrogram corresponding to an example 100 electrode array attached to a subject's torso from which a conventional single-channel electrode pair obtains an EGG recording.
Figure 15B:
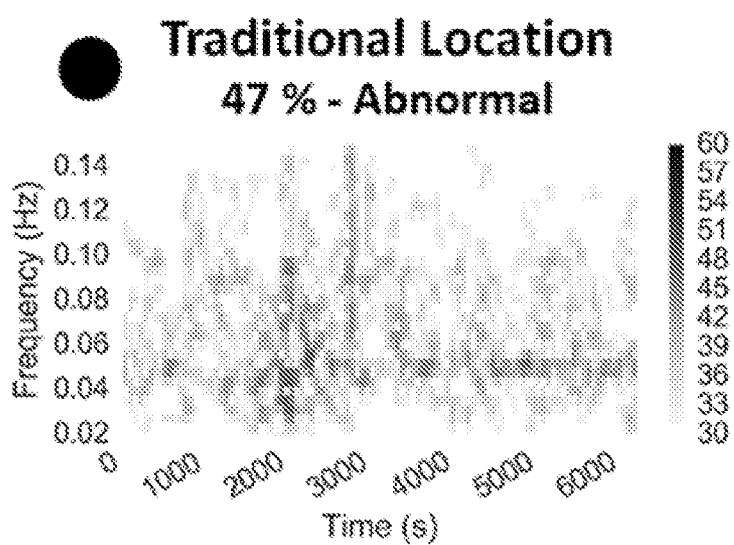

FIG. 15A shows a diagram of an example 100-channel electrode array attached to a subject's torso. FIG. 15B shows an example spectrogram generated from the electrode pair associated with a conventional single-channel EGG location, identified by the two solid-filled (black) electrodes corresponding to the reference and measurement electrodes. What is shown in FIGS. 15A and 15B, in this example implementation, include the results from the 100-channel electrode array when merely two electrodes that correspond to a conventional single-channel EGG device were used to record a voltage time-series of the subject's stomach. As shown from the example data in FIG. 15B, the single-channel electrode pair used to take the example EGG recordings provides a very weak signal, as demonstrated in the spectrogram.

Figure 16A:
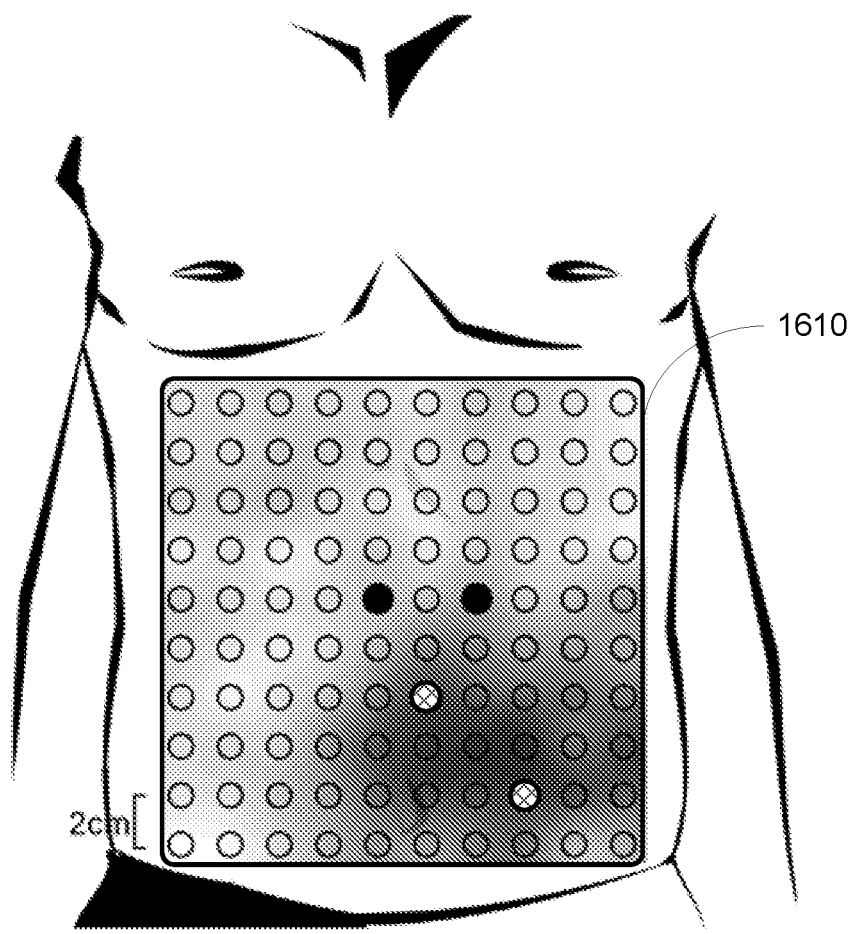
FIGS. 16A and 16B show a diagram and spectrogram corresponding to an example 100 electrode array attached to a subject's torso from which a multi-channel electrode EGG mapping technique obtains an EGG recording.
Figure 16B:
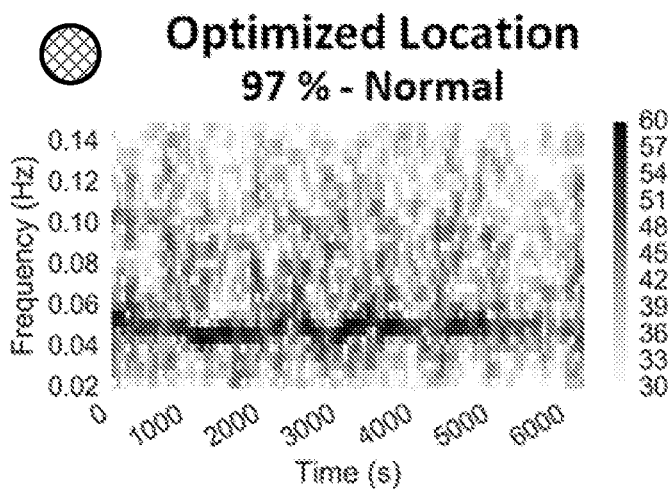

FIG. 16A shows a diagram of an example 100-channel electrode array attached to a subject's torso. FIG. 16B shows an example spectrogram generated from an adaptive electrode pair determined to have the highest signal-to-noise ratio, identified by the two patterned-filled electrodes. What is shown in FIGS. 16A and 16B, in this example implementation, include the results from the 100-channel electrode array when the 100-channel electrode array is operated in accordance with the disclosed technology to obtain and process multi-channel data (e.g., record voltage time-series of the subject's stomach across at least some or all of the electrodes and process the data using the method 180). As shown in FIG. 16A, an average EGG potential map 1610, or "heat map", can be computed using the data from all the electrodes throughout the entire recording. The EGG potential map represents the area of the array that has the highest EGG power in the 0.04-0.06 Hz frequency band. The example heat map 1610 was produced by re-referencing the data to each electrode in the array and calculating the mean EGG power relative to all other electrodes. The region of the potential map with the highest power corresponds to the region closest to the stomach for the particular subject. For example, the heat map 1610 can be used to select which electrode pair or pairs in the region of interest, e.g., the region with highest activity of EGG potential, to continue to monitor from.

The spectrogram of FIG. 16B demonstrates the strength of the EGG signal measured by each electrode pair in the 100-channel electrode array. There is a dramatic fall-off in the EGG signal as voltage-time series is recorded a distance further away from the stomach. In the example implementation, a shift of about 5 cm away from the stomach almost completely attenuates the EGG signal, which is illustrated by the example results in the heat map 1610. The example implementations included performing the same procedure on 17 normal subjects, in which 9 out of the 17 subjects drop below the 70% threshold and would have been considered abnormal when measured using the two electrodes that correspond to a conventional single-channel EGG device. Whereas, when using the 100-channel electrode array is operated in accordance with the disclosed technology, all 17 healthy subjects were found to be within the 70% threshold and therefore verified by the technique as normal. This example evidence shows that EGG signals are extremely sensitive to the placement of the electrodes. The electrophysiological sensor devices, systems, and methods in accordance with the present technology are capable of reliably recording EGG signals in a manner that accounts for electrode location variability and thereby is adaptable to all types of subjects.

Figure 17:
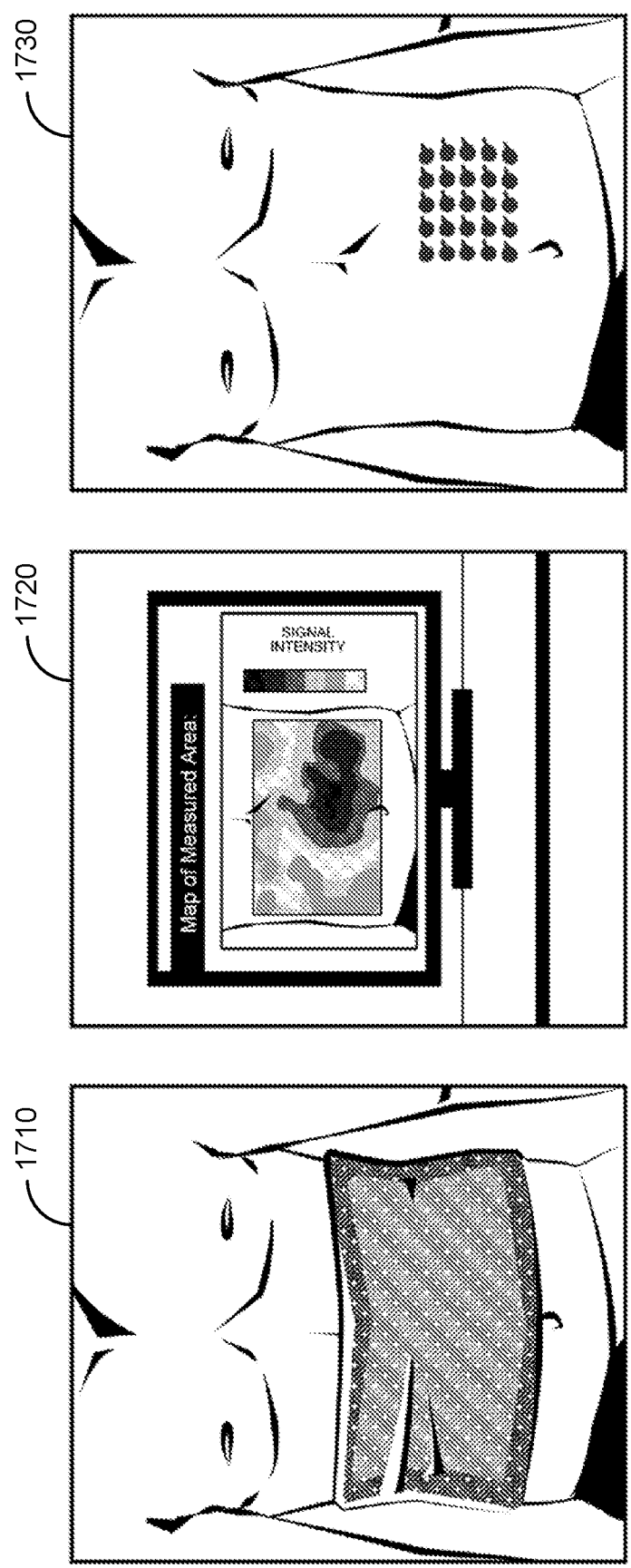
FIG. 17 shows an illustration depicting an example clinical-to-ambulatory workflow technique using example surface electrophysiological sensor devices in accordance with the present technology.

FIG. 17 shows an illustration depicting an example clinical-to-ambulatory workflow technique using example surface electrophysiological sensor devices in accordance with the present technology. As previously discussed, the placement of the array of electrodes is critical in acquiring an EGG signal with a high signal-to-noise ratio. One possible workflow using the disclosed surface electrophysiological sensor devices can include operating a large array of electrodes (e.g., 100-channel electrode array, such as the example in FIG. 1E) in a clinical setting, e.g., with a health care provider (HCP) during an outpatient appointment, to provide clinically-relevant information used to guide an ambulatory implementation of a smaller array of electrodes (e.g., 25-channel electrode array, such as the example in FIG. 1D) that is passively and autonomously operated while worn by the patient user.

As shown in an illustration 1710 in the diagram of FIG. 17, the example large, 100-channel electrode array is placed on the abdomen of the patient user, e.g., by the HCP during an appointment, covering a large area of the abdominal surface. The example large, 100-channel electrode array is in communication with the data processing unit 120, e.g., which can be embodied on a computer or mobile computing device used by the HCP. Data is recorded for a certain period of time, for example, 10 to 20 minutes. A meal, drug, and/or other stimulus may be administered prior to or during the recording to increase GI activity. Similarly, a drug or other substance may be administered prior to or during the recording to decrease GI activity. After the clinical recording, a surface potential map is computed by the data processing unit 120 and displayed, as depicted in an illustration 1720 in the diagram of FIG. 17. The HCP may review the results and determine an area for placement of the example smaller, 25-channel electrode array. The example smaller 25-channel electrode array is placed on the abdominal region with the highest activity, and the patient user proceeds to monitor GI function remote from the clinical setting, as depicted in an illustration 1730 in the diagram of FIG. 17. Future data collection is acquired using the smaller array, and processed using the data processing unit 120, e.g., which can be embodied on a computer or mobile computing device of patient user, in the cloud (e.g., data processing system 150), or on-board the wearable sensor unit having the smaller electrode array. For example, several advantages of this approach are provided, including lower bandwidth necessary for data storage/transmission and more comfort for the user, especially for prolonged ambulatory monitoring.

Figure 18:
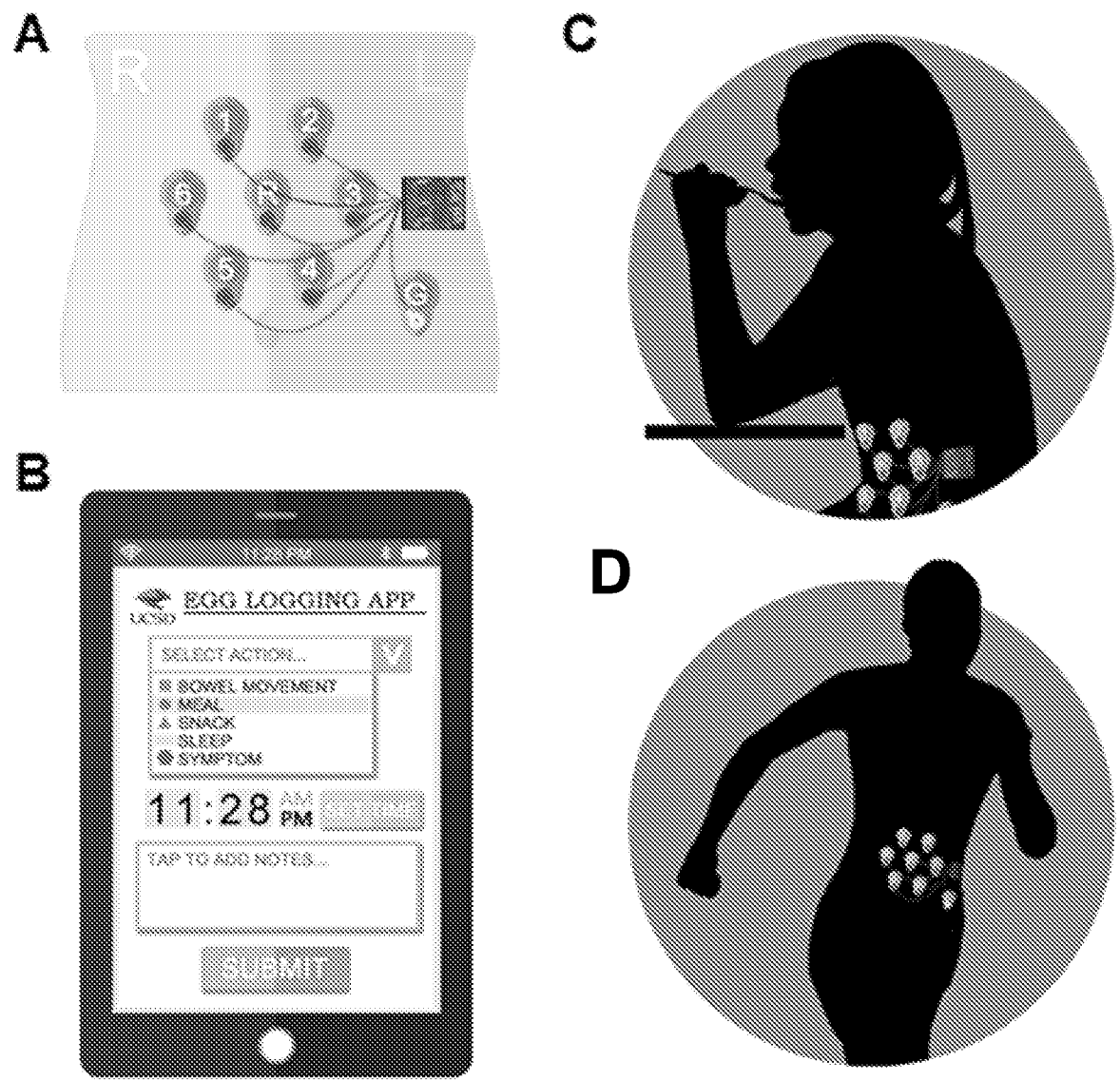
FIG. 18 shows an illustration of an example wearable, ambulatory surface electrophysiological sensor system.

FIG. 18 shows an illustration of an example wearable, ambulatory surface electrophysiological sensor system. Panel (A) of FIG. 18 shows an example of skin-mounted electrodes of an example embodiment of the electrode array 111 in communication with a hardware implementation of the signal conditioning unit 115 and/or data processing unit 120. Panel (B) of FIG. 18 shows an example of a smartphone application (app) for logging events (e.g., sleep, meal, snack, symptom, bowel movement) associated with ambulatory monitoring of EGG, which enables recording of the gastric electrical activity outside of the clinic. Panels (C) and (D) of FIG. 18 shows example illustrations of such activity including eating and exercising, respectively.

EXAMPLES

The following examples are illustrative of several embodiments in accordance with the present technology. Other exemplary embodiments of the present technology may be presented prior to the following listed examples, or after the following listed examples.

In some embodiments in accordance with the present technology (example 1), a device for electrophysiological monitoring includes an electrophysiological sensor structured to include an array of electrodes spatially arranged on a substrate and operable to acquire electrophysiological signals from the electrodes of the array when in contact with skin of a subject to obtain time-series data of the electrophysiological signals, in which the electrodes are spaced about an anatomical structure on the subject's body with at least one electrode placed with reference to an anatomical landmark and other electrodes of the electrode array each placed at a spatial distance from another of the surface electrodes, whereby all the surface electrodes have a determined location with respect to the anatomical landmark; an electronics unit including a signal conditioning circuit to amplify the acquired electrophysiological signals; and a data processing unit including a processor to process data based on the amplified acquired electrophysiological signals, the data processing unit configured to spatially filter the time-series data to generate a spatially resolved time-series data set that includes a reduced amount of data than the obtained time-series data of electrophysiological signals, and to process the spatially resolved time-series data set to determine wave propagation parameters including one or both of direction and speed for each time point of interest of the acquired electrophysiological signals, in which the wave propagation parameters are associated with a physiological function of the anatomical structure of the subject's body to which the electrophysiological sensor is in contact.

Example 2 includes the device of example 1, in which the array of the electrodes includes a reference electrode and two or more measurement electrodes, and the obtained time-series data includes a plurality of differential time-series data between recorded electrophysiological signals from the reference electrode and recorded electrophysiological signals from at least one of the two or more measurement electrodes.

Example 3 includes the device of example 1, in which the array includes at least a 5×5 grid of the electrodes.

Example 4 includes the device of example 1, in which the electrophysiological sensor is noninvasive to the subject's body and autonomously operable to passively acquire the electrophysiological signals.

Example 5 includes the device of example 1, in which the data processing unit is configured to determine the wave propagation parameters by analyzing phase information of the spatially resolved time-series data set.

Example 6 includes the device of example 1, in which the data processing unit is configured to produce an electrophysiological monitoring output that includes the determined wave propagation parameters to provide information on the physiological function of the anatomical structure of the subject's body.

Example 7 includes the device of example 6, in which the electrophysiological monitoring output includes a graph displaying at least one of the wave propagation parameters or summary statistics of the wave propagation parameters.

Example 8 includes the device of example 1, in which the data processing unit is configured to compare the wave propagation parameters to a standard set of wave propagation parameters to distinguish the physiological function as a healthy function or a dysfunction.

Example 9 includes the device of example 1, in which the data processing unit is configured to process the wave propagation parameters with an uncertainty value associated with each parameter to determine statistical information, in which the statistical information includes a probability of the physiological function of the anatomical structure associated with an abnormality or degree of severity.

Example 10 includes the device of example 1, in which the data processing unit is configured to determine average intensity values of the acquired electrophysiological signals over a course of the time-series data, and to map the average intensity values to locations where the of the surface electrodes are with respect to the subject's body to produce an electrophysiological signal heat map, the electrophysiological signal heat map including one or both of a graph and image having the average intensity values displayed with respect to an anatomical structure of the subject's body.

Example 11 includes the device of example 1, further including a wireless communications unit to wirelessly transmit the amplified signals to an external computing device in which the data processing unit resides.

Example 12 includes the device of example 1, in which the data processing unit is resident on an external computing device including a smartphone, a tablet, a laptop computer, a desktop computer, or a wearable computing device including a smartwatch or a smartglasses device.

Example 13 includes the device of example 12, in which the data processing unit includes one or more computers in communication with the external computing device over the Internet, the one or more computers configured to process or store one or more of the obtained time-series data or the wave propagation parameters.

Example 14 includes the device of example 1, in which one or both of the electronics unit and the data processing unit is configured to spectrally filter the time-series data, down-sample the time-series data, or remove signal artifacts from the time-series data.

Example 15 includes the device of example 1, in which the electrophysiological sensor includes one or more marks on substrate indicating a place to align the electrophysiological sensor with the anatomical landmark.

Example 16 includes the device of example 1, in which the electrophysiological sensor includes a securement component including an adhesive, a belt or a strap to attach to the subject's body.

Example 17 includes the device of example 1, in which the substrate includes a flexible substrate including an electrically insulative material and structured to adhere to the skin of the subject.

Example 18 includes the device of any of examples 1-17, in which the electrophysiological signals are electrogastrogram signals, and the anatomical structure includes a tissue or organ associated with the gastrointestinal system.

In some embodiments in accordance with the present technology (example 19), a device for electrophysiological monitoring includes an electrophysiological sensor structured to include an array of electrodes spatially arranged on a substrate and operable to acquire electrophysiological signals from the electrodes of the array when in contact with skin of a subject to obtain time-series data of the electrophysiological signals, in which the electrodes are spaced about an anatomical structure on the subject's body with at least one electrode placed with reference to an anatomical landmark and other electrodes of the electrode array each placed at a spatial distance from another of the surface electrodes, whereby all the surface electrodes have a determined location with respect to the anatomical landmark; and a data processing unit including a processor to process spatially resolved time-series data based on the acquired electrophysiological signals, the data processing unit configured to determine wave propagation parameters including one or both of direction and speed for each time point of interest of the acquired electrophysiological signals, in which the wave propagation parameters are associated with a physiological function of the anatomical structure of the subject's body to which the electrophysiological sensor is in contact.

Example 20 includes the device of example 19, in which the array of the electrodes includes a reference electrode and two or more measurement electrodes, and the obtained time-series data includes a plurality of differential time-series data between recorded electrophysiological signals from the reference electrode and recorded electrophysiological signals from at least one of the two or more measurement electrodes.

Example 21 includes the device of example 19, in which the array includes at least a 5×5 grid of the electrodes.

Example 22 includes the device of example 19, in which the array of electrodes includes surface Laplacian electrodes structured to include concentric rings operable to provide spatially resolved information in the obtained time-series data.

Example 23 includes the device of example 19, in which the data processing unit is configured to spatially filter the time-series data to generate the spatially resolved time-series data set that includes a reduced amount of data than the obtained time-series data of electrophysiological signals.

Example 24 includes the device of example 19, including an electronics unit including a signal conditioning circuit to amplify the acquired electrophysiological signals.

Example 25 includes the device of example 24, in which one or both of the electronics unit and the data processing unit is configured to spectrally filter the time-series data, down-sample the time-series data, or remove signal artifacts from the time-series data.

Example 26 includes the device of example 19, in which the electrophysiological sensor is noninvasive to the subject's body and autonomously operable to passively acquire the electrophysiological signals.

Example 27 includes the device of example 19, in which the data processing unit is configured to determine the wave propagation parameters by analyzing phase information of the spatially resolved time-series data.

Example 28 includes the device of example 19, in which the data processing unit is configured to produce an electrophysiological monitoring output that includes the determined wave propagation parameters to provide information on the physiological function of the anatomical structure of the subject's body.

Example 29 includes the device of example 28, in which the electrophysiological monitoring output includes a graph displaying at least one of the wave propagation parameters or summary statistics of the wave propagation parameters.

Example 30 includes the device of example 19, in which the data processing unit is configured to compare the wave propagation parameters to a standard set of wave propagation parameters to distinguish the physiological function as a healthy function or a dysfunction.

Example 31 includes the device of example 19, in which the data processing unit is configured to process the wave propagation parameters with an uncertainty value associated with each parameter to determine statistical information, in which the statistical information includes a probability of the physiological function of the anatomical structure associated with an abnormality or degree of severity.

Example 32 includes the device of example 19, in which the data processing unit is configured to determine average intensity values of the acquired electrophysiological signals over a course of the time-series data, and to map the average intensity values to locations where the of the surface electrodes are with respect to the subject's body to produce an electrophysiological signal heat map, the electrophysiological signal heat map including one or both of a graph and image having the average intensity values displayed with respect to an anatomical structure of the subject's body.

Example 33 includes the device of example 19, further including a wireless communications unit to wirelessly transmit the electrophysiological signals to an external computing device in which the data processing unit resides.

Example 34 includes the device of example 19, in which the data processing unit is resident on an external computing device including a smartphone, a tablet, a laptop computer, a desktop computer, or a wearable computing device including a smartwatch or a smartglasses device.

Example 35 includes the device of example 34, in which the data processing unit includes one or more computers in communication with the external computing device over the Internet, the one or more computers configured to process or store one or more of the obtained time-series data or the wave propagation parameters.

Example 36 includes the device of example 19, in which the electrophysiological sensor includes one or more marks on substrate indicating a place to align the electrophysiological sensor with the anatomical landmark.

Example 37 includes the device of example 19, in which the electrophysiological sensor includes a securement component including an adhesive, a belt or a strap to attach to the subject's body.

Example 38 includes the device of example 19, in which the substrate includes a flexible substrate including an electrically insulative material and structured to adhere to the skin of the subject.

Example 39 includes the device of any of examples 19-38, in which the electrophysiological signals are electrogastrogram signals, and the anatomical structure includes a tissue or organ associated with the gastrointestinal system.

In some embodiments in accordance with the present technology (example 40), a method for electrophysiological monitoring includes acquiring electrophysiological signals from surface electrodes of an electrode array coupled to skin of a subject to obtain time-series data of the electrophysiological signals; processing the time-series data to produce processed time-series data, in which the processing includes spectral filtering the time-series data, down-sampling the time-series data, or removing signal artifacts from the time-series data; spatially filtering the processed time-series data to generate a spatially resolved time-series data set, in which the spatially resolved time-series data set includes a reduced amount of data than the processed time-series data of electrophysiological signals; processing the spatially resolved time-series data set to extract wave propagation parameters including one or both of direction and speed for each time point of interest of the acquired electrophysiological signals, in which the wave propagation parameters are associated with a physiological function of an anatomical structure of the subject's body to which the electrode array is coupled, the producing the wave propagation parameters includes analyzing phase information of the spatially resolved time-series data set; and producing an electrophysiological monitoring output that includes the extracted wave propagation parameters to provide information on the physiological function of the anatomical structure of the subject's body.

Example 41 includes the method of example 40, in which the surface electrodes of the electrode array are spatially arranged about the anatomical structure on the subject's body with at least one electrode placed with reference to an anatomical landmark and other electrodes of the electrode array each placed at a spatial distance from another of the surface electrodes, whereby all the surface electrodes have a determined location with respect to the anatomical landmark.

Example 42 includes the method of example 40, in which the electrode array includes at least a 5×5 grid of the surface electrodes.

Example 43 includes the method of example 40, including selecting one surface electrode of the electrode array as a reference electrode; selecting two or more other surface electrodes of the electrode array as two or more measurement electrodes; and recording the electrophysiological signals from the selected surface electrodes.

Example 44 includes the method of example 43, in which the time-series data includes a plurality of differential time-series data between the recorded electrophysiological signals from the reference electrode and the recorded electrophysiological signals from at least one of the two or more measurement electrodes.

Example 45 includes the method of example 40, in which the electrophysiological signals acquired by the surface electrodes are simultaneously recorded.

Example 46 includes the method of example 40, in which the electrophysiological signals acquired by the surface electrodes are recorded by multiplexing at least some of the electrodes.

Example 47 includes the method of example 40, in which the spatially resolved time-series data set is generated by applying a surface Laplacian method to the obtained time-series data of electrophysiological signals.

Example 48 includes the method of example 40, in which the spatial filtering includes yielding a distribution of location-based signal sources associated with the electrophysiological signals, the distribution including an emphasized group of signal sources corresponding to the anatomical structure distinguished from a suppressed group of signal sources corresponding to other locations from that of the anatomical structure.

Example 49 includes the method of example 40, in which the processing the spatially resolved time-series data set includes determining a presence of an electrophysiological signal wave emanating from a source associated with the anatomical structure within a predetermined frequency range.

Example 50 includes the method of example 40, including mapping the wave propagation parameters to an image associated with the anatomical structure of the subject.

Example 51 includes the method of example 40, including comparing the wave propagation parameters to a standard set of wave propagation parameters to distinguish the physiological function as a healthy function or a dysfunction.

Example 52 includes the method of example 40, including processing the wave propagation parameters with an uncertainty value associated with each parameter to determine statistical information.

Example 53 includes the method of example 52, in which the statistical information includes a probability of the physiological function of the anatomical structure associated with an abnormality or degree of severity.

Example 54 includes the method of example 40, in which the acquiring the electrophysiological signals is noninvasive to the subject's body and operable autonomously by the electrode array.

Example 55 includes the method of example 40, in which the output includes a graph displaying at least one of the wave propagation parameters or summary statistics of the wave propagation parameters.

Example 56 includes the method of any of examples 40-55, in which the electrophysiological signals are electrogastrogram signals, and the anatomical structure includes a tissue or organ associated with the gastrointestinal system.

In some embodiments in accordance with the present technology (example 57), a method for electrophysiological monitoring includes acquiring electrophysiological signals from surface electrodes of an electrode array coupled to skin of a subject to obtain time-series data of the electrophysiological signals, in which the surface electrodes of the electrode array are spatially arranged about an anatomical structure on the subject's body with at least one electrode placed with reference to an anatomical landmark and other electrodes of the electrode array each placed at a spatial distance from another of the surface electrodes, whereby all the surface electrodes have a determined location with respect to the anatomical landmark; processing the time-series data to produce processed time-series data, in which the processing includes spectral filtering the time-series data, down-sampling the time-series data, or removing signal artifacts from the time-series data; determining average intensity values of the electrophysiological signals over a course of the time-series data; mapping the average intensity values to locations where the of the surface electrodes are coupled to the subject; and producing an electrophysiological signal heat map output of the mapped average intensity values on one or both of a graph and image of an anatomical structure of the subject's body, in which the mapped average intensity values are associated with a physiological function of the anatomical structure.

Example 58 includes the method of example 57, including generating a spatially resolved time-series data set by spatially filtering the time-series data, in which the spatially resolved time-series data set includes a reduced amount of data than the obtained time-series data of electrophysiological signals, in which the determined average intensity values mapped to the locations are based on the spatially resolved time-series data set.

Example 59 includes the method of example 58, in which the spatially resolved time-series data set is generated by applying a surface Laplacian method to the obtained time-series data of electrophysiological signals.

Example 60 includes the method of example 58, in which the spatial filtering includes yielding a distribution of location-based signal sources associated with the electrophysiological signals, the distribution including an emphasized group of signal sources corresponding to the anatomical structure distinguished from a suppressed group of signal sources corresponding to other locations from that of the anatomical structure.

Example 61 includes the method of example 57, in which the electrophysiological signal heat map output is indicative of localized functional activity of the anatomical structure.

Example 62 includes the method of example 57, in which the electrode array includes at least a 5×5 grid of the surface electrodes.

Example 63 includes the method of example 57, in which the electrode array includes surface Laplacian electrodes, and in which the acquiring the electrophysiological signals is from the surface Laplacian electrodes, the surface Laplacian electrodes are structured to include concentric rings operable to provide spatially resolved information in the obtained time-series data set.

Example 64 includes the method of example 57, including selecting one surface electrode of the electrode array as a reference electrode; selecting one or more other surface electrodes of the electrode array as one or more measurement electrodes; and recording the electrophysiological signals from the selected surface electrodes.

Example 65 includes the method of example 57, in which the electrophysiological signals acquired by the surface electrodes are simultaneously recorded.

Example 66 includes the method of example 57, in which the electrophysiological signals acquired by the surface electrodes are recorded by multiplexing the one or more measurement electrodes.

Example 67 includes the method of example 57, in which the acquiring the electrophysiological signals is noninvasive to the subject's body and operable autonomously by the electrode array.

Example 68 includes the method of any of examples 57-67, in which the electrophysiological signals are electrogastrogram signals, and the anatomical structure includes a tissue or organ associated with the gastrointestinal system.

In some embodiments in accordance with the present technology (example 69), a method for electrophysiological monitoring includes acquiring electrophysiological signals from electrodes of an electrode array coupled to skin of a subject to obtain time-series data of the electrophysiological signals; processing the time-series data to produce processed time-series data, in which the processing includes spectral filtering the time-series data, down-sampling the time-series data, or removing signal artifacts from the time-series data; and processing spatially resolved time-series data based on the electrophysiological signals to determine wave propagation parameters including one or both of direction and speed for each time point of interest of the acquired electrophysiological signals, in which the wave propagation parameters are associated with a physiological function of an anatomical structure of the subject's body to which the electrode array is coupled.

Example 70 includes the method of example 69, including producing an electrophysiological monitoring output that includes the determined wave propagation parameters to provide information on the physiological function of the anatomical structure of the subject's body.

Example 71 includes the method of example 70, in which the electrophysiological monitoring output includes a graph displaying at least one of the wave propagation parameters or summary statistics of the wave propagation parameters.

Example 72 includes the method of example 69, in which the electrode array includes a reference electrode and two or more measurement electrodes, and the obtained time-series data includes a plurality of differential time-series data between recorded electrophysiological signals from the reference electrode and recorded electrophysiological signals from at least one of the two or more measurement electrodes.

Example 73 includes the method of example 69, in which the electrode array includes at least a 5×5 grid of the electrodes.

Example 74 includes the method of example 69, in which the electrode array includes surface Laplacian electrodes structured to include concentric rings operable to provide spatially resolved information in the obtained time-series data.

Example 75 includes the method of example 69, spatially filtering the time-series data to generate the spatially resolved time-series data set that includes a reduced amount of data than the obtained time-series data of electrophysiological signals.

Example 76 includes the method of example 75, in which the spatially resolved time-series data is generated by applying a surface Laplacian method to the obtained time-series data of electrophysiological signals.

Example 77 includes the method of example 75, in which the spatial filtering includes yielding a distribution of location-based signal sources associated with the electrophysiological signals, the distribution including an emphasized group of signal sources corresponding to the anatomical structure distinguished from a suppressed group of signal sources corresponding to other locations from that of the anatomical structure.

Example 78 includes the method of example 69, in which the producing the wave propagation parameters includes analyzing phase information of the spatially resolved time-series data set.

Example 79 includes the method of example 69, including comparing the wave propagation parameters to a standard set of wave propagation parameters to distinguish the physiological function as a healthy function or a dysfunction.

Example 80 includes the method of example 69, including processing the wave propagation parameters with an uncertainty value associated with each parameter to determine statistical information, in which the statistical information includes a probability of the physiological function of the anatomical structure associated with an abnormality or degree of severity.

Example 81 includes the method of example 69, including determining average intensity values of the acquired electrophysiological signals over a course of the time-series data; and mapping the average intensity values to locations where the of the surface electrodes are located with respect to the subject's body to produce an electrophysiological signal heat map, in which the electrophysiological signal heat map includes one or both of a graph and image having the average intensity values displayed with respect to an anatomical structure of the subject's body.

Example 82 includes the method of example 69, including selecting one electrode of the electrode array as a reference electrode; selecting two or more other electrodes of the electrode array as two or more measurement electrodes; and recording the electrophysiological signals from the selected electrodes.

Example 83 includes the method of example 82, in which the time-series data includes a plurality of differential time-series data between the recorded electrophysiological signals from the reference electrode and the recorded electrophysiological signals from at least one of the two or more measurement electrodes.

Example 84 includes the method of example 69, in which the electrophysiological signals acquired by the electrodes are simultaneously recorded.

Example 85 includes the method of example 69, in which the electrophysiological signals acquired by the electrodes are recorded by multiplexing at least some of the electrodes.

Example 86 includes the method of example 69, in which the processing the spatially resolved time-series data includes determining a presence of an electrophysiological signal wave emanating from a source associated with the anatomical structure within a predetermined frequency range.

Example 87 includes the method of any of examples 60-86, in which the electrophysiological signals are electrogastrogram signals, and the anatomical structure includes a tissue or organ associated with the gastrointestinal system.

In some embodiments in accordance with the present technology (example 88), a system for characterizing gastrointestinal functions includes an array of electrodes spatially arranged and in contact with skin of a subject over the gastrointestinal region to record gut electrophysiology signals; and a processing unit in communication with the array of electrodes to receive gut electrophysiology signals and including a processor that processes the gut electrophysiology signals to determine spatial propagation of a gastric slow-wave signal across time associated with the gut electrophysiology of the subject.

Example 89 includes the system of example 88, in which the processing unit is configured to provide decision support information for a user including the subject, a clinician, or a caregiver.

Example 90 includes the system of example 88, in which the electrode spacing and measurement area of the array of electrodes are spatially arranged to avoid spatial aliasing of the gastric slow-wave signal.

Example 91 includes the system of example 90, in which a spatial arrangement of the array of electrodes is based on imaging data or previous medical history.

Example 92 includes the system of example 91, in which the imaging data includes electrical impedance tomography data.

Example 93 includes the system of example 88, in which the electrodes include a physical design to directly record the surface Laplacian.

Example 94 includes the system of example 88, in which the processing unit is configured to estimate the surface Laplacian.

Example 95 includes the system of example 88, in which the processing unit is configured to estimate at least one of presence, direction, or speed of the gastric slow-wave signal.

Example 96 includes the system of example 88, including a biopotential amplifier to filter and/or digitize the recorded gut electrophysiological signals as signal data provided to the data processing unit.

Example 97 includes the system of example 88, in which the electrodes of the array are spatially arranged about the gastrointestinal region with at least one electrode placed with reference to an anatomical landmark of the gastrointestinal region and other electrodes of the array are placed at a spatial distance from another of the electrodes.

Example 98 includes the system of example 97, in which the array of electrodes includes a 5×5 grid.

Example 99 includes the system of example 88, in which the anatomical landmark of the gastrointestinal region includes the xiphoid.

Example 100 includes the system of example 88, in which the system includes flexible electronic components attachable to the skin of the subject to record signals associated with the gut electrophysiology.

Implementations of the subject matter and the functional operations described in this patent document can be implemented in various systems, digital electronic circuitry, or in computer software, firmware, or hardware, including the structures disclosed in this specification and their structural equivalents, or in combinations of one or more of them. Implementations of the subject matter described in this specification can be implemented as one or more computer program products, i.e., one or more modules of computer program instructions encoded on a tangible and non-transitory computer readable medium for execution by, or to control the operation of, data processing apparatus. The computer readable medium can be a machine-readable storage device, a machine-readable storage substrate, a memory device, a composition of matter effecting a machine-readable propagated signal, or a combination of one or more of them. The term "data processing unit" or "data processing apparatus" encompasses all apparatus, devices, and machines for processing data, including by way of example a programmable processor, a computer, or multiple processors or computers. The apparatus can include, in addition to hardware, code that creates an execution environment for the computer program in question, e.g., code that constitutes processor firmware, a protocol stack, a database management system, an operating system, or a combination of one or more of them.

A computer program (also known as a program, software, software application, script, or code) can be written in any form of programming language, including compiled or interpreted languages, and it can be deployed in any form, including as a stand-alone program or as a module, component, subroutine, or other unit suitable for use in a computing environment. A computer program does not necessarily correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

The processes and logic flows described in this specification can be performed by one or more programmable processors executing one or more computer programs to perform functions by operating on input data and generating output. The processes and logic flows can also be performed by, and apparatus can also be implemented as, special purpose logic circuitry, e.g., an FPGA (field programmable gate array) or an ASIC (application specific integrated circuit).

Processors suitable for the execution of a computer program include, by way of example, both general and special purpose microprocessors, and any one or more processors of any kind of digital computer. Generally, a processor will receive instructions and data from a read only memory or a random access memory or both. The essential elements of a computer are a processor for performing instructions and one or more memory devices for storing instructions and data. Generally, a computer will also include, or be operatively coupled to receive data from or transfer data to, or both, one or more mass storage devices for storing data, e.g., magnetic, magneto optical disks, or optical disks. However, a computer need not have such devices. Computer readable media suitable for storing computer program instructions and data include all forms of nonvolatile memory, media and memory devices, including by way of example semiconductor memory devices, e.g., EPROM, EEPROM, and flash memory devices. The processor and the memory can be supplemented by, or incorporated in, special purpose logic circuitry.

It is intended that the specification, together with the drawings, be considered exemplary only, where exemplary means an example. As used herein, the singular forms "a", "an" and "the" are intended to include the plural forms as well, unless the context clearly indicates otherwise. Additionally, the use of "or" is intended to include "and/or", unless the context clearly indicates otherwise.

While this patent document contains many specifics, these should not be construed as limitations on the scope of any invention or of what may be claimed, but rather as descriptions of features that may be specific to particular embodiments of particular inventions. Certain features that are described in this patent document in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. Moreover, the separation of various system components in the embodiments described in this patent document should not be understood as requiring such separation in all embodiments.

Various embodiments described herein are described in the general context of methods or processes, which may be implemented in one embodiment by a computer program product, embodied in a computer-readable medium, including computer-executable instructions, such as program code, executed by computers in networked environments. A computer-readable medium may include removable and non-removable storage devices including, but not limited to, Read Only Memory (ROM), Random Access Memory (RAM), compact discs (CDs), digital versatile discs (DVD), Blu-ray Discs, etc. Therefore, the computer-readable media described in the present application include non-transitory storage media. Generally, program modules may include routines, programs, objects, components, data structures, etc. that perform particular tasks or implement particular abstract data types. Computer-executable instructions, associated data structures, and program modules represent examples of program code for executing steps of the methods disclosed herein. The particular sequence of such executable instructions or associated data structures represents examples of corresponding acts for implementing the functions described in such steps or processes.

For example, one aspect of the disclosed embodiments relates to a computer program product that is embodied on a non-transitory computer readable medium. The computer program product includes program code for carrying out any one or and/or all of the operations of the disclosed embodiments.

In some embodiments, the disclosed techniques can be implemented by a device that includes a processor (e.g., a microprocessor) and a memory that includes processor executable instructions. The processor executable instructions, when executed by the processor, configure the device to carry out the various disclosed techniques, including processing digital data that represents underlying physical entities, such as images or electrical signals of a body's organs, tissues or other physical entities.

Only a few implementations and examples are described and other implementations, enhancements and variations can be made based on what is described and illustrated in this patent document.

What is claimed is:

1. A device for electrophysiological monitoring, comprising:
    an electrophysiological sensor including an array of electrodes spatially arranged on a substrate and operable to acquire electrophysiological signals from the electrodes of the array to obtain time-series data of the electrophysiological signals, wherein the array of the electrodes includes a reference electrode and two or more measurement electrodes, and wherein the measurement electrodes are spaced on the substrate at a predetermined spatial distance from one another and from the reference electrode, whereby all the electrodes have a determined location with respect to each other;
    an electronics unit including a signal conditioning circuit to amplify the acquired electrophysiological signals; and
    a data processing unit including a processor to process data based on the amplified acquired electrophysiological signals, the data processing unit configured to spatially filter the time-series data to generate a spatially resolved time-series data set that includes a reduced amount of data than the obtained time-series data of electrophysiological signals, and to process the spatially resolved time-series data set to determine wave propagation parameters including one or both of direction and speed for each time point of interest of the acquired electrophysiological signals, wherein the wave propagation parameters are associated with a physiological function of an anatomical structure of a subject's body to which the electrophysiological sensor is configured to be in contact,
    wherein the data processing unit is configured to process the spatially resolved time-series data set to determine the wave propagation parameters by producing an estimated surface Laplacian time-series data set and analyzing phase information of the estimated surface Laplacian time-series data set to determine the one or both of direction and speed for each time point of interest of the acquired electrophysiological signals.

2. The device of claim 1, wherein the obtained time-series data includes a plurality of differential time-series data between recorded electrophysiological signals from the reference electrode and recorded electrophysiological signals from at least one of the two or more measurement electrodes.

3. The device of claim 1, wherein the array includes at least a 5×5 grid of the electrodes.

4. The device of claim 1, wherein the electrophysiological sensor is noninvasive to the subject's body and autonomously operable to passively acquire the electrophysiological signals.

5. The device of claim 1, wherein the data processing unit is configured to determine the wave propagation parameters by analyzing phase information of the spatially resolved time-series data set.

6. The device of claim 1, wherein the data processing unit is configured to produce an electrophysiological monitoring output that includes the determined wave propagation parameters to provide information on the physiological function of the anatomical structure of the subject's body.

7. The device of claim 6, wherein the electrophysiological monitoring output includes a graph displaying at least one of the wave propagation parameters or summary statistics of the wave propagation parameters.

8. The device of claim 1, wherein the data processing unit is configured to compare the wave propagation parameters to a standard set of wave propagation parameters to distinguish the physiological function as a healthy function or a dysfunction.

9. The device of claim 1, wherein the data processing unit is configured to process the wave propagation parameters with an uncertainty value associated with each parameter to determine statistical information, wherein the statistical information includes a probability of the physiological function of the anatomical structure associated with an abnormality or degree of severity.

10. The device of claim 1, wherein the data processing unit is configured to determine average intensity values of the acquired electrophysiological signals over a course of the time-series data, and to map the average intensity values to locations where the electrodes of the array are with respect to the subject's body to produce an electrophysiological signal heat map, the electrophysiological signal heat map including one or both of a graph and image having the average intensity values displayed with respect to an anatomical structure of the subject's body.

11. The device of claim 1, further comprising:
an external computing device in which the data process unit resides that is external with respect to the electrophysiological sensor and the signal conditioning circuit; and
a wireless communications unit to wirelessly transmit the amplified signals to the external computing device.

12. The device of claim 11, wherein the external computing device includes a smartphone, a tablet, a laptop computer, a desktop computer, or a wearable computing device including a smartwatch or a smartglasses device.

13. The device of claim 11, wherein the external computing device is in communication with one or more computers over the Internet, and the one or more computers are configured to process or store one or more of the obtained time-series data or the wave propagation parameters.

14. The device of claim 1, wherein one or both of the electronics unit and the data processing unit is configured to spectrally filter the time-series data, down-sample the time-series data, or remove signal artifacts from the time-series data.

15. The device of claim 1, wherein the electrophysiological sensor includes one or more marks on substrate indicating a place to align the electrophysiological sensor with an anatomical landmark of the subject.

16. The device of claim 1, wherein the electrophysiological sensor includes a securement component including an adhesive, a belt or a strap.

17. The device of claim 1, wherein the substrate includes a flexible substrate including an electrically insulative material and structured to adhere to skin of the subject.

18. The device of claim 1, wherein the electrophysiological signals are electrogastrogram signals, and the anatomical structure includes a tissue or organ associated with the gastrointestinal system of the subject.

19. A method for electrophysiological monitoring, comprising:
acquiring electrophysiological signals from surface electrodes of an electrode array coupled to skin of a subject to obtain time-series data of the electrophysiological signals;
processing the time-series data to produce processed time-series data, wherein the processing includes spectral filtering the time-series data, down-sampling the time-series data, or removing signal artifacts from the time-series data;
spatially filtering the processed time-series data to generate a spatially resolved time-series data set, wherein the spatially resolved time-series data set includes a reduced amount of data than the processed time-series data of electrophysiological signals;
processing the spatially resolved time-series data set to extract wave propagation parameters including one or both of direction and speed for each time point of interest of the acquired electrophysiological signals, wherein the wave propagation parameters are associated with a physiological function of an anatomical structure of the subject's body to which the electrode array is coupled, the producing the wave propagation parameters includes analyzing phase information of the spatially resolved time-series data set; and
producing an electrophysiological monitoring output that includes the extracted wave propagation parameters to provide information on the physiological function of the anatomical structure of the subject's body,
wherein the spatially resolved time-series data set is generated by applying a surface Laplacian method to the obtained time-series data of electrophysiological signals, comprising producing an estimated surface Laplacian time-series data set and analyzing phase information of the estimated surface Laplacian time-series data set to determine the one or both of direction and speed for each time point of interest of the acquired electrophysiological signals.

20. The method of claim 19, wherein the surface electrodes of the electrode array are spatially arranged about the anatomical structure on the subject's body with at least one electrode placed with reference to an anatomical landmark and other electrodes of the electrode array each placed at a spatial distance from another of the surface electrodes, whereby all the surface electrodes have a determined location with respect to the anatomical landmark.

21. A device for electrophysiological monitoring of gastric slow waves in a subject's gastrointestinal system, comprising:

an electrophysiological sensor including an array of electrodes spatially arranged on a substrate and operable to acquire electrophysiological signals from the electrodes of the array to obtain time-series data of the electrophysiological signals, wherein the array of the electrodes includes a reference electrode and two or more measurement electrodes, wherein the measurement electrodes are spaced on the substrate at a predetermined spatial distance from one another and from the reference electrode, and wherein the array of electrodes are spaced on the substrate in a grid of at most five rows and at most five columns, whereby all the electrodes have a determined location with respect to the each other;

an electronics unit including a signal conditioning circuit to amplify the acquired electrophysiological signals; and a data processing unit including a processor to process data based on the amplified acquired electrophysiological signals, the data processing unit configured to spatially filter the time-series data to generate a spatially resolved time-series data set that includes a reduced amount of data than the obtained time-series data of electrophysiological signals, and to process the spatially resolved time-series data set to determine gastric slow-wave propagation parameters including one or both of direction and speed for each time point of interest of the acquired electrophysiological signals, wherein the gastric slow-wave propagation parameters are associated with a physiological function of a tissue or organ associated with the gastrointestinal system of a subject's body to which the electrophysiological sensor is configured to be in contact, wherein the data processing unit is configured to process the spatially resolved time-series data set to determine the gastric slow-wave propagation parameters by producing an estimated surface Laplacian time-series data set and analyzing phase information of the estimated surface Laplacian time-series data set to determine spatial wave properties including the one or both of the direction and speed of the gastric slow-wave for each time point of interest.

* * * * *

UNITED STATES PATENT AND TRADEMARK OFFICE
CERTIFICATE OF CORRECTION

PATENT NO. : 11,006,838 B2
APPLICATION NO. : 16/303610
DATED : May 18, 2021
INVENTOR(S) : Todd Coleman et al.

It is certified that error appears in the above-identified patent and that said Letters Patent is hereby corrected as shown below:

On the Title Page
On Page 2, item (56), under "OTHER PUBLICATIONS", in Column 1, Line 5, delete "propa-gation,"" and insert --propagation,"--, therefor.
On Page 3, item (56), under "OTHER PUBLICATIONS", in Column 1, Line 15, delete "Neurogastroen-terology" and insert --Neurogastroenterology--, therefor.

In the Specification
In Column 3, Line 59, delete "the of the" and insert --the--, therefor.
In Column 4, Line 46, delete "disease state" and insert --diseased state--, therefor.
In Column 6, Line 19, delete "and" and insert --an--, therefor.
In Column 11, Line 37, delete "a an" and insert --an--, therefor.
In Column 14, Line 40, delete "separate" and insert --separated--, therefor.
In Column 18, Line 9, delete "estimate of" and insert --estimate--, therefor.
In Column 22, Line 20, delete "intestine" and insert --intestine's--, therefor.
In Column 26, Line 8, delete "(p" and insert --φ--, therefor.
In Column 26, Line 32, delete "five male, three female," and insert --five males, three females,--, therefor.
In Column 29, Line 45, delete "Table 1," and insert --in Table 1,--, therefor.
In Column 30, Line 61, delete "gastroparetic" and insert --gastroparesis--, therefor.
In Column 33, Line 40, delete "acetylocholine," and insert --acetylcholine,--, therefor.
In Column 33, Line 41, delete "acetylacholine" and insert --acetylcholine--, therefor.
In Column 34, Line 51, delete "recording." and insert --recorded.--, therefor.
In Column 35, Line 17, delete "though" and insert --through--, therefor.
In Column 36, Line 64, delete "remote" and insert --remotely--, therefor.
In Column 38, Line 37, delete "the of the" and insert --the--, therefor.
In Column 40, Line 33, delete "the of the" and insert --the--, therefor.
In Column 42, Line 58, delete "the of the" and insert --the--, therefor.
In Column 44, Line 65, delete "the of the" and insert --the--, therefor.

Signed and Sealed this
Seventeenth Day of October, 2023

Katherine Kelly Vidal
*Director of the United States Patent and Trademark Office*